United States Patent
Rajaiah et al.

(10) Patent No.: US 10,780,032 B1
(45) Date of Patent: Sep. 22, 2020

(54) ORAL CARE COMPOSITIONS FOR ACTIVE AGENT DELIVERY

(71) Applicant: The Procter & Gamble Company, Cincinnati, OH (US)

(72) Inventors: Jayanth Rajaiah, Loveland, OH (US); Paul Albert Sagel, Maineville, OH (US); Geoffrey Marc Wise, Reading, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/850,035

(22) Filed: Apr. 16, 2020

Related U.S. Application Data

(60) Provisional application No. 62/838,350, filed on Apr. 25, 2019.

(51) Int. Cl.
| | | |
|---|---|---|
| *A61K 8/22* | (2006.01) | |
| *A61Q 11/00* | (2006.01) | |
| *A61K 8/06* | (2006.01) | |
| *A61K 8/02* | (2006.01) | |

(52) U.S. Cl.
CPC .............. *A61K 8/22* (2013.01); *A61K 8/0204* (2013.01); *A61K 8/06* (2013.01); *A61Q 11/00* (2013.01)

(58) Field of Classification Search
None
See application file for complete search history.

(56) References Cited

U.S. PATENT DOCUMENTS

| | | |
|---|---|---|
| 2,798,053 A | 7/1957 | Brown |
| 2,835,628 A | 5/1958 | Saffir |
| 3,506,720 A | 4/1970 | Model |
| 3,959,458 A | 5/1976 | Agricola et al. |
| 3,988,433 A | 10/1976 | Benedict |
| 4,051,234 A | 9/1977 | Gieske et al. |
| 4,606,913 A * | 8/1986 | Aronson .................. A61K 8/06 424/59 |
| 5,016,784 A | 5/1991 | Batson |
| 5,512,278 A | 4/1996 | Mundschenk |
| 5,741,773 A * | 4/1998 | Zhang ...................... A61P 1/02 424/278.1 |

(Continued)

FOREIGN PATENT DOCUMENTS

| | | |
|---|---|---|
| DE | 102007013040 | 9/2008 |
| EP | 0251591 | 7/1988 |

(Continued)

OTHER PUBLICATIONS

SB Choi, JS Lee. "Jamming and unjamming transition of oil-in-water emulsions under continuous temperature change." Biomicrofluidics, vol. 9, 2015, pp. 034107-1 to 034107-13. (Year: 2015).*

Jasna Brujic, Chaoming Song, Ping Wang, Christopher Briscoe, Guillaume Marty, and Hernan A. Makse. "Measuring the Coordination Number and Entropy of a 3D Jammed Emulsion Packing by Confocal Microscopy." Physical Review Letters, 2007, pp. 248001-1 to 248001-4. (Year: 2007).*

(Continued)

*Primary Examiner* — Isaac Shomer
(74) *Attorney, Agent, or Firm* — Parker D. McCrary

(57) ABSTRACT

An oral care composition with an aqueous phase, hydrophobic phase, active agent, and optionally emulsifier. A jammed emulsion with aqueous phase, hydrophobic phase, active agent, and optionally emulsifier. An oral care composition with aqueous phase, hydrophobic phase, active agent, and optionally emulsifier. Methods of using disclosed compositions for active agent delivery.

35 Claims, 31 Drawing Sheets

(56) References Cited

U.S. PATENT DOCUMENTS

| | | | |
|---|---|---|---|
| 5,891,453 | A | 4/1999 | Sagel et al. |
| 5,894,017 | A | 4/1999 | Sagel et al. |
| 5,989,569 | A | 11/1999 | Dirksing et al. |
| 6,040,160 | A | 3/2000 | Kojima et al. |
| 6,045,811 | A | 4/2000 | Dirksing et al. |
| 6,096,328 | A | 8/2000 | Sagel et al. |
| 6,136,297 | A | 10/2000 | Sagel |
| 6,509,007 | B2 | 1/2003 | Rajaiah |
| 2002/0176827 | A1 | 11/2002 | Rajaiah et al. |
| 2003/0113276 | A1 | 6/2003 | Rajaiah et al. |
| 2005/0008584 | A1 | 1/2005 | Montgomery |
| 2005/0036958 | A1 | 2/2005 | Feng |
| 2005/0063923 | A1 | 3/2005 | Prencipe et al. |
| 2005/0064371 | A1 | 3/2005 | Soukos |
| 2005/0137109 | A1 | 6/2005 | Quan et al. |
| 2005/0137110 | A1 | 6/2005 | Scott et al. |
| 2005/0143274 | A1 | 6/2005 | Ghosh et al. |
| 2006/0019214 | A1 | 1/2006 | Lawrence |
| 2006/0127344 | A1 | 6/2006 | Zofchak |
| 2007/0054233 | A1 | 3/2007 | Rizoiu et al. |
| 2007/0054235 | A1 | 3/2007 | Rizoui et al. |
| 2007/0054236 | A1 | 3/2007 | Rizoiu et al. |
| 2007/0059660 | A1 | 3/2007 | Rizoiu et al. |
| 2007/0280894 | A1* | 12/2007 | Romano .......... A61Q 11/00 424/53 |
| 2008/0274067 | A1 | 11/2008 | Chaffer |
| 2011/0306004 | A1 | 12/2011 | Sagel |
| 2012/0134936 | A1 | 5/2012 | Kwak et al. |
| 2013/0295525 | A1 | 11/2013 | Sagel |
| 2014/0178443 | A1 | 6/2014 | Sagel et al. |
| 2014/0335028 | A1 | 11/2014 | Prencipe et al. |
| 2015/0238399 | A1 | 8/2015 | Spaid et al. |
| 2015/0353699 | A1* | 12/2015 | Foudazi .......... C08J 9/283 521/120 |
| 2016/0038385 | A1 | 2/2016 | Rege |
| 2016/0279039 | A1 | 9/2016 | Giniger |
| 2017/0172864 | A1 | 6/2017 | Evans |
| 2017/0239029 | A1 | 8/2017 | Sagel |
| 2018/0127577 | A1* | 5/2018 | Haase .......... A61Q 19/00 |
| 2018/0133119 | A1 | 5/2018 | Rajaiah et al. |
| 2018/0133120 | A1 | 5/2018 | Rajaiah et al. |
| 2018/0133121 | A1 | 5/2018 | Rajaiah et al. |
| 2018/0133122 | A1 | 5/2018 | Rajaiah et al. |
| 2018/0133128 | A1 | 5/2018 | Rajaiah et al. |
| 2018/0133502 | A1 | 5/2018 | Rajaiah et al. |
| 2018/0140516 | A1 | 5/2018 | Rajaiah et al. |

FOREIGN PATENT DOCUMENTS

| | | | |
|---|---|---|---|
| EP | 1696866 B1 | 9/2006 | |
| EP | 1696866 B1 * | 10/2013 | .......... A61Q 11/00 |
| EP | 3315119 A1 | 10/2016 | |
| GB | 1492660 A | 11/1977 | |
| WO | WO03015656 A2 | 2/2003 | |
| WO | WO2006138550 | 9/2008 | |
| WO | WO2010098761 | 9/2010 | |
| WO | WO2013093743 | 6/2013 | |
| WO | WO-2016196473 A1 * | 12/2016 | .......... A61L 27/16 |
| WO | WO201783570 | 5/2017 | |
| WO | WO2017090998 A1 | 6/2017 | |

OTHER PUBLICATIONS

ICI Americas Inc. "The HLB System a time-saving guide to emulsifier selection." ICI Americas Inc., Wilmington, Delaware, pp. 1-22, Revised Mar. 1980. (Year: 1980).*

ICI Americas Inc. "The HLB System a time-saving guide to emulsifier selection." ICI Americas Inc., Wilmington Delaware, Revised Mar. 1980, pp. 1-22. (Year: 1980).*

All Office Actions, U.S. Appl. Nos. 15/790,702, 15/790,740, 15/790,788, 15/790,820, 15/790,877, 15/790,903, and 15/790,951.

Chemistry and Technology of Silicones, Walter Noll, Academic Press Inc, (Harcourt Brue Javanovich, Publishers, New York), 1968, pp. 282-287 and 409-426.

Kirk-Othmer, Encyclopedia of Chemical Technology, Fourth Edition, vol. 21, pp. 207-218.

Kostansek, Edward, and Updated by Staff, "Emulsions," Kirk-Othrner Encyclopedia of Chemical Technology (2000): 1-24. (Year: 2000).

Marshall et al. "Hydrogen Peroxide: A Review of Its Use in Dentistry", Journal of Periodontology, vol. 66, Issue 9 (Year: 1995).

Mishra, Amul, Ridhi Panola, and A. C. Rana. "Microemuisions: as drug delivery system." J Sci Innov Res 3.4 (2014): 467-474, (Year: 2014).

Penreco, "Intelligent Gel Technology Product Specifications: Versagel M." www.penreco.com. Jun. 2016 (Year: 2016).

www.fao.org, "petroleum jelly-FAO", Prepared at the 51st JECFA (1998), published in FNP 52 Add 6 (1998); 5 page. (Year: 1998).

15503M PCT Search Report and Written Opinion for PCT/US2020/028390 dated Jul. 6, 2020.

15504 PCT Search Report and Written Opinion for PCT/US2020/028391 dated Apr. 16, 2020.

15505M PCT Search Report and Written Opinion for PCT/US2020/028392 dated Jul. 1, 2020.

Ahmad Shakeel et al. "Bigels: A unique class of materials for drug delivery applications", SOFT Materials, vol. 16, No. 22 Jan. 2018, pp. 77-93.

Aland, Sebastian et al. "Simulation of common features and differences of surfactant-based and solid-stabilized emulsions", Colloids and Surfaces a: Physiochemicl and Engineering Aspects, vol. 413, Nov. 5, 2012, pp. 298-302.

Fabian Jansen et al "From Bijels to Pickering Emulsions: a lattice Boltzmann study", ARXIV.Org., Apr. 26, 2010, Cornell University Library.

Fei Wei et. al, "Active colloidal particles at fluid-fluid interfactes", Current Opinion in Colloid and Interface Science, vol. 32., Oct. 31, 2017, pp. 57-68.

GNPD "Lemon Soda Toothpaste" Dec. 6, 2010 retrieved from www.gnpd.com.

Kaganyuk Max et al. "Role of particles in the rheology of solid-stabilized high internal phase emulsions", Journal of Colloid and Interface Science, vol. 540, Mar. 22, 2019, pp. 197-206.

University of Pennsylvania, "Easier Way to make bijels", a complex new form of liquid matter, Jan. 28, 2016—retrieved fromthe Internet: https://www.sciencedaily.com/releases/2016/01/160128160015.htm.

* cited by examiner

ORAL CARE COMPOSITIONS FOR ACTIVE AGENT DELIVERY

FIELD OF THE INVENTION

The present invention relates to oral care compositions for the delivery of active agents, such as bleaching agents. The present invention also relates to hydrophobic phase in hydrophilic phase (i.e. oil-in-water) emulsion compositions for the delivery of active agents, such as bleaching agents. The present invention also relates to jammed oil-in-water emulsions for the delivery of active agents, such as bleaching agents.

BACKGROUND OF THE INVENTION

Teeth can become discolored by the deposition of stains due to exposure to coffee, wine, cola, or other drinks and foods. Thus, consumers desire methods and compositions to whiten teeth. Compositions comprising an active agent, such as peroxide compounds, can be effective at whitening teeth. For example, the nightguard vital tooth bleaching technique with 10% carbamide peroxide (equivalent to 3.3 wt % hydrogen peroxide) has been used to whiten teeth. However, the use of carbamide peroxide at high concentrations still required a long treatment regimen, such as overnight wear, and produced undesirable side effects, such as tooth sensitivity and soft tissue irritation. Since then, many whitening procedures have been developed, but utilized higher concentrations of peroxide compounds, such as greater than 3.3 wt % of hydrogen peroxide, which produced faster whitening times, but led to more frequent and more severe tooth sensitivity.

The introduction of high viscosity gel compositions based on hydrogen peroxide improved the retention of the hydrogen peroxide within the bleaching trays and increased the adhesiveness of the hydrogen peroxide to the surface of the teeth through the use of carboxypolymethylene compounds, such as Carbopol®. Unfortunately, the gel compositions comprising a carboxypolymethylene compound dehydrated the surface of the teeth and interacted with the hydrogen peroxide, which led to a net slowing of the whitening process and led to increased occurrence and severity of tooth sensitivity.

One strategy to mitigate the dehydration of the surface of teeth was to use a hydrophilic phase in hydrophobic phase emulsion (discontinuous aqueous droplets suspended in a continuous hydrophobic medium, such as oil). The aqueous phase droplets included high concentrations of hydrogen peroxide, such as 35%, which corresponded to a lower total concentration of hydrogen peroxide over the entire emulsion composition. These hydrophilic in hydrophobic emulsions allowed the hydrogen peroxide to rapidly migrate to the hydrophilic tooth surface to yield high performance whitening with minimal side effects. Since the peroxide composition, in terms of the entire emulsion, was lower than a corresponding single-phase composition comprising 35% hydrogen peroxide, tooth sensitivity and gum irritation were dramatically reduced or eliminated. In other words, the aqueous phase in hydrophobic emulsions led to targeted peroxide delivery. However, the performance of the hydrophilic in hydrophobic emulsions were limited by the whitening potential of the aqueous droplets closest to the tooth surface.

Thus, there is a need for a composition that can effectively whiten teeth without the negative side effects commonly associated with high concentrations of peroxide compounds.

SUMMARY OF THE INVENTION

Disclosed herein is an oral care composition comprising jammed emulsion, the jammed emulsion comprising (a) at least partially continuous aqueous phase; (b) discontinuous hydrophobic phase; and (c) oral care active agent.

Disclosed herein is an oral care composition comprising jammed emulsion, the jammed emulsion comprising (a) from about 1% to about 20%, by weight of the composition, of at least partially continuous aqueous phase; (b) from about 80% to about 99%, by weight of the composition, of discontinuous hydrophobic phase; and (c) oral care active agent.

Disclosed herein is an oral care composition, such as an oil-in-water emulsion, preferably comprising high internal phase emulsion, even more preferably comprising jammed emulsion, the oral care composition comprising (a) from about 0.01% to about 20%, by volume of the composition, of an at least partially continuous aqueous phase; (b) from about 80% to about 99%, by volume of the composition, of a discontinuous hydrophobic phase; (c) optionally an emulsifier; and (d) from about 0.01% to about 10%, by weight of the composition, of oral care active agent.

Disclosed herein is an oral care composition comprising (a) from about 1% to about 20%, by weight of the composition, of an at least partially continuous aqueous phase, wherein the aqueous phase has a first initial viscosity; (b) from about 80% to about 99%, by weight of the composition, of a discontinuous hydrophobic phase, wherein the hydrophobic phase has a second initial viscosity; (c) optionally an emulsifier; and (d) from about 0.01% to about 1%, by weight of the composition, of an oral care active agent, wherein the composition has a final viscosity that is greater than the first initial viscosity and/or the second initial viscosity.

Disclosed herein is an oral care composition comprising (a) from about 1% to about 20%, by weight of the composition, of an at least partially continuous aqueous phase, wherein the aqueous phase has a first initial yield stress; (b) from about 80% to about 99%, by weight of the composition, of a discontinuous hydrophobic phase, wherein the hydrophobic phase has a second initial yield stress; (c) an emulsifier; and (d) from about 0.01% to about 1%, by weight of the composition, of an oral care active agent, wherein the composition has a final yield stress that is greater than the first initial yield stress and/or the second initial yield stress.

Disclosed is an oral care composition comprising (a) from about 1% to about 20%, by weight of the composition, of an at least partially continuous aqueous phase; (b) from about 80% to about 99%, by weight of the composition, of a discontinuous hydrophobic phase; (c) an emulsifier; and (d) from about 1% to about 10%, by weight of the composition, of an oral care active agent, wherein the composition is stable to macroscopic separation for at least 48 hours at 23° C.

Also disclosed herein are methods of using the oral care compositions, as described herein.

DETAILED DESCRIPTION OF THE INVENTION

Figure 1A:
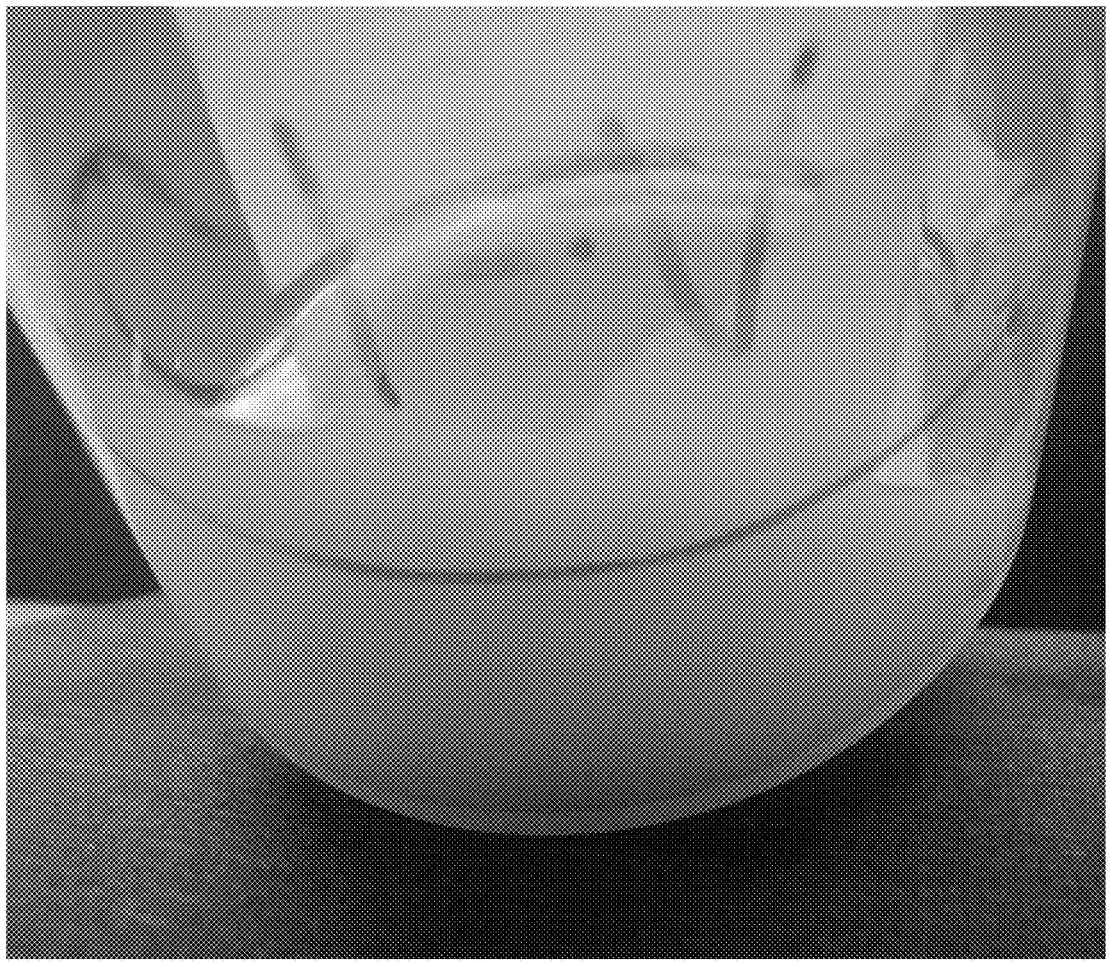
FIG. 1A shows the stable jammed oil-in-water emulsion of Example I-A (84% hydrophobic phase).
Figure 1B:
FIG. 1B shows the stable jammed oil-in-water emulsion of Example I-B (90.4% hydrophobic phase).
Figure 1C:
FIG. 1C shows the stable jammed oil-in-water emulsion of Example I-C (94% hydrophobic phase).
Figure 1D:
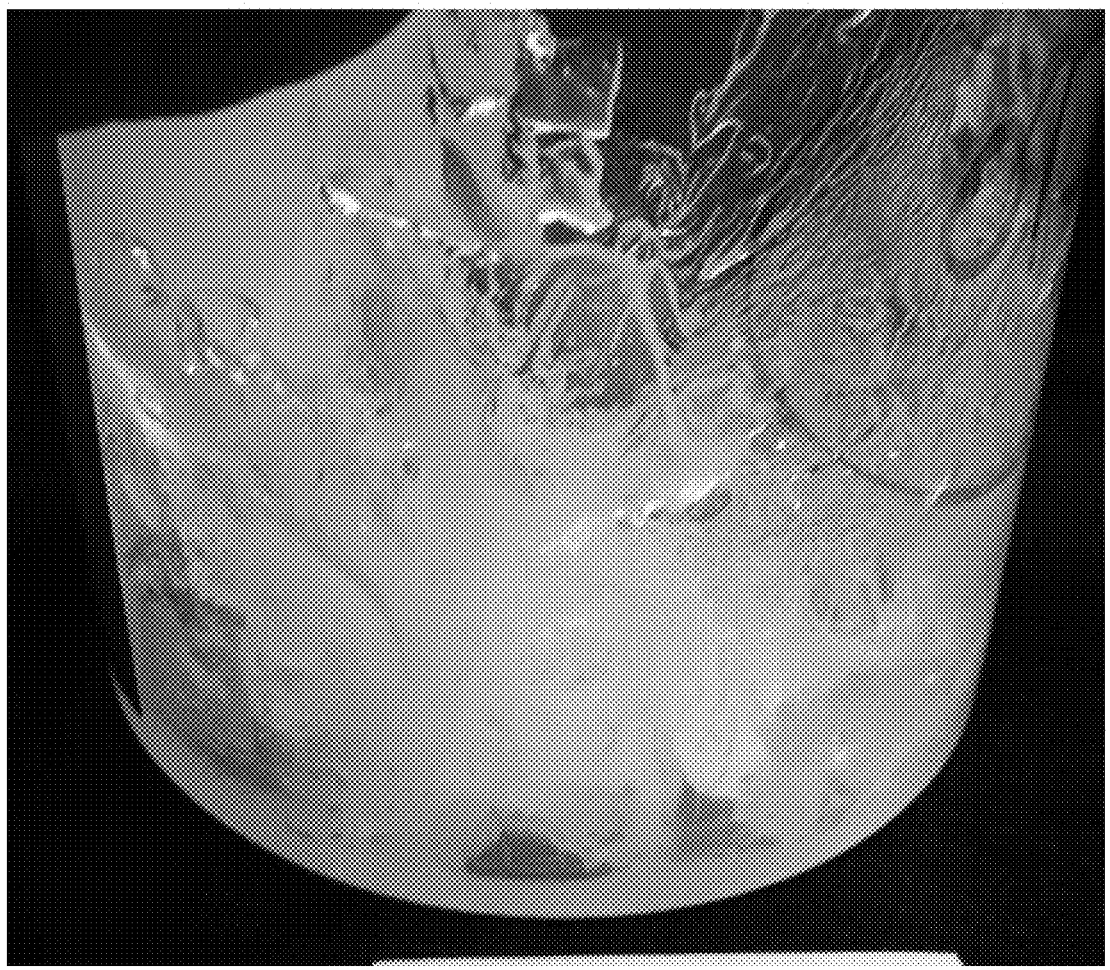
FIG. 1D shows the stable jammed oil-in-water emulsion of Example I-D (96.5% hydrophobic phase).
Figure 1E:
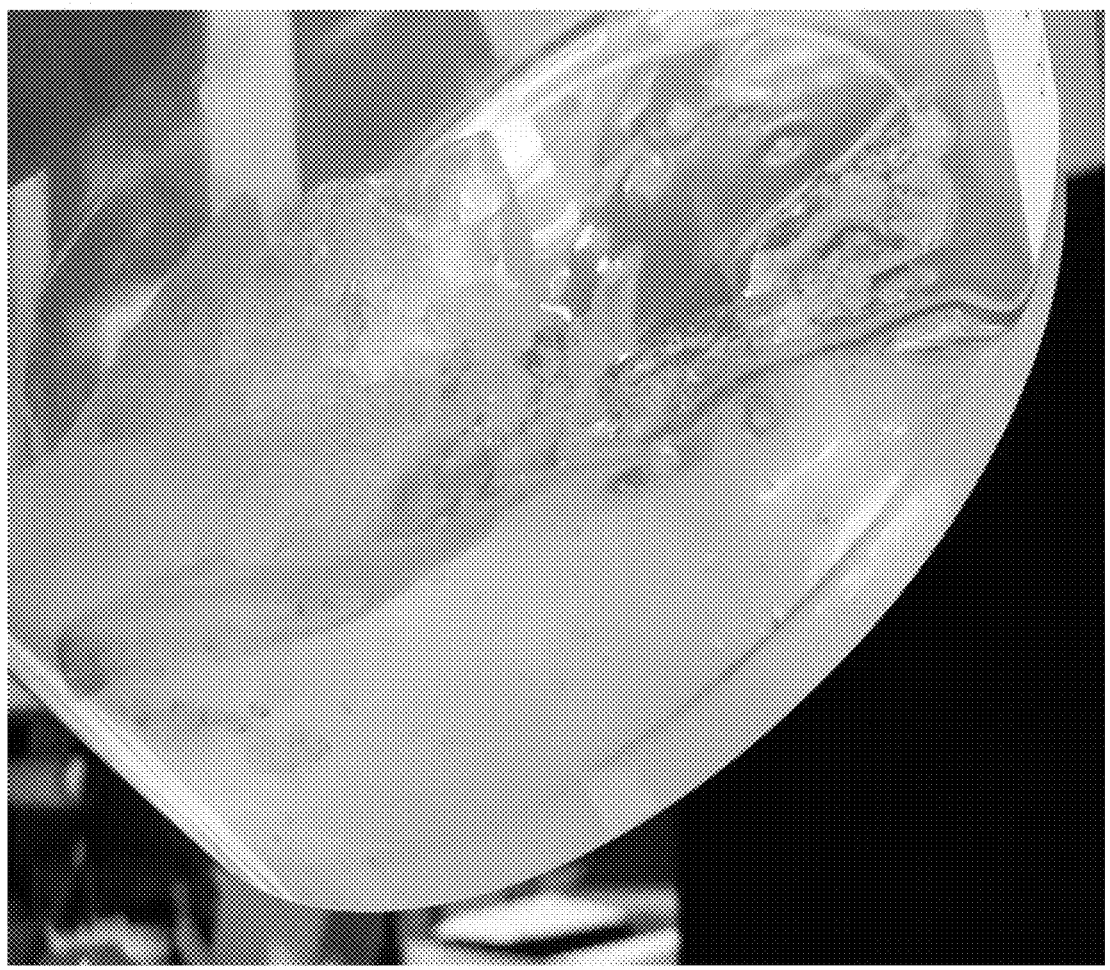
FIG. 1E shows the stable jammed oil-in-water emulsion of Example I-E (97.5% hydrophobic phase).

The present invention is directed to hydrophobic phase in hydrophilic phase emulsions for delivering oral care active agents, such as, for example, bleaching agents, to the oral cavity. Additionally, the present invention is directed to high internal phase emulsions preferably jammed emulsions for the delivery of oral care active agents, such as, for example, bleaching agents, to the oral cavity.

The current invention further improves the whitening performance of multiphase compositions, such as hydrophilic phase in hydrophobic phase emulsions (i.e. water-in-oil emulsions). The current invention maintains the improved tolerability relative to single-phase compositions, while increasing the efficiency of the oral care active agent delivery.

In a water-in-oil emulsion, discrete regions or small droplets of the aqueous phase comprising an active agent are dispersed in a continuous hydrophobic phase, such as oil. While not wishing to be bound by theory, the whitening performance of water-in-oil emulsion systems can be limited by how many aqueous droplets from within the discontinuous phase can reach the surface of teeth. Merely switching to an oil-in-water emulsion, where discrete droplets of a hydrophobic phase are dispersed throughout a predominant continuous aqueous phase comprising an oral care active agent, such as a bleaching agent, can lead to severe tooth sensitivity and gum irritation due to a high total concentration of oral care active agents or whitening agents, such as peroxide compounds.

Surprisingly, the oil-in-water emulsion system can be structured in manner such that the aqueous phase becomes a thin continuous phase between distinct regions of the hydrophobic phase (referred to as a jammed oil-in-water emulsion). In certain aspects of jammed oil-in-water emulsions, the hydrophilic or aqueous phase is the minor component and the hydrophobic phase, despite being the discontinuous phase, is the major component. Microscopically, regions of continuous aqueous phase appear as a thin continuous phase surrounding discrete hydrophobic regions.

Importantly, jammed oil-in-water emulsion have several advantages relative to water-in-oil emulsions. For example, water-in-oil emulsions have a discontinuous aqueous phase of droplets in a hydrophobic phase. In the water-in-oil emulsions, only the droplets that migrate to the tooth surface are involved in the active agent delivery process. Additionally, there is no rapid interaction between aqueous droplets without external forces to create movement within the water-in-oil emulsion. In contrast, the high internal phase emulsions, preferably jammed oil-in-water emulsions of the present invention, the aqueous phase can comprise regions of continuous phase. While not wishing to be bound by theory, it is believed that once any portion of the aqueous phase contacts a tooth surface, the relatively thinner continuous region of aqueous phase can continuously deliver the entire amount of the active agent or bleaching agent to the tooth surface. As the agent is delivered to the tooth surfaces, in certain aspects, the continuity of the aqueous phase enables replenishment of the agent to the surface from the aqueous phase throughout. Surprisingly, even though regions of continuous aqueous phase are able to replenish the surface with the active agent, it is still sufficiently rate limited in the delivered amount of agent per unit contact area as to not exceed the tolerability thresholds of the surfaces. For example, a jammed oil-in-water emulsion with 35% hydrogen peroxide in the aqueous phase is able to be safely applied to the hard and soft tissues with far less irritation than applying an equivalent amount of a 35% aqueous solution to the soft tissues which can cause unwanted and excessive irritation of the soft tissues as the dose per unit area will exceed the ability of the soft tissues to dilute and decompose the peroxide before it can cause the unwanted tissue effects.

Jammed oil-in-water emulsions have several advantages over traditional oil-in-water emulsions. For example, in a traditional oil-in-water emulsion, a minority discontinuous hydrophobic phase is stabilized in a majority continuous aqueous phase. Delivering an active agent, such as a bleaching agent, from a majority continuous aqueous phase can lead to tooth sensitivity and gum irritation when using the high concentrations of bleaching agent needed to quickly and effectively whiten teeth.

Importantly, merely combining a minority aqueous phase with a majority hydrophobic phase will not necessarily lead to a jammed oil-in-water emulsion. In fact, in most cases, combining a minority aqueous phase with a majority hydrophobic phase will lead to a water-in-oil emulsion with discrete droplets of aqueous phase dispersed in the hydrophobic phase, or macroscopic separation.

Surprisingly, as described herein, it was found that by adding the predominant hydrophobic phase to the less predominant hydrophilic phase, a jammed oil-in-water emulsion can be prepared. It is counter intuitive to add the major hydrophobic component to the minor hydrophilic component. The jammed emulsion can be prepared by adding a portion of the hydrophobic phase to the hydrophilic phase followed by mixing and then repeating the procedure until all of the hydrophobic phase has been added to the hydrophilic phase.

Alternatively, the hydrophobic phase may be added in a continuous or pulsed fashion to the hydrophilic phase under constant stirring conditions until all of the hydrophobic phase has been added. Without wishing to be bound by theory, when the hydrophobic phase reaches a certain volume percentage of the total emulsion (i.e. the jamming concentration), the emulsion begins to jam. When the jamming of the emulsion occurs, the viscosity of the emulsion can increase, and the emulsion can become more physically stable. Physical stability of the emulsion can be important to prevent macroscopic separation during the storage of the composition. In contrast, it was surprisingly found that addition of the minor hydrophilic phase to the major hydrophobic phase can lead to macroscopic separation, even when the minor hydrophilic phase is added in a portion-wise manner coupled with mixing.

Without not wishing to be bound by theory it was surprisingly found that bleaching agents can be effective in very low concentrations, if presented in a multi-phase oral care composition as disclosed herein. The present invention comprises an oral care composition comprising an emulsion, preferably a jammed oil-in-water emulsion, the preferred jammed oil-in-water emulsion comprising an aqueous phase, a hydrophobic phase, and from about 0.01% to about 10% of at least one oral care active agent.

Definitions

By "oral care composition", as used herein, is meant a product that it is retained in the oral cavity for a time sufficient to contact dental surfaces or oral tissues. Examples of oral care compositions include dentifrice, tooth gel, subgingival gel, mouth rinse, mousse, foam, mouth spray, lozenge, chewable tablet, chewing gum, tooth whitening strips, floss and floss coatings, breath freshening dissolvable strips, denture care products, or denture adhesive products. The oral care composition may also be incorporated onto strips, trays or films for direct application or attachment to oral surfaces.

The term "dentifrice", as used herein, includes tooth or subgingival-paste, gel, or liquid formulations unless otherwise specified. The dentifrice composition may be a single-phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

The term "immiscible" or "insoluble" as used herein means less than 1 part by weight of the substance dissolves in 100 parts by weight of a second substance.

The term "solubility" as used herein is the maximum number of parts by weight of the substance that can dissolve in 100 parts by weight of a second substance.

The term "phase" as used herein means a physically distinct region or regions, which may be continuous or discontinuous, having one or more properties that are different from another phase. Non-limiting examples of properties that may be different between phases include composition, viscosity, solubility, hydrophobicity, hydrophilicity, visual characteristics, and miscibility. Examples of phases include solids, semisolids, liquids, and gases.

The term "multi-phase oral care composition" as used herein comprises a mixture of two or more phases that are immiscible with each other, for example water-in-oil, oil-in-water emulsions, or mixtures thereof. The phases may be continuous, discontinuous, or combinations thereof. The multi-phase oral care composition or a phase of the multi-phase oral care composition may be solid, liquid, semisolid, or combinations thereof. In preferred aspects the multi-phase oral care composition is semisolid. Examples of multi-phase oral care compositions also include compositions where the phases are multi-continuous including bi-continuous, layered, striped, marbled, ribbons, swirled, and combinations thereof. Examples of multi-phase oral care compositions also include compositions where the phases are tessellated or tiled.

The term "emulsion" as used herein is an example of a multi-phase oral care composition wherein: 1) at least one of the phases is discontinuous and 2) at least one of the phases is continuous. Examples of emulsions include droplets of oil dispersed in water. In this example, the water and oil would be mutually immiscible with each other, oil would be the discontinuous phase, and the water would be the continuous phase.

The term "macro-emulsion" as used herein is an example of an emulsion wherein at least one of the discontinuous phases is visible under a microscope using light with one or more wavelengths from 400 nm to 700 nm. Examples of macro-emulsions include those in which the mass median diameter, volume weighted mean diameter, or surface weighted mean diameter of the regions of at least one of the discontinuous phases is larger than the wavelength of light being used, for instance larger than 0.1, 0.4, or 0.7 micron.

The term "micro-emulsion" as used herein is an example of an emulsion wherein the discontinuous phases is not visible under a microscope using light with one or more wavelengths from 400 nm to 700 nm. Examples of micro-emulsions include those in which the regions of the discontinuous phases are smaller than the wavelength of light being used, for instance smaller than 0.1, 0.4, or 0.7 micron.

The term "oil-in-water emulsion" as used herein is an example of an emulsion wherein 1) the continuous phase is aqueous or hydrophilic, and 2) the discontinuous phase is hydrophobic.

The term "water-in-oil emulsion" as used herein is an example of an emulsion wherein 1) the continuous phase is hydrophobic, and 2) the discontinuous phase is aqueous or hydrophilic.

The term "high internal phase emulsion" as used herein is an example of an emulsion wherein the discontinuous phase comprises more than about 74% by weight or volume of the multi-phase oral care composition. High internal phase emulsions may be oil-in-water emulsions, water-in-oil emulsions, or mixtures thereof.

The term, "jammed emulsion" as used herein, is a high internal phase emulsion 1) wherein the high internal phase emulsion exhibits no more than 5% macroscopic separation after 48 hours at 23° C. measured according to the method specified herein, and/or 2) wherein separate regions of discontinuous phase influence the shape of one another. Examples of jammed emulsions may include high internal phase emulsions in which adjacent or neighboring regions of discontinuous phase influence the shape of one another.

The term "jamming concentration" of a high internal phase emulsion as used herein is the minimum concentration of the discontinuous phase above which the high internal phase emulsion 1) exhibits no more than 5% macroscopic separation after 48 hours at 23° C. measured according to the method specified herein, and/or 2) wherein separate regions of discontinuous phase influence the shape of one another.

The term "jam" or "jamming" of a high internal phase emulsion as used herein is the phenomenon where the high internal phase emulsion transitions to one that 1) exhibits no more than 5% macroscopic separation after 48 hours at 23° C. measured according to the method specified herein and/or 2) wherein separate regions of discontinuous phase influence the shape of one another.

The term "solid" as used herein is a material that, at room temperature, 1) has defined dimensions even when it is not constrained in a container, or 2) maintains its original shape when it is picked up off a surface and subsequently placed back on the surface.

The term "liquid" as used herein is a material that, at room temperature, 1) flows under gravity, or 2) takes the shape of the container it is placed in. Examples of liquids include mineral oil, water, and silicone oil. When a liquid is poured into a container, the exposed surface (the surface that is not in contact with the walls of the container) of liquids may become horizontal and flat due to gravity. Liquids may have a freezing point, melting point or drop melting point as measured according to ASTM method D127 or a congealing point as measured according to ASTM method D938 or a pour point as measured according to ASTM D97 less than about OC, less than about 23° C., or less than about 40° C. Liquids may have a kinematic viscosity measured according to ASTM D445 at 40° C. less than about 10,000 cSt, less than about 1000 cSt, or less than about 100 cSt.

The term "semisolid" as used herein is a material that, at room temperature, 1) has some solid-like properties and some liquid-like properties, or 2) whose ability to meet the above definition of a solid or liquid may depend on the amount of material being evaluated; for example, a small amount of petrolatum placed in a large container may not flow under gravity, and it may not take the shape of the container (thus not meeting the definition of a liquid); but a large amount of petrolatum placed in an large container may flow under gravity, or it may take the shape of the container (thus meeting the definition of a liquid). Examples of semisolids include petrolatum, toothpaste, silicone gels, mayonnaise, butter, lotions, creams, ointments, and jammed emulsions.

The term "lotion" as used herein is a preparation intended for application on the body, surfaces of the oral cavity, or mucosal surfaces. Examples of lotions include hand lotions, skin care lotions, body lotions, suntan lotions, and jammed emulsions.

The term "aqueous phase" as used herein is a phase that comprises water, optionally at least one active agent, and is immiscible with the hydrophobic phase.

The term "hydrophobic phase" as used herein means all components of the composition that are immiscible with the aqueous phase.

The term "equivalent-diameter" of a region or droplet as used herein means the diameter of a sphere having the same volume as the region or droplet.

The term "Dv 50 equivalent-diameter" as used herein is the equivalent-diameter in microns at which 50% of the regions of hydrophobic phase or droplets of aqueous phase are smaller and 50% are larger. The v in the term Dv 50 shows that this refers to the volume distribution. The Dv 50 equivalent-diameter of regions of hydrophobic phase of a multi-phase oral care composition is measured according to the method specified herein.

The term "D[4,3] equivalent-diameter" as used herein is the volume-weighted-mean equivalent-diameter in microns of the regions of hydrophobic phase or droplets of aqueous phase. The D[4,3] equivalent-diameter of regions of hydrophobic phase of a multi-phase oral care composition is measured according to the method specified herein.

The term "D[3,2] equivalent-diameter" as used herein is the surface-weighted-mean equivalent-diameter in microns of the regions of hydrophobic phase or droplets of aqueous phase. The D[3,2] equivalent-diameter of regions of hydrophobic phase of a multi-phase oral care composition is measured according to the method specified herein.

The term "two-dimensional density of droplets of aqueous phase" as used herein means the number of droplets of aqueous phase a) that are present in a square centimeter of a two-dimensional plane in the multi-phase oral care composition and b) wherein the cross-sectional area of the droplets of the aqueous phase in the two-dimensional plane are larger than a specified value.

The term "two-dimensional density of regions of hydrophobic phase" as used herein means the number of regions of hydrophobic phase a) that are present in a square centimeter of a two-dimensional plane in the multi-phase oral care composition and b) wherein the cross-sectional area of the regions of hydrophobic phase in the two-dimensional plane are larger than a specified value.

The term "cone penetration consistency value" as used herein means the depth, in tenths of a millimeter, that a standard cone will penetrate the sample under fixed conditions of mass, time, and temperature. The cone penetration consistency value is measured according to ASTM method D937.

The term "delivery carrier" as used herein comprises a material or an appliance that is used to hold the multi-phase oral care composition against the tooth surface. Examples of delivery carriers include strips or dental trays.

The term "strip" as used herein comprises a material 1) whose longest dimension length is generally greater than its width, and 2) whose width is generally greater than its thickness. Strips may be rectangular, arched, curved, semicircular, have rounded corners, have slits cut into it, have notches cut into it, bent into three dimensional shapes, or combinations thereof. Strips may be solid, semisolid, textured, moldable, flexible, deformable, permanently deformable, or combinations thereof. Strips may be made from plastic sheets including polyethylene, or wax sheets. Examples of strips include a piece of polyethylene about 66 mm long, 15 mm wide and 0.0178 mm thick. Examples of permanently deformable strips include a piece of casting wax sheet about 66 mm long, 15 mm wide, and 0.4 mm thick.

The term "rinseable" as used herein means the material can be rinsed from a surface using water at a certain temperature in a certain period of time. Examples of rinseable materials generally include honey, milk, and compositions comprising oil-in-water emulsions such as Examples I-A, I-B, I-C, I-D, I-E, and I-F below.

The term "dispersible" as used herein means the material can be dispersed in water at a certain temperature. The water-dispersibility of the material is measured according to the method specified herein. Examples of water-dispersible materials generally include compositions comprising oil-in-water emulsions such as Examples I-A, I-B, I-C, I-D, I-E, and I-F below.

The term "macroscopic separation" as used herein is a phenomenon in which at least a portion of one or more components or one or more phases of a composition separates out of the composition. The macroscopic separation is measured according to the method specified herein. The lack of macroscopic separation is a measure of the physical stability of a composition.

The term "heterogenous mixture" as used herein is a heterogenous combination of two or more substances. Examples of heterogenous mixtures include emulsions such as oil-in-water emulsions, and jammed emulsions. Heterogenous mixtures do not include homogenous mixtures (such as solutions where a solute is uniformly dissolved in a solvent).

The term "heterogenous dispersion" as used herein is a heterogenous combination of two or more substances Examples of heterogenous dispersions include emulsions such as oil-in-water emulsions, and jammed emulsions. Heterogenous dispersions do not include homogenous dispersions (such as solutions where a solute is uniformly dissolved in a solvent).

The term "petrolatum" as used herein means a semisolid mixture of hydrocarbons. Petrolatum may have a cone penetration consistency value as measured according ASTM method D937 from about 10 to about 500, preferably from about 25 to about 300, more preferred from about 50 to about 250, or more preferred from about 100 to about 200. Petrolatum may have a melting point or drop melting point as measured according to ASTM method D127 or a congealing point as measured according to ASTM method D938 from about from about 40° C. to about 120° C., preferably from about 50° C. to about 100° C., more preferred from about 50° to about 90° C., or more preferred from about 60° C. to about 80° C.

The term "mineral oil" as used herein means a liquid mixture of hydrocarbons. Mineral oil may have a cone penetration consistency value as measured according ASTM method D937 more than about 600, preferably more than about 500, or more preferred more than about 400. Mineral oil may have a freezing point, melting point or drop melting point as measured according to ASTM method D127 or a congealing point as measured according to ASTM method D938 or a pour point as measured according to ASTM D97 less than about 0° C., less than about 23° C., or less than about 40° C. Mineral oil may have a kinematic viscosity measured according to ASTM D445 at 40° C. less than about 10,000 cSt, less than about 1000 cSt, or less than about 100 cSt.

The term "HLB" of an emulsifier is an expression of its Hydrophile-Lipophile Balance, i.e. the balance of the size and strength of the hydrophilic (water-loving or polar) and the lipophilic (oil loving or non-polar) groups of the emulsifier. The HLB values are quantified as follows:

A. For non-ionic emulsifiers (except those containing propylene oxide, butylene oxide, nitrogen, or sulfur) HLB values are calculated according to the procedure specified in "The HLB system—a time-saving guide to emulsifier selection", from ICI Americas, Wilmington Del. 19897, which is herein incorporated in its entirety by reference, including the various emulsifiers and blends of multiple emulsifiers listed in it along with their HLB values.

B. For ionic emulsifiers HLB values are calculated according to the procedure specified in 1) "A quantitative kinetic theory of emulsion type I, physical chemistry of the emulsifying agent" by J. T. Davies J. H. Schulman (Ed.), Proceedings of the 2nd International Congress on Surface Activity, Academic Press, New York (1957), 2) Davies, J. T. (1959) Proc. Int. Congr. Surf. Act., 1, 426, and/or 3) Davies, J. T. and Rideal, E. K. (1961) Interfacial Phenomena.

C. For all other emulsifiers and those whose HLB values cannot be calculated according to either of the above two procedures, HLB values are measured experimentally according to the experimental procedure specified in "The HLB system—a time-saving guide to emulsifier selection", from ICI Americas, Wilmington Del. 19897.

As used herein, the word "or" when used as a connector of two or more elements is meant to include the elements individually and in combination; for example X or Y, means X or Y or both.

As used herein, the articles "a" and "an" are understood to mean one or more of the material that is claimed or described, for example, "an oral care composition" or "a bleaching agent."

The term "safe and effective amount" as used herein means an amount of a component, high enough to significantly (positively) modify the condition to be treated or to affect the desired whitening result, but low enough to avoid serious side effects (at a reasonable benefit/risk ratio), within the scope of sound medical/dental judgment. The safe and effective amount of a component, will vary with the particular condition being treated, the age and physical condition of the patient being treated, the severity of the condition, the duration of treatment, the nature of concurrent therapy, the specific form employed, and the particular vehicle from which the component is applied.

The term "a sufficient period of time to achieve whitening" as used herein is meant that the composition is used or worn by the participant or the participant is instructed to use or wear the composition for greater than about 10 seconds; or greater than about 1 minute, such as from about 2.5 minutes to about 12 hours (for example overnight treatment), or from about 3 minutes to about 180 minutes; or greater than about 5 minutes, such as from about 5 minutes to about 60 minutes; or greater than about 10 minutes, such as from about 10 minutes to about 60 minutes; or from about 1, 5, 10, or 15 minutes to about 20, 30, 60, 120 minutes per application; or any other numerical range, which is narrower and which falls within such broader numerical range, as if such narrower numerical ranges were all expressly written herein. In addition, the treatments may be applied from about 1, 2, or 3 times a day to about 4, 5, 6 or 7 times a day. The treatments may be applied for from about 1, 2, 3, 4, 5, 6, or about 7 days to about 8, 9, 10, 11, 12, 13, 14, 21, or 28 days or any other numerical range, which is narrower and falls within such broader numerical range, as if such narrower numerical ranges were all expressly written herein. Further, the length of treatment to achieve the desired benefit, for example, tooth whitening, may last for a specified period of time, which may be repeated if necessary, for example from about one day to about six months, from about one day to about 28 days, or from about 7 to about 28 days. The optimal duration and frequency of application will depend on the desired effect, the severity of any condition being treated, the health and age of the patient and like considerations.

The term "dispenser", as used herein, means any pump, tube, or container suitable for dispensing oral care compositions.

All percentages and ratios used herein after are by weight of total composition (wt %), unless otherwise indicated. All percentages, ratios, and levels of ingredients referred to herein are based on the actual amount of the ingredient, and do not comprise solvents, fillers, or other materials with which the ingredient may be combined as a commercially available product, unless otherwise indicated.

All measurements referred to herein are made at about 23° C.+/−1° C. (i.e. room temperature) unless otherwise specified.

All parameters that have a method specified herein are measured using the method specified herein, unless otherwise specified.

"Active and other ingredients" useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

The term "teeth", as used herein, refers to natural teeth as well as artificial teeth or dental prosthesis and is construed to comprise one tooth or multiple teeth. The term "tooth surface" as used herein, refers to natural tooth surface(s) as well as artificial tooth surface(s) or dental prosthesis surface(s) accordingly.

The term "orally acceptable carrier" comprises one or more compatible solid or liquid excipients or diluents which are suitable for use in the oral cavity. By "compatible," as used herein, is meant that the components of the composition are capable of being commingled without interaction in a manner which would substantially reduce the composition's stability and/or efficacy.

While specific reference is made to "consumers" or "patients," throughout the specification, these terms are used interchangeably to refer to any user of the multi-phase oral care composition. The consumer or patient can apply the composition to the oral cavity themselves, or have the composition applied to their oral cavity by a third party, such as a dentist, hygienist, orthodontist, 'or other medical or dental professional.

Jammed Emulsions

As described herein, the present invention relates to multi-phase oral care compositions for the delivery of active agents, such as bleaching agents. The multi-phase oral care composition, as described herein, comprises a high internal phase emulsion, or preferably a jammed oil-in-water emulsion.

Traditional oil-in-water emulsions are multi-phase compositions with a discontinuous hydrophobic phase and a continuous aqueous phase. Stable oil-in-water emulsions can be prepared by combining a minority hydrophobic phase with a majority aqueous phase. Traditional oil-in-water emulsions are discontinuous droplets of hydrophobic phase suspended and/or stabilized within a continuous aqueous phase. As the hydrophobic and aqueous phases are immiscible, generally only a small portion of the hydrophobic phase can be stabilized within the aqueous phase before macroscopic separation occurs.

A high internal phase emulsion can be either oil-in-water or water-in-oil emulsion, wherein there is a high amount of the internal, discontinuous phase, by volume or weight of the multi-phase composition, relative to a traditional emulsion. A high internal phase emulsion can have more of the internal, discontinuous phase, by volume or weight of the total multi-phase composition than the external, continuous phase, by volume or weight of the multi-phase composition. However, the stability of high internal phase emulsions can prove challenging. High internal phase emulsions can suffer from macroscopic separation upon mixing or during storage of the high internal phase emulsions prior to use by a consumer.

As described herein, a jammed emulsion may be an unexpectedly stable high internal phase emulsion. As the concentration of the discontinuous phase of a high internal phase emulsion is increased, regions of discontinuous phase can become sufficiently crowded, such that they can jam against each other with a region of continuous phase between them and deform each other with a region of continuous phase between them. If both the continuous phase and discontinuous phase are liquids, the emulsion can transition into an at least a partially semisolid structure when the jamming transition occurs.

Figure 9A:
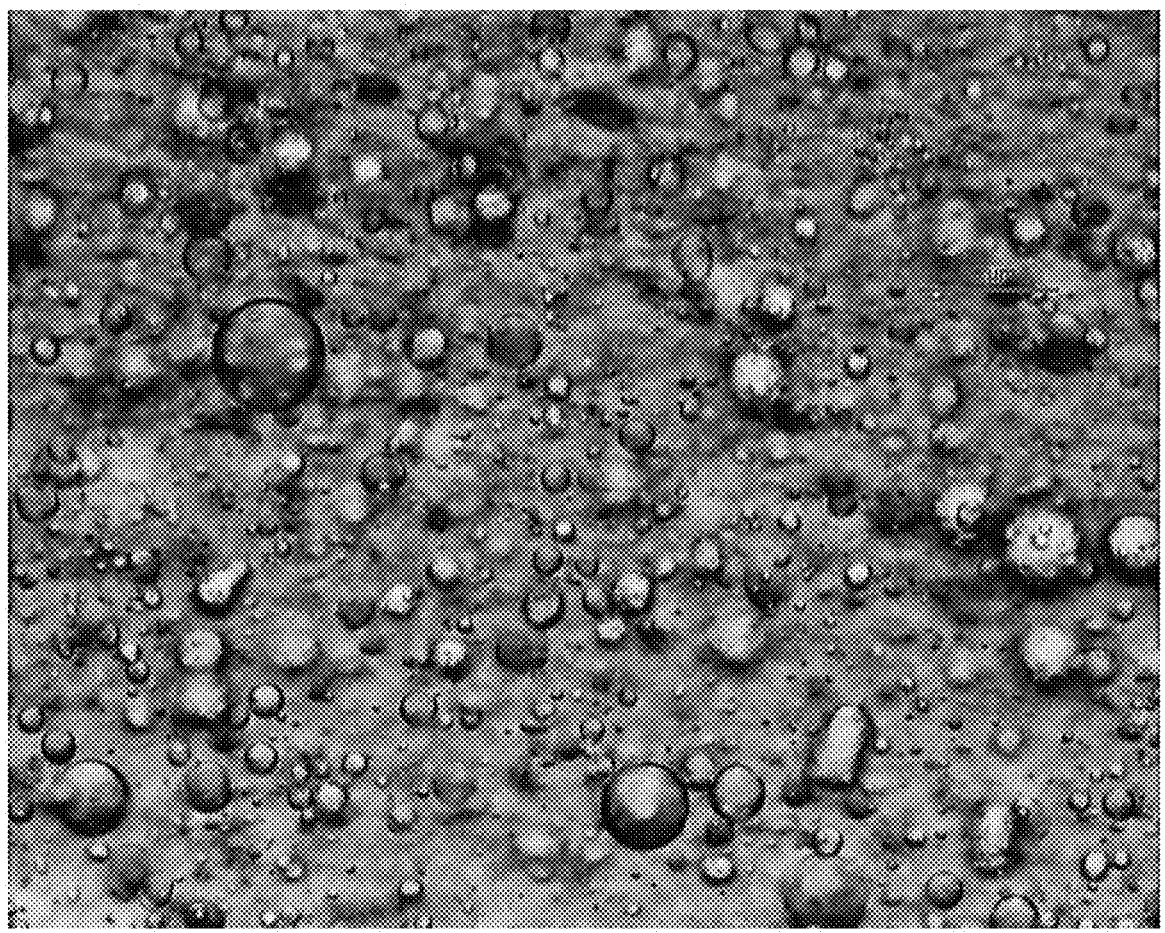
FIG. 9A shows a microscopic image of Comparative Example VI as a water-in-oil emulsion with discrete droplets of aqueous phase dispersed in the hydrophobic phase.
Figure 9B:
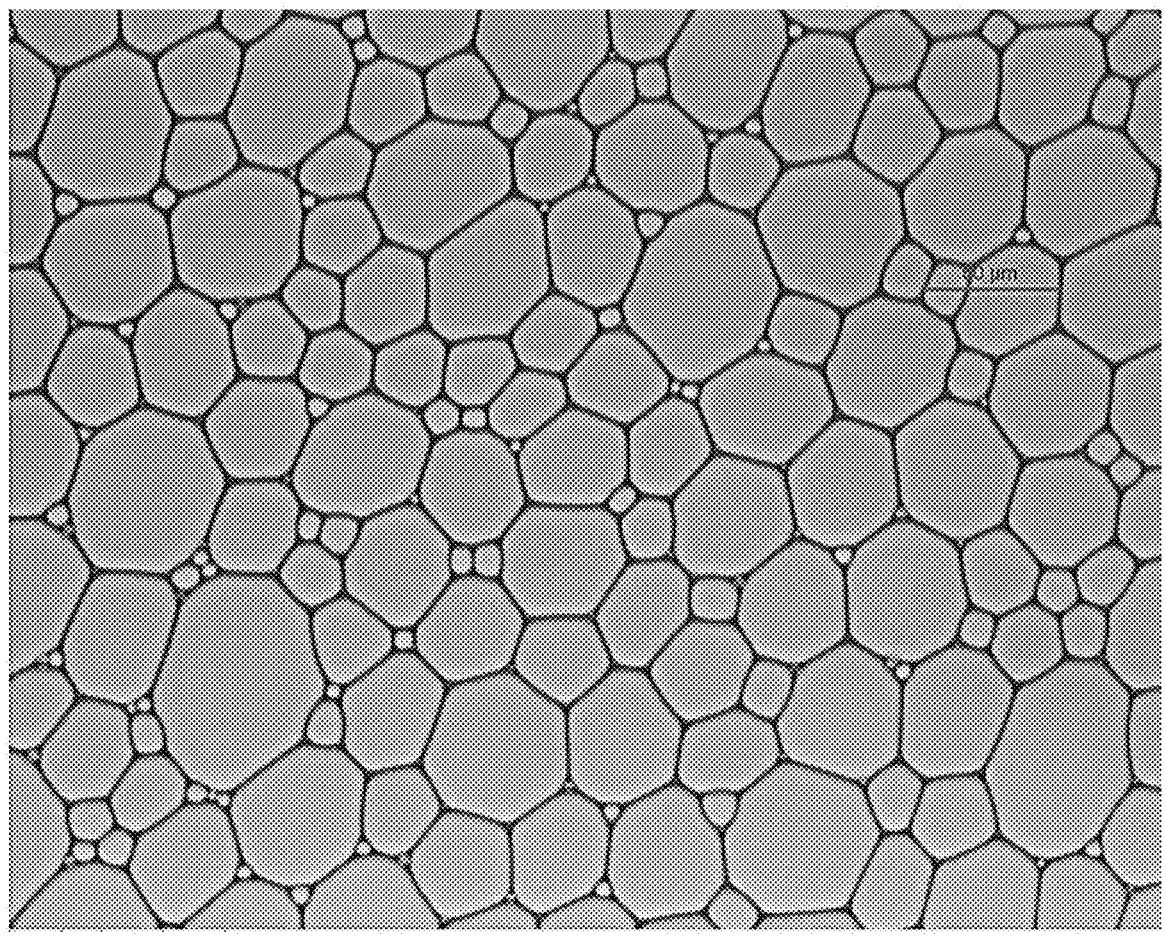
FIG. 9B shows Example I-B as a jammed oil-in-water emulsion with regions of oil dispersed in the aqueous phase.

For example, FIG. 9A shows a microscopic image of Comparative Example VI, which comprises a water-in-oil emulsion, while FIG. 9B is a microscopic image of Example I-B, which comprises a jammed oil-in-water emulsion. The comparison of the images visually shows the structural differences between a water-in-oil emulsion and a jammed oil-in-water emulsion that can contribute to the stability of jammed oil-in-water emulsions.

For convenience, the jammed oil-in-water emulsions, as described herein, can be represented or described in two dimensions along an x-y plane. Additionally, the jammed emulsions can appear two-dimensional in a light microscope, such as in FIG. 9B, due to the focal plane. However, it is to be understood that jammed emulsions are three-dimensional.

Examples of jammed emulsions include those in which, under a microscope, 1) regions of discontinuous phase are or resemble polyhedrons or polygons, with or without rounded corners, with visible jamming between regions of discontinuous phase, with continuous phase sandwiched between regions of discontinuous phase, 2) regions of discontinuous phase are or resemble non-spherical shapes, with visible jamming between regions of discontinuous phase, with continuous phase sandwiched between regions of discontinuous phase, 3) regions of discontinuous phase are in a tessellated or tiled pattern or resemble one, with continuous phase sandwiched between regions of discontinuous phase, or 4) regions of discontinuous phase are in a pattern that resemble a Voronoi diagram with continuous phase sandwiched between regions of discontinuous phase. Examples of jammed emulsions include those in which 1) the cone penetration consistency value or the slide flow distance of the emulsion is less than that of the continuous phase and/or discontinuous phase, or 2) the kinematic viscosity, Brookfield Viscosity, yield stress, shear storage modulus, shear loss modulus, or ratio of the shear storage modulus to the shear loss modulus of the emulsion is more than that of the continuous phase and/or discontinuous phase. Examples of jammed emulsions include those in which, under a microscope, regions of discontinuous phase are or resemble polyhedrons or polygons, with or without rounded corners, with from about 3, 4, 5, 6, 7, 8, 9, 10, 11, 12, 13, 14, 15, or 16 to about 3, 4, 5, 6, 7, 8, 9, 10, 11, 12, 13, 14, 15, or 16 substantially straight sides or substantially flat surfaces with visible jamming between regions of discontinuous phase, with continuous phase sandwiched between regions of discontinuous phase. Examples of jammed emulsions include those in which, under a microscope, portions of regions of discontinuous phase are or resemble polyhedrons or polygons, with or without rounded corners, with from about 1, 2, 3, 4, 5, 6, 7, 8, 9, 10, 11, 12, 13, 14, 15, or 16 to about 1, 2, 3, 4, 5, 6, 7, 8, 9, 10, 11, 12, 13, 14, 15, or 16 substantially straight sides or substantially flat surfaces with visible jamming between regions of discontinuous phase, with continuous phase sandwiched between regions of discontinuous phase.

The jammed emulsion, as described herein, can be prepared by the portion-wise addition or gradual addition or slow addition of the discontinuous phase to the continuous phase. Simply combining the entire discontinuous phase to the continuous phase will not necessarily result in jammed emulsion. A Voronoi diagram can be used to describe and/or illustrate the preparation of a jammed emulsion. For example, as portions of the discontinuous phase are added to the continuous phase, molecules of the discontinuous phase will associate into the closest regions to minimize entropically unfavorable hydrophobic-hydrophilic interactions. Without wishing to be bound by theory, it is believed that adding the entire discontinuous phase to the continuous phase, macroscopic separation will be more likely to occur. Instead, by slowly adding (either by portion-wise addition or a slow continuous addition), the molecules of the discontinuous phase can associate into discrete regions instead of separating macroscopically. As the concentration of the discontinuous phase reaches the jamming concentration, a jamming transition can occur where separate regions of the discontinuous phase can influence the shapes of one another (for example neighboring or adjacent regions of discontinuous phase), which can contribute to the unexpected stability of jammed emulsions. In certain aspects of jammed emulsions, 1) separate regions of the discontinuous phase can influence the shape of one another (for example neighboring or adjacent regions of discontinuous phase), which can lead to a transition from substantially spherical discontinuous regions to at least partially polyhedral discontinuous regions at the jamming concentration, or 2) the emulsion can exhibit a Yield Stress or Brookfield Viscosity greater than that of the constituent aqueous phase and/or the hydrophobic phase measured according to the methods specified herein at 23° C.

The multi-phase oral care compositions, as described herein, can be rinseable with water at a reasonable temperature in a suitable amount of time. A reasonable temperature for the jammed emulsion to be rinseable with water is a water temperature that would be easily accessed from a water source at a residential location without having to further heat the water upon initial collection at a residential water source, such as for example, a water temperature of from about 4° C. to about 60° C., from about 20° C. to about 50° C., from about 10° C. to about 50° C., up to about 60° C., or less than about 50° C. A suitable amount of time to rinse the jammed emulsion out of a delivery device is dependent on the temperature of water. For example, a suitable amount of time can include, for example, up to 30 about minutes, up to about 20 minutes, from about 1 second to about 5 minutes, from about 5 seconds to about 1 minute, less than about 1 minute, or less than about 30 seconds. Preferably, the water rinseability of the multi-phase oral care composition at 23° C. can be up to about 10 minutes, up to about 5 minutes, up to about 1 minute, or up to 30 seconds.

The multi-phase oral care compositions can be described by its water-dispersibility according to the method disclosed herein. The water dispersibility of the multi-phase oral care composition can be measured at any suitable temperature of up to about 60° C. The water dispersibility of the multi-phase oral care composition can be greater than about 5%, greater than about 10%, greater than about 20%, greater than about 25%, or greater than about 50% of the total content of the multi-phase oral care composition, by weight or volume. Preferably, the water-dispersibility of the multi-phase oral care compositions as measured at 23° C. can be from about 20% to 100%, from about 40% to 100%, from about 60% to 100%, or greater than about 70%, by weight or volume of the total multi-phase oral care composition.

The multi-phase oral care compositions, as described herein, may comprise high internal phase emulsion, or preferably jammed oil-in-water emulsion. The jammed oil-in-water emulsions comprise hydrophobic phase, aqueous phase, active agent, and optionally emulsifier.

The multi-phase oral compositions of the present invention may be a heterogenous mixture and/or heterogenous dispersion. The multi-phase oral composition, aqueous phase, or hydrophobic phase of the present invention can be substantially free of an added adhesive, preferably substantially free of an added hydrophilic adhesive (for example hydrophilic particles that become sticky when activated by moisture) or an added hydrophilic substantivity agent, and preferably substantially free of an added hydrophilic liquid adhesive (for example glycerin). If the multi-phase oral composition of the present invention comprises an added adhesive, added hydrophilic adhesive, added hydrophilic liquid adhesive, added hydrophilic substantivity agent, added hydrophilic active releasing agent, or added hydrophilic peroxide releasing agent, it may be present in a range from about 0, 0.1, 0.2, 0.4, 1, 2, 3, 4, 5, to about 0, 0.1, 0.2, 0.4, 1, 2, 3, 4, 5, 6, 7, 8, 9, 10, 20% or any other numerical range which is narrower and which falls within such broader numerical range, as if such narrower numerical ranges were all expressly written herein; preferably less than about 20%, more preferably less than about 10%, even more preferably less than about 5%, or most preferably less than about 0.5% by weight of the multi-phase oral composition It is worth noting that stick type products may be unhygienic for repeated use inside the oral cavity due to potential contamination or bio-film build-up. Saliva or moisture may penetrate into the stick type composition when used inside the oral cavity and this may degrade the active agents especially bleaching agents such as peroxides during storage between uses; and this degradation may be further accelerated by enzymes present in saliva. Furthermore, this degradation could be most pronounced at the tip of the stick type product that comes in direct contact with the saliva or moisture inside the oral cavity, leading to diminished efficacy the next time the stick type product is used. This "contact-degrade-contact" cycle may be repeated every time the stick type product is used—leading to most if not all applications after the first application being less efficacious. It is also worth noting that stick type products may need an added active releasing agent or added peroxide releasing agent to improve the release of the active or peroxide trapped in the stick type product. In general, active releasing agents or peroxide releasing agents are hydrophilic water-soluble or water-swellable polymers or hydrophilic liquids that may provide hydration channels in the composition allowing water to penetrate the composition and allowing the active or peroxide component to leach out. However, these channels may also allow more saliva to penetrate into the composition which may accelerate the degradation of the active or peroxide.

It is worth noting that multi-phase oral compositions in liquid form may exhibit macroscopic separation of one or more components due to differences in the density of the phases. Specifically, liquid compositions that are particles or droplets dispersed in one or more liquids may exhibit macroscopic separation of one or more components due to the difference in density of the particles or droplets compared to the one or liquids they are dispersed in. Furthermore, multi-phase oral compositions in liquid form may not be substantive and run down the teeth or run out of the delivery carrier during application or during use.

Thus, in certain aspects of the multi-phase oral compositions of the present invention, the stick type product or liquid form is less preferable or not preferred.

Multi-phase oral compositions of the present invention may be a liquid, paste, cream, gel, ointment, semisolid, lotion, or any combination thereof; preferably a semisolid or a lotion. Multi-phase oral compositions of the present invention may be easy to dispense from a tube as determined by the method specified herein.

It is also worth noting that some product forms, especially stick type products, may need an added active releasing agent or added peroxide releasing agent to improve the release of the active or peroxide trapped in the stick type product. In general, active releasing agents or peroxide releasing agents are hydrophilic water-soluble or water-swellable polymers or hydrophilic liquids that may provide hydration channels in the composition allowing water to penetrate the composition and allowing the active or peroxide to leach out. An added peroxide releasing agent (such as sodium percarbonate) may help break the hydrophobic matrix as a result of micro bubbles that may be generated when the it comes in contact with water; and this disruption may enhance the release of the whitening agents, such as the hydrogen peroxide. However, it has been surprisingly discovered that the multi-phase oral compositions of the present invention can be self-releasing (for example, they release active or peroxide even without an added active releasing agent or an added peroxide releasing agent). Without wishing to be bound by theory, it is hypothesized that the multi-phase oral compositions of the present invention can be self-releasing because the aqueous phase (which may comprise active agent or bleaching agent) comprises an at least partially continuous phase that may be exposed directly to the hydrophilic tooth surface—this in turn may release the active agent or bleaching agent with little or impediment from the hydrophobic phase. Thus, the multi-phase oral composition, aqueous phase, or hydrophobic phase of the present invention can be preferably substantially free of an added active releasing agent or added peroxide releasing agent, more preferably substantially free of an added hydrophilic active releasing agent or added hydrophilic peroxide releasing agent (for example water-soluble or water-swellable polymers, hydrophilic liquids, or sodium percarbonate). In certain aspects, the multi-phase oral composition of the present invention and/or the hydrophobic phase of the present invention can be self-releasing (i.e. they release active or peroxide even without an added active releasing agent or an added peroxide releasing agent).

The multi-phase oral composition, aqueous phase, or hydrophobic phase of the present invention can be substantially free of an added wax since it may promote the formation of stick type products that are less or not preferred.

The multi-phase oral composition, aqueous phase, or hydrophobic phase of the present invention can be substantially free of ingredients, such as bleaching agents, that may react with other ingredients.

The multi-phase oral composition, aqueous phase, or hydrophobic phase of the present invention can be substantially free of ingredients, for example abrasives, silica, fumed silica, sodium tripolyphosphate, polyorganosiloxanes, condensation products of silicone resins and organosiloxanes, polymers of styrene, polymers of ethylene, polymers of propylene, polyvinylpyrrolidone, glycerin, tin fluoride, or combinations thereof, that at temperatures (for example −7° C., 4° C., 23° C., 25° C., 30° C., 40° C., 50° C., or 60° C.) and conditions that the multi-phase oral composition may be exposed to during manufacture, filling, shipping, or storage (for example 1 day, 2 days, 1 week, 2 weeks, 1 month, 2 months, 3 months, 6 months, 12 months, 18 months, or 24 months) prior to use by the consumer 1) may compromise the efficacy, comfort, usage experience, concentration of actives or bleaching agents at the tooth surface over time, active or bleaching efficiency, or compatibility between ingredients, or 2) may react with other ingredients, degrade other ingredients, cause foam or pressure to build up, decrease the substantivity of the multi-phase oral composition to teeth, cause the multi-phase oral composition to thicken or harden, or make it difficult or impractical to manually dispense a suitable dose of the multi-phase oral composition from a tube, or cause one or more components of the multi-phase oral composition to macroscopically separate.

The multi-phase oral composition, aqueous phase, or hydrophobic phase of the present invention can be substantially free of fumed silica since it may decrease the stability of the bleaching agent.

The multi-phase oral composition may be easy to manually dispense from a tube after 1 day, 2 days, 1 week, 2 weeks, 1 month, 2 months, 3 months, 6 months, 12 months, 18 months, or 24 months at −7° C., 4° C., 23° C., 25° C., 30° C., 40° C., 50° C., or 60° C.

The Product Information document (Form No. 52-1052B-01, Aug. 9, 2016) from the supplier (Dow Corning Corporation) states that BIO-PSA Standard Silicone Adhesives are supplied using heptane or ethyl acetate as a solvent—both of which have a strong odor making them unappealing to use in the oral cavity. Thus, the multi-phase oral composition, aqueous phase, or hydrophobic phase of the present invention can be substantially free of ingredients with a strong odor for example alcohols, solvents, ethyl acetate, heptane, or ingredients with a boiling point less than 99° C. The multi-phase oral composition, aqueous phase, or hydrophobic phase of the present invention can be substantially free of ingredients, for example silicone adhesives, cyclic silicones, silicones, silicone fluids, dimethicone, paraffinum liquidum, mixtures of silicones with hydrocarbons, mixtures of liquid silicones with liquid hydrocarbons, trimethylsiloxysilicate/dimethiconol crosspolymers, or combinations thereof, that at temperatures (for example −7° C., 4° C., 23° C., 25° C., 30° C., 40° C., 50° C., or 60° C.) and conditions that the multi-phase oral composition may be exposed to during manufacture, filling, shipping, or storage (for example 1 day, 2 days, 1 week, 2 weeks, 1 month, 2 months, 3 months, 6 months, 12 months, 18 months, or 24 months) prior to use by the consumer 1) may compromise the efficacy, comfort, usage experience, concentration of actives or bleaching agents at the tooth surface over time, active or bleaching efficiency, or compatibility between ingredients, or 2) may react with other ingredients, degrade other ingredients, cause foam or pressure to build up, decrease the substantivity of the multi-phase oral composition to teeth, cause the multi-phase oral composition to thicken or harden, or make it difficult or impractical to manually dispense a suitable dose of the multi-phase oral composition from a tube, or cause one or more components of the multi-phase oral composition to macroscopically separate.

The multi-phase oral composition, aqueous phase, or hydrophobic phase of the present invention can be substantially free of structure-building agents, for example amphiphilic co-polymers such as polyvinylpyrrolidone-vinyl acetate, polyvinylpyrrolidone-co-polyvinyl butyrate, or polyvinylpyrrolidone-co-polyvinyl propionate co-polymers, that may not only thicken the oral care composition, but may also drive the oral care composition toward a homogenous state or maintain the oral care composition in a homogenous state. This is because structure-building agents such as amphiphilic co-polymers 1) have at least one monomer that is hydrophilic and this may make the multi-phase oral composition more susceptible to being washed away in saliva or other liquids, or 2) may drive the oral care composition toward a homogenous state and this may decrease the concentration of actives or bleaching agents at the tooth surface over time.

Aqueous Phase

The multi-phase oral care compositions, high internal phase emulsions, or jammed oil-in-water emulsions, as described herein, comprise aqueous phase. The aqueous phase can be at least partially continuous, essentially continuous, or preferably continuous.

The multi-phase oral care composition comprises from about 0.01% to about 25%, from about 1% to about 20%, from about 2.5% to about 20%, or preferably from about 5% to about 15%, by weight or volume of the multi-phase oral care composition or jammed oil-in-water emulsion, of the aqueous phase.

The aqueous phase may also include other water-soluble solvents, such as for example, polyalkylene glycols with molecular weights from about 200 to about 20,000, humectants, or combinations thereof. Suitable humectants generally include edible polyhydric alcohols such as glycerin, sorbitol, xylitol, butylene glycol, and propylene glycol, and mixtures thereof. The aqueous phase may comprise at least about 10%, at least about 20%, or at least about 30%, of water, by weight or volume of the aqueous phase.

The multi-phase oral care compositions, as described herein, may predominantly comprise a jammed oil-in-water emulsion. However, a small portion of the multi-phase composition can comprise droplets of aqueous phase, optionally comprising an active agent. The size of the droplets of the aqueous phase, if present, may be a factor to decrease oral/topical irritation and/or tooth-sensitivity. For example, without wishing to be being bound by theory, if there are droplets of the aqueous phase present in the multi-phase oral care composition, if the size of the droplets of the aqueous phase is too large it may lead to large spots on oral/topical/tooth surfaces that are exposed to a high concentration of the active agent, which can lead to oral/topical irritation and/or tooth-sensitivity. Thus, the multi-phase oral care composition can be described by the Dv 50 equivalent-diameter, D[4,3] equivalent-diameter, or D[3,2] equivalent-diameter of the droplets of aqueous phase. For example, the Dv 50 equivalent-diameter, D[4,3] equivalent-diameter, or D[3,2] equivalent-diameter of the droplets of aqueous phase can be from about 0.1 to 5000, from about 0.1 to about 500, or from about 1 to about 50 microns.

Multi-phase oral care compositions that have a high density of large droplets of aqueous phase may lead to oral/topical irritation and/or tooth-sensitivity. Thus, it can be advantageous to minimize the density of the large droplets of aqueous phase to minimize oral/topical irritation and/or tooth-sensitivity. The method specified herein to measure the "two-dimensional density of droplets of aqueous phase" can be used to measure the droplets in two dimensions—this can be done using a light microscope by counting the number of droplets larger than a specified size (at the focal plane). For example, the two-dimensional density of droplets of aqueous phase larger than 10000 square microns found in 1 cm$^2$ of the multi-phase oral care composition can be up to about 1, up to about 0.1, or preferably 0. Preferably, the multi-phase oral care composition can be free of or substantially free of droplets of aqueous phase with a cross-sectional area of up to about 1000, 3000, 10000, 20000, or 50000 square microns.

The multi-phase oral compositions may comprise an aqueous solution of a bleaching agent, such as hydrogen peroxide, optionally including emulsifier.

Hydrophobic Phase

The multi-phase oral care compositions or high internal phase emulsions, preferably jammed oil-in-water emulsions, as described herein, comprise a hydrophobic phase. The hydrophobic phase is at least partially discontinuous, essentially discontinuous, or preferably discontinuous.

The present invention comprises a safe and effective amount of a hydrophobic phase. The multi-phase oral care composition comprises from about 75% to about 99%, from about 80% to about 97.5%, greater than about 80%, greater than about 90%, or preferably, from about 85% to about 95%, by weight or volume of the multi-phase oral care composition or jammed oil-in-water emulsion, of the hydrophobic phase.

The density of the hydrophobic phase used in the multi-phase oral care compositions, as described herein, may be in the range of from about 0.8 g/cm$^3$ to about 1.0 g/cm$^3$, from about 0.85 g/cm$^3$ to about 0.95 g/cm$^3$, or about 0.9 g/cm$^3$, or any other numerical range, which is narrower, and which falls within such broader numerical range, as if such narrower numerical ranges were all expressly written herein.

The hydrophobic phase can comprise a non-toxic oil, such as non-toxic edible oil. The hydrophobic phase can comprise non-toxic edible oils, saturated or unsaturated fatty alcohols, aliphatic hydrocarbons, long chain triglycerides, fatty esters, and combinations thereof. The hydrophobic phase may also comprise silicones, polysiloxanes, and mixtures thereof. The hydrophobic phase may be preferably selected from mineral oil, petrolatum, and combinations thereof. A preferred petrolatum is white petrolatum. Other examples of petrolatum include Snow White Pet-C from Calumet Specialty Products (Indianapolis, Ind.), G-2191 from Sonneborn (Parsippany, N.J.), G-2218 from Sonneborn, G-1958 from Sonneborn, G-2180 from Sonneborn, Snow White V28 EP from Sonneborn, and Snow White V30 from Sonneborn, G-2494 from Sonneborn, and mixtures thereof.

The multi-phase oral compositions may comprise discontinuous phase, which can comprise mineral oil. The multi-phase oral compositions may comprise hydrophobic phase, which can comprise mineral oil as a hydrophobic phase.

The aliphatic hydrocarbons can comprise from about 10, 12, 14, or 16 to about 16, 18, 20, 22, 24, 26, 28, 30, 36, 40 carbon atoms such as decane, 2 ethyldecane, tetradecane, isotetradecane, hexadecane, eicosane, and combinations thereof. Long chain triglycerides can comprise vegetable oils, fish oils, animal fats, hydrogenated vegetable oils, partially hydrogenated vegetable oils, semi-synthetic triglycerides, synthetic triglycerides, and mixtures thereof. Fractionated, refined or purified oils of these types can also be used. Examples of long chain triglyceride-containing oils include almond oil; babassu oil; borage oil; black currant seed oil; canola oil; castor oil; coconut oil; corn oil; cottonseed oil; emu oil; evening primrose oil; flax seed oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; a mixture of hydrogenated cottonseed oil and hydrogenated castor oil; partially hydrogenated soybean oil; a mixture of partially hydrogenated soybean oil and partially hydrogenated cottonseed oil; glyceryl trioleate; glyceryl trilinoleate; glyceryl trilinolenate; a Ω3-polyunsaturated fatty acid triglyceride containing oil; and mixtures thereof. The long chain triglyceride containing oils may be selected from the group consisting of corn oil, olive oil, palm oil, peanut oil, safflower oil, sesame oil, soybean oil, castor oil, linseed oil, rape oil, rice bran oil, coconut oil, hydrogenated castor oil; partially hydrogenated soybean oil; glyceryl trioleate; glyceryl trilinoleate; a Ω3-polyunsaturated fatty acid triglyceride containing oil; and combinations thereof.

Saturated or unsaturated fatty alcohols may have from about 6 to about 20 carbon atoms, cetearyl alcohol, lauryl alcohol, and mixtures thereof. For example, Lipowax (Cetearyl Alcohol and Ceteareth-20) are supplied and manufactured by Lipo Chemical.

General information on silicones including silicone fluids, gums and resins, as well as the manufacture of silicones, can be found in Encyclopedia of Polymer Science and Engineering, Volume 15, Second Edition, pp 204-308, John Wiley & Sons Inc. 1989 and Chemistry and Technology of Silicones, Walter Noll, Academic Press Inc, (Harcourt Brue Javanovich, Publishers, New York), 1968, pp 282-287 and 409-426.

The multi-phase oral care compositions, aqueous phase, or hydrophobic phase may be substantially free of ingredients, for example acids and/or alcohols, combinations of mineral oil and ethylene/propylene/styrene copolymer and/or butylene/ethylene/styrene copolymer, certain bleaching agents, fumed silica, polyorganosiloxanes, copolymer condensation products of silicone resins and polydiorganosiloxanes, or combinations thereof, silicones, dimethicone, paraffinum liquidum, trimethylsiloxysilicate/dimethiconol crosspolymer, or combinations thereof, molecules with double or triple covalent bonds between adjacent carbon atoms, molecules with styrene groups, that at temperatures (for example −7° C., 4° C., 23° C., 25° C., 30° C., 40° C., 50° C., or 60° C.) and conditions that the multi-phase oral care composition may be exposed to during manufacture, filling, shipping, or storage (for example 1 day, 2 days, 1 week, 2 weeks, 1 month, 2 months, 3 months, 6 months, 12 months, 18 months, or 24 months) prior to use by the consumer that 1) may compromise the efficacy, comfort, usage experience, concentration of actives or bleaching agents at the tooth surface over time, active or bleaching efficiency, or compatibility between ingredients, or 2) may react with other ingredients or degrade other ingredients or may cause foam or pressure to build up in the package or container in which the multi-phase oral care composition is stored. The multi-phase oral care compositions may comprise less than 0.001% by weight of the composition, of any of the compounds recited in this paragraph, preferably multi-phase oral care compositions do not comprise acids and/or alcohols. Without being bound by a theory it is believed that the decrease in surface tension produced by alcohol may decrease the retention time of the aqueous phase at the tooth surface, thereby decreasing the efficacy of the oral care actives. The presence of acids might contradict with the actives and/or may produce negative side effects as the tooth surface such as hypersensitivity etc. Thus, the multi-phase oral care compositions can be free of acids, free of alcohols, or free of a mixture thereof.

The hydrophobic phase is in predominant or majority proportion relative to the aqueous phase present in the multi-phase oral care composition. As used herein "predominant proportion" means that the percent by weight or volume of the hydrophobic phase of the multi-phase oral care composition is in excess relative to the percent by weight or volume of the aqueous phase of the multi-phase oral care composition.

The size and number of regions of hydrophobic phase may affect the amount of oral/topical irritation and/or tooth sensitivity imparted by the multi-phase oral composition, or stability of the multi-phase oral composition. The multi-phase oral care composition can be described in terms of its "two-dimensional density of regions of hydrophobic phase" measured using the method specified herein. For example, the two-dimensional density of regions of hydrophobic phase larger than about 10, 100, 1000, or preferably 10000 μm$^2$ found in 1 cm$^2$ of the multi-phase oral care composition can be from about 1 to about 1,000,000, from about 10 to 100,000, or preferably, from about 100 to about 10,000.

Similarly, the multi-phase oral care composition can be described by the Dv 50 equivalent-diameter, D[4,3] equivalent-diameter, or D[3,2] equivalent-diameter of regions of the hydrophobic phase. For example, the Dv 50 equivalent-diameter, D[4,3] equivalent-diameter, or D[3,2] equivalent-diameter of regions of the hydrophobic phase can be from about 0.1 to 5000, from about 0.1 to about 500, or preferably from about 1 to about 50 microns.

The hydrophobic phase may be inert or at least partially inert. The hydrophobic phase may interact, not interact, or only minimally interact with the other ingredients of the multi-phase oral care compositions, such as for example, flavors, thickeners, or the active agents.

A suitable hydrophobic phase for the compositions as disclosed herein may have an octanol/water partition coefficient (log $P_{ow}$) of greater than about 2, 3, 4, 5, or greater than about 5.5, as determined by OECD 117, Partition Coefficient (n-octanol/water), HPLC method. Additionally, the hydrophobic phase can show a log $P_{ow}$ greater than about 6, as determined by OECD 117.

Without being bound by theory, the freezing point, melting point or drop melting point as measured according to ASTM method D127, or congealing point as measured according to ASTM method D938, or pour point as measured according to ASTM D97 of the hydrophobic phase may be a factor to ensure that the composition: 1) is substantive and does not run down the teeth or run out of the delivery carrier during application or during use, 2) inhibits macroscopic separation of one or more of the components of the multi-phase oral care composition at a particular operating, handling, storage, or manufacturing temperature, such as, for example, 4° C., 23° C., 25° C., 30° C., 40° C., 50° C., or 60° C., for a particular period of time, such as, for example, 1 day, 2 days, 1 week, 2 weeks, 1 month, 2 months, 3 months, 6 months, 12 months, 18 months, or 24 months, prior to use by the consumer, or 3) releases an effective amount of the bleaching agent or active agent during use.

Specifically, if the freezing point, melting point or drop melting point as measured according to ASTM method D127, or congealing point as measured according to ASTM method D938, or pour point as measured according to ASTM D97 of the hydrophobic phase is too low, the multi-phase oral care composition may not be substantive and run down the teeth or run out of the delivery carrier during application or during use; or the multi-phase oral care composition may exhibit macroscopic separation of one or more of the components of the multi-phase oral care composition at temperatures and conditions experienced prior to use by consumer, as described herein. In contrast, if the freezing point, melting point or drop melting point as measured according to ASTM method D127, or congealing point as measured according to ASTM method D938, or pour point as measured according to ASTM D97 of the hydrophobic phase is too high, the multi-phase oral care composition may not release an effective amount of the bleaching agent or active agent during use.

The freezing point, melting point or drop melting point as measured according to ASTM method D127, or congealing point as measured according to ASTM method D938, or pour point as measured according to ASTM D97 of the hydrophobic phase may be from about −100° C. to about 100° C., −50° C. to about 23° C., or preferably from about −50° C. to about 0° C. The freezing point, melting point or drop melting point as measured according to ASTM method D127, or congealing point as measured according to ASTM method D938, or pour point as measured according to ASTM D97 of the hydrophobic phase may be less than about 40° C., 30° C., 23° C., 10° C., 0° C., −10° C., −20° C., −30° C., 40° C., −50° C., or −100° C. or any other numerical range, which is narrower, and which falls within such broader numerical range, as if such narrower numerical ranges were all expressly written herein.

Without being bound by theory, the cone penetration consistency value, kinematic viscosity, Brookfield Viscosity, yield stress, shear storage modulus, shear loss modulus, ratio of the shear storage modulus to the shear loss modulus, or slide flow distance of the hydrophobic phase alone or the multi-phase oral care composition in total may be a factor to ensure that the multi-phase oral care composition: 1) is substantive and does not run down the teeth or run out of the delivery carrier during application or during use, 2) inhibits macroscopic separation of one or more of the components of the multi-phase oral care composition at a particular operating, handling, storage, or manufacturing temperature, such as, for example, 4° C., 23° C., 25° C., 30° C., 40° C., 50° C., or 60° C., for a particular period of time, such as, for example, 1 day, 2 days, 1 week, 2 weeks, 1 month, 2 months, 3 months, 6 months, 12 months, 18 months, or 24 months, prior to use by the consumer, or 3) releases an effective amount of the bleaching agent or active agent during use.

Specifically, if the cone penetration consistency value or the slide flow distance of the hydrophobic phase or the multi-phase oral care composition is too high, or the kinematic viscosity, Brookfield Viscosity, yield stress, shear storage modulus, shear loss modulus, or ratio of the shear storage modulus to the shear loss modulus is too low, the multi-phase oral care composition may not be substantive and run down the teeth or run out of the delivery carrier during application or during use; or the multi-phase oral care composition may exhibit macroscopic separation of one or more of the components of the multi-phase oral care composition at temperatures and conditions experienced prior to use by consumer, as described herein. In contrast, if the cone penetration consistency value or the slide flow distance of the hydrophobic phase or the multi-phase oral care composition is too low, or the kinematic viscosity, Brookfield Viscosity, yield stress, shear storage modulus, shear loss modulus, or ratio of the shear storage modulus to the shear loss modulus of the hydrophobic phase or the multi-phase oral care composition is too high, the multi-phase oral care composition may not release an effective amount of the bleaching agent or active agent during use.

It is worth noting that, in general: 1) hydrophobic phases that have a low cone penetration consistency value tend to form stick type products, especially when combined with powder ingredients including active agents or bleaching agents that are ground or manufactured to minimize particle size e.g. by micronization, 2) hydrophobic phases that are rich in waxes tend to have a low cone penetration consistency value, 3) stick type products tend to have a low cone penetration consistency value, 4) hydrophobic phases that have a low cone penetration consistency value (that tend to form stick type products) may also inhibit the release of the bleaching agent or active agent, and 5) stick type products (that tend to have a low cone penetration consistency value) may also inhibit the release of the bleaching agent or active agent. It is also worth noting that multi-phase oral compositions that have a low cone penetration consistency value or multi-phase oral compositions whose hydrophobic phase has a low cone penetration consistency value may be difficult or impractical to manually dispense a suitable dose of the multi-phase oral composition from a tube.

Thus, in certain aspects, the cone penetration consistency value of the hydrophobic phase or multi-phase oral compositions may have a cone penetration consistency value as measured according ASTM method D937 more than about 600, more than about 500, or more than about 400.

The Brookfield Viscosity of the hydrophobic phase or multi-phase oral care composition can be from about 10 cPs to about 5,000,000 cPs, from about 1,000 cPs to about 500,000 cPs, from about 1,000 cPs to about 100,000 cPs, or preferably from about 1,000 cPs to about 50,000 cPs as measured at 23° C. according to the method specific herein. The Brookfield Viscosity of the multi-phase oral care composition can be at least 2, 5, 10, 25, 50, 100, 200, and/or 250 times greater than the initial viscosity of the aqueous phase and/or the hydrophobic phase.

The kinematic viscosity of the hydrophobic phase or multi-phase oral care composition can be from about 1 $mm^2/s$ to about 10,000 $mm^2/s$, from about 1 $mm^2/s$ to about 1,000 $mm^2/s$, or preferably from about 5 $mm^2/s$ to about 500 $mm^2/s$ as measured by ASTM D 445 at 40° C.

The ratio of the shear storage modulus to the shear loss modulus of the multi-phase oral care composition can be from about 0.01 to about 2, from about 0.5 to 2, or preferably from about 1 to about 2.

The slide flow distance of the multi-phase oral care composition or hydrophobic phase can be up to about 30 mm, up to about 20 mm, up to about 10 mm, or preferably from about 0 mm to about 10 mm as measured according to the method specified herein.

The yield stress of the multi-phase oral care composition can be from about 2 Pa to about 2000 Pa, from about 2 Pa to about 500 Pa, or preferably from about 2 Pa to about 250 Pa as measured according to the method specified herein at 23° C.

Active Agents

The present multi-phase oral care compositions or high internal phase emulsions preferably jammed oil-in-water emulsions, as described herein, comprise a safe and effective amount of one or more active agents, preferably oral care active agents.

One or more active agents can be dissolved, at least partially dissolved, or dispersed in the aqueous phase, hydrophobic phase, or combinations thereof. One or more active agents can be in the aqueous phase and one or more active agents can be in the hydrophobic phase, depending on whether the active agent is more soluble in the aqueous or hydrophobic phase.

The oral care active agent can comprise one or more active agents, such as an anti-caries agent, an anti-tartar agent, a remineralization agent, a wound healing agent, an anti-inflammatory agent, an antibacterial agent, a metal ion source, an anti-glycolytic agent, an amino acid, a probiotic, a prebiotic, a postbiotic, a polyphosphate, a buffer, anti-sensitivity agent, a bleaching agent, or combinations thereof.

Many of the oral care active agents can have more than one use, which can allow specific oral care actives to fall within more than one category. For example, a fluoride salt, such as stannous fluoride, can be an anti-caries agent, a metal ion source, and an anti-bacterial agent. Stannous fluoride, and other similar compounds, would only need to be included once to achieve all of the particular benefits associated with its use. A preferred oral care active agent is a bleaching agent. For convenience, specific reference may be made to a bleaching agent in many instances throughout the specification, however, any other oral care active agent can be used in place of the bleaching agent.

The oral care active agent can comprise an anti-caries agent. Suitable anti-caries agents include any compound that has anti-caries activity. Some examples include fluoride ion sources, metal ion sources, sugar alcohols, bioglass containing compounds, and/or amino acids. Fluoride ion sources can include sodium fluoride, potassium fluoride, titanium fluoride, hydrofluoric acid, amine fluoride, sodium monofluorophosphate, stannous fluoride, and/or other suitable fluoride ion sources.

The present compositions may comprise a metal ion source that provides stannous ions, zinc ions, copper ions, or mixtures thereof. The metal ion source can be a soluble or a sparingly soluble compound of stannous, zinc, or copper with inorganic or organic counter ions. Examples include the fluoride, chloride, chlorofluoride, acetate, hexafluorozirconate, sulfate, tartrate, gluconate, citrate, malate, glycinate, pyrophosphate, metaphosphate, oxalate, phosphate, carbonate salts and oxides of stannous, zinc, and copper. Stannous, zinc and copper ions are derived from the metal ion source (s) can be found in the multi-phase oral care composition an effective amount to provide an oral care benefit or other benefits. Stannous, zinc and copper ions have been found to help in the reduction of gingivitis, plaque, sensitivity, and improved breath benefits. An effective amount is defined as from at least about 500 ppm to about 20,000 ppm metal ion of the total composition, preferably from about 2,000 ppm to about 15,000 ppm. More preferably, metal ions can be present in an amount from about 3,000 ppm to about 13,000 ppm and even more preferably from about 5,000 ppm to about 10,000 ppm. This is the total amount of metal ions (stannous, zinc, copper and mixtures thereof) that is present in the compositions for delivery to the tooth surface.

Other metal ion sources can include minerals and/or calcium containing compounds, which can lead to remineralization, such as, for example, sodium iodide, potassium iodide, calcium chloride, calcium lactate, calcium phosphate, hydroxyapatite, fluoroapatite, amorphous calcium phosphate, crystalline calcium phosphate, sodium bicarbonate, sodium carbonate, calcium carbonate, oxalic acid, dipotassium oxalate, monosodium monopotassium oxalate, casein phosphopeptides, and/or casein phosphopeptide coated hydroxy apatite.

Sugar alcohols can include xylitol, sorbitol, erythritol, glycerin, or any other sugar alcohol that can provide an anti-caries benefit.

Bioglass containing compounds include one or more of $SiO_2$, $CaO$, $Na_2O$, $P_2O_5$, $CaF_2$, $B_2O_3$, $K_2O$, $MgO$, as described in U.S. Pat. No. 5,735,942.

Suitable amino acids include histidine, isoleucine, leucine, lysine, methionine, phenylalanine, threonine, tryptophan, valine, alanine, asparagine, aspartic acid, and glutamic acid, arginine, cysteine, glutamine, tyrosine, glycine, ornithine, proline, and serine, peptides, calcium salts of amino acids, and/or peptides.

The oral care active agent can comprise a healing agent that promotes or enhances the healing or regenerative process. Such healing agents may comprise hyaluronic acid or salts, glucosamine or salts, allantoin, curcumin, D panthenol, niacinamide, ellagic acid, flavanoids (including fisetin, querctin, luteolin, apigenin), vitamin E, ubiquinone, or mixtures thereof. The healing agent can also include resolvins, such as eicosapentaenoic acid (EPA) and docosahexaenoic acid (DHA), as well as docosapentaenoic acid (DPA) clupanodonic acid, Resolvin D's RvD1 (7S,8R,17S-trihydroxy-DHA), RvD2 (7S,16R,17S-trihydroxy-DHA), RvD3 (4S, 7R,17S-trihydroxy-DHA), RvD4 (4S,5,17S-trihydroxy-DHA), RvD5 (7S,17S-dihydroxy-DHA), and RvD6 (4S, 17S-dihydroxy-DHA) and Resolvin E's: RvE1 (5S,12R, 18R-trihydroxy-EPA), 18S-Rv1 (5S,12R,18S-trihydroxy-EPA), RvE2 (5S,18R-dihydroxy-EPA), and RvE3 (17R, 18R/S-dihydroxy-EPA), retinol, tranexamic acid, glycine, retinol, amino acids, niacinamide, and/or human growth factors.

The oral care active agent can comprise one or more probiotics selected from *Lactobacillus reuteri* ATCC 55730; *Lactobacillus salivarius* strain TI12711 (LS 1); *Lactobacillus paracasei* ADP-1; *Streptococcus salivarius* K12; *Bifidobacterium* DN-173 010; Filtrate of *L. paracasei* strain (pro-t-Action™); *S. Oralis* KJ3, *S. rattus* JH145, *S. uberis* KJ2; *Lactobacillus, reuteri* Prodentis; *Lactobacillus salivarius* LS1; *Lactobacillus paracasei*; *Lactobacillus paracasei* ADP1; *Streptococcus salivarius* M18, K12 or BLIS K12 and BLIS M18; *Bacillus Amyloliquefaciens*; *Bacillus Clausii*; *Bacillus Coagulans*; *Bacillus Subtilis*; *Bacillus subtilis*: E-300; *Bifidobacterium Animalis*; *Bifidobacterium* B6; *Bifidobacterium Bifidum*; *Bifidobacterium Breve* (Bb-03); *Bifidobacterium* DN-173 010; *Bifidobacterium* GBI 30 6068; *Bifidobacterium infantis*; *Bifidobacterium Lactis*; *Bifidobacterium lactis* Bb-12; *Bifidobacterium Longum*; *Bifidobacterium Thermophilum*; *Enterococcus Faecalis*; *Enterococcus Faecium*; *Enterococcus Faecium* NCIMB 10415; *Enterococcus* LAB SF 68; *Lactobacilli reuteri* ATCC 55730 and ATCC PTA 5289; *Lactobacilli reuteri* ATCC 55730 and ATCC PTA 5289 (10:1); *Lactobacillus Acidophilus*; *Lactobacillus acidophilus* ATCC 4356 and *Bifidobacterium bifidum* ATCC 29521; *Lactobacillus acidophilus*; *Bifidobacterium longum*; *Bifidobacterium bifidum*; *Bifidobacterium lactis*; *Lactobacillus Brevis*; *Lactobacillus Casei* (subsp. *Casi*); *Lactobacillus casei* Shirota; *Lactobacillus* Confusus; *Lactobacillus* crispatus YIT 12319; *Lactobacillus Curvatus*; *Lactobacillus Delbrueckii* Ssp. *Bulgaricus* PXN 39; *Lactobacillus Fermentum*; *Lactobacillus fermentum* YIT 12320; *Lactobacillus* Gasseri; *Lactobacillus* gasseri YIT 12321; *Lactobacillus Helveticus*; *Lactobacillus* Johnsonii; *Lactobacillus Kimchii*; *Lactobacillus Lactis* L1A; *Lactobacillus Paracasei* (Lpc37); *Lactobacillus paracasei* GMNL-33; *Lactobacillus Pentosus*; *Lactobacillus plantarum*; *Lactobacillus Plantarum*; *Lactobacillus* Protectus; *Lactobacillus Reuteri*; *Lactobacillus reuteri* ATCC 55730; *Lactobacillus reuteri* SD2112 (ATCC55730); *Lactobacillus Rhamnosus* (GG); *Lactobacillus rhamnosus* GG; *Lactobacillus rhamnosus* GG; *L. rhamnosus* LC705; *Propionibacterium freudenreichii* ssp; *shermanii* JS; *Lactobacillus rhamnosus* L8020; *Lactobacillus rhamnosus* LB 21; *Lactobacillus Salivarius*; *Lactobacillus salivarius* WB21; *Lactobacillus Sporogenes*; *Lactococcus Lactis* Ssp Diacetylactis; *Lactococcus Lactis* Ssp. *Lactis*; *Pediococcus Acidilactici*; *Pediococcus Pentosaceus*; *Saccharomyces Boulardii*; *Saccharomyces Cerevisiae*; Strep. *uberis KJ*2sm; Strep. *oralis* KJ3sm; trep. *rattus* JH145; *Streptococcus mitis* YIT 12322; *Streptococcus Oralis* KJ3; *Streptococcus Rattus* JH145; *Streptococcus Salivarius* (BLIS K12 or BLIS M18); *Streptococcus salivarius* K12; *Streptococcus Thermophilus*; *Streptococcus Uberis* KJ2; *Thermus thermophiles*; *Weissella cibaria* CMS2; *Weissella cibaria* CMS3; and *Weissella cibaria* CMU.

Probiotics can be used in the multi-phase oral care compositions of the present invention to promote positive oral health effects, such as reduce caries and plaque, promote gum health, improve breath, and promote whitening. The efficacy of probiotics in the multi-phase oral care compositions can be determined by measuring one or more of the following: reduction of the levels of salivary mutans streptococci; reduction of gingival crevicular fluid; reduction of periodontal pathogens (*C. rectus* and *P. gingivitis*) in subgingival plaque; decreased counts of yeast; decreased prevalence of oral *candida*; reduction of oral volatile sulfur compound (VSC) levels; and reduction of TNF-α and IL-8 production. Without being limited to theory it is believed that one or more of the above positive oral health effects may be achieved through the production of bacterial toxins, which remove or reduce certain types of bacteria in the oral cavity; further more one or more of the above positive oral health effects may be achieved through bacterial production of one or more enzymes that inhibit the production of or dissolves/ loosens biofilms or sticky deposits that can lead to oral health problems.

As the present multi-phase oral care composition can be directed to bleaching the tooth surface and removing or decreasing the stain attached thereto, a safe and effective amount may be added of at least one anticalculus agent to the compositions as disclosed herein. The multi-phase oral care composition may include from about 0.01% to about 40%, from about 0.1% to about 25%, from about 4.5% to about 20%, or from about 5% to about 15%, by weight of the multi-phase oral care composition or any other numerical range, which is narrower, and which falls within such broader numerical range, as if such narrower numerical ranges were all expressly written herein, of anticalculus agent. The anticalculus agent may also be compatible with the other components of the multi-phase oral care composition, in preferred embodiments the whitening agent. The anticalculus agent may be selected from the group consisting of polyphosphates and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof, wherein the mentioned salts can be alkali metal salts. In certain aspects anticalculus agents used in the present multi-phase oral care composition also show a stabilizing effect to the bleaching agents, such as pyrophosphates, polyphosphates, polyphophonates and mixtures thereof.

For example, the anticalculus agent may be a polyphosphate. A polyphosphate is generally understood to comprise two or more phosphate molecules arranged primarily in a linear configuration, although some cyclic derivatives may be present. Linear polyphosphates correspond to $(X\ PO_3)_n$ where n is about 2 to about 125, wherein preferably n is greater than 4, and X is for example sodium, potassium, etc. For $(X\ PO_3)_n$ when n is at least 3 the polyphosphates can be glassy in character. Counter-ions for these phosphates may be the alkali metal, alkaline earth metal, ammonium, $C_2$-$C_6$ alkanolammonium and salt mixtures. Polyphosphates are generally employed as their wholly or partially neutralized water-soluble alkali metal salts such as potassium, sodium, ammonium salts, and mixtures thereof. The inorganic polyphosphate salts include alkali metal (e.g. sodium) tripolyphosphate, tetrapolyphosphate, dialkyl metal (e.g. disodium) diacid, trialkyl metal (e.g. trisodium) monoacid, potassium hydrogen phosphate, sodium hydrogen phosphate, and alkali metal (e.g. sodium) hexametaphosphate, and mixtures thereof. Polyphosphates larger than tetrapolyphosphate usually occur as amorphous glassy materials, such as those manufactured by FMC Corporation which are commercially known as Sodaphos (n≈6), Hexaphos (n≈13), Glass H (n≈21), and mixtures thereof. If present, the present compositions will typically comprise from about 0.5% to about 20%, from about 4% to about 15%, or preferably from about 6% to about 12%, by weight of the composition of polyphosphate.

The pyrophosphate salts useful in the present compositions include, alkali metal pyrophosphates, di-, tri-, and mono-potassium or sodium pyrophosphates, dialkali metal pyrophosphate salts, tetraalkali metal pyrophosphate salts, and mixtures thereof. For example, the pyrophosphate salt is selected from the group consisting of trisodium pyrophosphate, disodium dihydrogen pyrophosphate ($Na_2H_2P_2O_7$), dipotassium pyrophosphate, tetrasodium pyrophosphate ($Na_4P_2O_7$), tetrapotassium pyrophosphate ($K_4P_2O_7$), and mixtures thereof, wherein tetrasodium pyrophosphate is preferred. Tetrasodium pyrophosphate may be the anhydrous salt form or the decahydrate form, or any other species stable in solid form in the present compositions. The salt is in its solid particle form, which may be its crystalline and/or amorphous state, with the particle size of the salt preferably being small enough to be aesthetically acceptable and readily soluble during use. The level of pyrophosphate salt in the present compositions may be from about 1.5% to about 15%, in particular from about 2% to about 10%, and more particular from about 3% to about 8%, by weight of the composition.

The phosphate sources, including but are not limited to, polyphosphates and pyrophosphates, are described in more detail in Kirk & Othmer, *Encyclopedia of Chemical Technology*, Fourth Edition, Volume 18, Wiley-Interscience Publishers (1996), pages 685-707.

Polyolefin phosphonates include those wherein the olefin group contains 2 or more carbon atoms. Polyvinylphosphonates include polyvinylphosphonic acid. Diphosphonates and salts thereof include azocycloalkane-2,2-diphosphonic acids and salts thereof, ions of azocycloalkane-2,2-diphosphonic acids and salts thereof (such as those which the alkane moiety has five, six or seven carbon atoms, in which the nitrogen atom is unsubstituted or carries a lower alkyl substitutent, e.g. methyl), azocyclohexane-2,2-diphosphonic acid, azocyclopentane-2,2-diphosphonic acid, N-methyl-azocyclopentane-2,3-diphosphonic acid, EHDP (ethanehydroxy-1,1,-diphosphonic acid), AHP (azocycloheptane-2,2-diphosphonic acid, a.k.a. 1-azocycloheptylidene-2,2-diphosphonic acid), ethane-1-amino-1,1-diphosphonate, dichloromethane-diphosphonate, etc. Phosphonoalkane carboxylic acid or their alkali metal salts include PPTA (phosphonopropane tricarboxylic acid), PBTA (phosphonobutane-1,2,4-tricarboxylic acid), each as acid or alkali metal salts.

In addition, antimicrobial antiplaque agents may also be present in the present compositions. Such agents may include, but are not limited to, triclosan, hops acids from hops extracts, such as hops alpha acids, including, humulone, adhumulone, cohumulone, posthumulone, prehumulon, and combinations thereof, or hops beta acids, including, lupulone, adlupulone, colupulone, and combinations thereof, 5-chloro-2-(2,4-dichlorophenoxy)-phenol, as described in The Merck Index, 11th ed. (1989), pp. 1529 (entry no. 9573) in U.S. Pat. No. 3,506,720, and in European Patent Application No. 0,251,591; chlorhexidine (Merck Index, no. 2090), alexidine (Merck Index, no. 222; hexetidine (Merck Index, no. 4624); sanguinarine (Merck Index, no. 8320); benzalkonium chloride (Merck Index, no. 1066); salicylanilide (Merck Index, no. 8299); domiphen bromide (Merck Index, no. 3411); cetylpyridinium chloride (CPC) (Merck Index, no. 2024; tetradecylpyridinium chloride (TPC); N-tetradecyl-4-ethylpyridinium chloride (TDEPC); octenidine; delmopinol, octapinol, and other piperidino derivatives; In addition there may be effective antimicrobial amounts of essential oils and combinations thereof for example citral, geranial, and combinations of menthol, eucalyptol, thymol and methyl salicylate; antimicrobial metals and salts thereof for example those providing zinc ions, stannous ions, copper ions, and/or mixtures thereof; bisbiguanides, or phenolics; antibiotics such as augmentin, amoxicillin, tetracycline, doxycycline, minocycline, and metronidazole; and analogs and salts of the above antimicrobial antiplaque agents and/or anti-fungals such as those for the treatment of *Candida albicans*. If present, these agents generally are present in a safe and effective amount for example from about 0.1% to about 5% by weight of the present compositions.

The oral care active agent can comprise one or more anti-inflammatory agents. Such anti-inflammatory agents may include, but are not limited to, non-steroidal anti-inflammatory agents such as aspirin, ketorolac, flurbiprofen, ibuprofen, naproxen, indomethacin, aspirin, ketoprofen, piroxicam and meclofenamic acid, COX-2 inhibitors such as valdecoxib, celecoxib and rofecoxib, and mixtures thereof. If present, the anti-inflammatory agents generally comprise from about 0.001% to about 5% by weight of the compositions.

The oral care active agent can comprise one or more minerals. The minerals may improve the teeth and the tooth surface and thus can be included with the compositions as disclosed herein. Suitable minerals include e.g. calcium, phosphorus, fluoride, zinc, manganese, potassium and mixtures thereof. These minerals are e.g. disclosed in Drug Facts and Comparisons (loose leaf drug information service), Wolters Kluer Company, St. Louis, Mo., ©1997, pp 10-17.

Suitable bleaching agents can comprise agents that provide bleaching effects, stain bleaching effects, stain removal effects, stain color change effects or any other effect, which change, or brighten tooth color. For example, bleaching agents can comprise a source of peroxide radicals. In addition, bleaching agents may include peroxides, metal chlorites, perborates, percarbonates, peroxyacids, persulfates, compounds that form the preceding compounds in situ, and combinations thereof. Examples of peroxide compounds include hydrogen peroxide, urea peroxide, calcium peroxide, carbamide peroxide, and mixtures thereof. In certain embodiments, the bleaching agent may be hydrogen peroxide ($H_2O_2$). Suitable metal chlorites include calcium chlorite, barium chlorite, magnesium chlorite, lithium chlorite, sodium chlorite, potassium chlorite, and mixtures thereof. Additional bleach agents also include hypochlorite (such as metal hypochlorite) and chlorine dioxide. Persulfates include salts of peroxymonosulfate, peroxydisulfate and mixtures thereof. The oral care active agent, such as a bleaching agent, can be introduced into the multi-phase oral care composition or oil-in-water emulsion as an aqueous solution, as a solid, or as a liquid. Preferably, the active agent is introduced into the multi-phase oral care composition as an aqueous solution.

The multi-phase oral care composition or high internal phase emulsion preferably jammed oil-in-water emulsion can comprise from about 0.01% to about 10%, from about 0.05% to about 5%, from about 0.01% to about 1%, 0.01% to less than 1%, from about 1% to about 10%, greater than 1% to about 10%, from about 3% to about 20%, or preferably from about 0.5% to about 5%, by weight of the multi-phase oral care composition or jammed oil-in-water emulsion, of the active agent, such as a bleaching agent.

The aqueous phase of can comprise from about 5% to about 67%, from about 10% to about 50%, or preferably, from about 15% to about 50%, by weight of the aqueous phase, of the active agent, such as a bleaching agent Surprisingly, bleaching agents can be significantly effective when used even at the low levels in the multi-phase oral care compositions as disclosed herein, which may be in the form of jammed oil-in-water emulsions.

The multi-phase oral care compositions or jammed oil-in-water emulsions, as described herein, can deliver a high ratio of the concentration in weight percent of bleaching agent present in the aqueous phase to the concentration in weight percent of bleaching agent present in the overall multi-phase oral care composition, as they have a high concentration in weight percent of bleaching agent present in the aqueous phase combined with a relatively low concentration in weight percent of bleaching agent present in the overall multi-phase oral care composition. Without being bound by theory, this surprising combination of seemingly contradictory parameters in the present invention delivers the bleaching agent to the tooth surface with a high driving force even when the overall concentration or amount of bleaching agent delivered to the tooth surface is low. As a result, the high driving force delivers a surprisingly high level of bleaching efficacy and/or bleaching speed; while the low overall concentration or low amount of bleaching agent delivered to the tooth surface may help reduce tooth sensitivity The ratio of the concentration in weight percent of bleaching agent present in the aqueous phase to the concentration in weight percent of bleaching agent present in the overall multi-phase oral care composition may be from about 67000, 50000, 35000, 20000, 17500, 10000, 5000, 3500, 2000, 1750, 1160, 1000, 875, 700, 580, 500, 430, 400, 380, 350, 200, 175, 111, 110, 105, 100, 90, 80, 70, 60, 50, 40, 30, 20, 15, 10, or 5 to about 67000, 50000, 35000, 20000, 17500, 10000, 5000, 3500, 2000, 1750, 1160, 1000, 875, 700, 580, 500, 430, 400, 380, 350, 200, 175, 111, 110, 105, 100, 90, 80, 70, 60, 50, 40, 30, 20, 15, 10, or 5 or any other numerical range, which is narrower and which falls within such broader numerical range, as if such narrower numerical ranges were all expressly written herein.

The bleaching agents of the present invention may be stabilized against degradation by the shielding effect of the hydrophobic phase. For example, after 180 days of storage at 30° C. following formulation, multi-phase oral care compositions of the present invention can comprise at least about 10% of the initial amount of hydrogen peroxide they were formulated with. Additionally, at least about 25% of the initial amount of hydrogen peroxide, at least about 50% of the initial amount of hydrogen peroxide, or at least about 75% of the initial amount of hydrogen peroxide may be present after 180 days storage of the composition at 30° C.

The multi-phase oral care compositions can comprise at least about 10%, 20%, 30%, 40%, 50%, 60%, 70%, 80%, 90%, 95%, 96%, 97%, 98%, 99% or 100% of the initial level of bleaching agent at temperatures (for example −7° C., 4° C., 23° C., 25° C., 30° C., 40° C., 50° C., or 60° C.) and conditions that the multi-phase oral care composition may be exposed to during manufacture, filling, shipping, or storage (for example 1 day, 2 days, 1 week, 2 weeks, 1 month, 2 months, 3 months, 6 months, 12 months, 18 months, or 24 months) prior to use by the consumer.

The stabilizing agent can be present in a multi-phase oral care composition of the present invention in an amount from about 0.0000001% to about 0.1%, from about 0.000001% to about 0.01%, up to about 0.1%, or preferably up to about 1%, by weight of the multi-phase oral care composition, jammed oil-in-water emulsion, or the aqueous phase.

The multi-phase oral care compositions or jammed oil-in-water emulsions, as described herein, may comprise a stabilizing agent for the bleaching agent. The bleaching agent may be further stabilized against degradation by the multi-phase oral care composition. Stabilizing agents may be added to the multi-phase oral care composition, such as in the aqueous phase. Suitable stabilizing agents include for example ortho-phosphoric acid, phosphate(s), such as sodium hydrogen phosphate, pyrophosphate(s), organophosphonate(s), Ethylenediaminetetraacetic acid, Ethylenediamine-N,N'-diacetic acid, Ethylenediamine-N,N'-disuccinic acid, potassium stannate, sodium stannate, tin salts, zinc salts, salicylic acid, 1-Hydroxyethylidene-1,1-diphosphonic acid, and combinations thereof. Suitable stabilizers can also show additional oral care effects, such as anti-tartar effect, produced by pyrophosphate(s) or organophosphonate(s).

A stabilizing agent may also include chelants. The chelant may be a copper, iron and/or manganese chelants, or a mixture thereof. Suitable chelants may be selected from: diethylene triamine pentaacetate, diethylene triamine penta (methyl phosphonic acid), ethylene diamine-N'N'-disuccinic acid, ethylene diamine tetraacetate, ethylene diamine tetra (methylene phosphonic acid), hydroxyethane di(methylene phosphonic acid), and any combination thereof. A suitable chelant may be selected from ethylene diamine-N'N'-disuccinic acid (EDDS), hydroxyethane diphosphonic acid (HEDP) or mixtures thereof. The stabilizer may comprise ethylene diamine-N'N'-disuccinic acid or salt thereof. The ethylene diamine-N'N'-disuccinic acid may be in S,S enantiomeric form. The stabilizer may comprise 4,5-dihydroxy-m-benzenedisulfonic acid disodium salt, glutamic acid-N,N-diacetic acid (GLDA) and/or salts thereof, 2-hydroxypyridine-1-oxide, Trilon P™ available from BASF, Ludwigshafen, Germany. Suitable chelants may also be calcium carbonate crystal growth inhibitors. Suitable calcium carbonate crystal growth inhibitors may be selected from the group consisting of: 1-hydroxyethanediphosphonic acid (HEDP) and salts thereof; N,N-dicarboxymethyl-2-aminopentane-1,5-dioic acid and salts thereof; 2-phosphonobutane-1,2,4-tricarboxylic acid and salts thereof; and any combination thereof.

The stabilizer may comprise a calcium carbonate crystal growth inhibitor, such as 1-hydroxyethanediphosphonic acid (HEDP); N,N-dicarboxymethyl-2-aminopentane-1,5-dioic acid; 2-phosphonobutane-1,2,4-tricarboxylic acid; and salts thereof; and any combination thereof.

The stabilizer may comprise a hydroxamate chelant. By 'hydroxamate' we herein mean hydroxamic acid or a corresponding salt, for example coco hydroxamic acid (Axis House RK 853).

Emulsifiers

The multi-phase oral care composition or high internal phase emulsion preferably a jammed oil-in-water emulsion, as described herein, comprises one or more emulsifiers. Depending on the design of the multi-phase oral care composition, the hydrophobic phase can have emulsifying properties. Thus, the emulsifier and the hydrophobic phase can comprise the same compound.

The multi-phase oral care composition or high internal phase emulsion preferably a jammed oil-in-water emulsion, as described herein, can comprise from about 0.001% to about 20%, from about 0.01% to about 10%, up to about 10%, up to about 5%, or preferably from about 0.1% to about 10%, by weight of the multi-phase oral care composition or jammed oil-in-water emulsion, of the emulsifier.

Classes of surfactants useful as emulsifiers include nonionic, anionic, cationic, amphoteric, polymeric, synthetic emulsifiers, and mixtures thereof. Many suitable nonionic and amphoteric surfactants are disclosed by U.S. Pat. Nos. 3,988,433; 4,051,234, and many suitable nonionic surfactants are also disclosed by U.S. Pat. No. 3,959,458.

The emulsifier can comprise a polysorbate, an alkyl sulfate, Lipowax® D, or combinations thereof. Suitable polysorbate compounds include, polysorbate 20, 40, 60, 80, or combinations thereof, such as Tween® 20, 40, 60, 80, or combinations thereof.

The emulsifier can comprise natural emulsifiers, such as acacia, gelatin, lecithin and cholesterol; finely dispersed solids, such as colloidal clays, bentonite, veegum (magnesium aluminum silicate; and synthetic emulsifiers, such as salts of fatty acids, sulfates such as sorbitan trioleate, sorbitan tristearate, sucrose distearate, propylene glycol monostearate, glycerol monostearate, propylene glycol monolaurate, sorbitan monostearate, sorbitan monolaurate, polyoxyethylene-4-lauryl ether, sodium lauryl sulfate, sulfonates such as dioctyl sosium sulfosuccinate, glyceryl esters, polyoxyethylene glycol esters and ethers, diethylene glycol monostearate, PEG 200 distearate, and sorbitan fatty acid esters, such as sorbitan monopalmitate, and their polyoxyethylene derivatives, polyoxyethylene glycol esters such as the monostearate, Polysorbate 80 (ethoxylated sorbitan monooleate) (supplied by Spectrum, etc.); and combinations thereof.

The emulsifier can be a surfactant that is non-reactive with a bleaching agent. For example, surfactants that are non-reactive with a bleaching agent may be substantially free of hydroxy groups, nitrogen groups and linkages, double or triple covalent bonds between adjacent carbon atoms, metals such as Zn, etc., or combinations thereof.

The multi-phase oral care compositions may be substantially free of ingredients, for example reactive emulsifiers, that at temperatures (for example −7° C., 4° C., 23° C., 25° C., 30° C., 40° C., 50° C., or 60° C.) and conditions that the multi-phase oral care composition may be exposed to during manufacture, filling, shipping, or storage (for example 1 day, 2 days, 1 week, 2 weeks, 1 month, 2 months, 3 months, 6 months, 12 months, 18 months, or 24 months) prior to use by the consumer, 1) may compromise the efficacy, comfort, usage experience, concentration of actives or bleaching agents at the tooth surface over time, active or bleaching efficiency, or compatibility between ingredients, or 2) may react with other ingredients or degrade other ingredients or may cause foam or pressure to build up in the package or container in which the multi-phase oral care composition is stored. "Substantially free of a reactive emulsifier" as used herein means that the composition comprises less than 0.001% by weight of a reactive emulsifier.

The emulsifier may be a non-ionic surfactant. Nonionic surfactants include polyoxyethylene sorbitan fatty acid esters, such as, materials sold under the trademark Tween. The number following the 'polyoxyethylene' part in the following section refers to the total number of oxyethylene —($CH_2CH_2O$)— groups found in the molecule. The number following the 'polysorbate' part is related to the type of fatty acid associated with the polyoxyethylene sorbitan part of the molecule. Monolaurate is indicated by 20, monopalmitate is indicated by 40, monostearate by 60, and monooleate by 80. Examples of such materials are polyoxyethylene (20) sorbitan monolaurate (Tween 20), polyoxyethylene (20) sorbitan monopalmitate (Tween 40), polyoxyethylene (20) sorbitan monostearate (Tween 60), polyoxyethylene (4) sorbitan monostearate (Tween 61), polyoxyethylene (20) sorbitan tristearate (Tween 65), polyoxyethylene (20) sorbitan monooleate (Tween 80), polyoxyethylene (5) sorbitan monooleate (Tween 81), and polyoxythlene (20) sorbitan trioleate (Tween 85), and mixtures thereof. Polyoxyethylene fatty acid esters are also suitable and examples include those materials sold under the trademark Myrj such as polyoxyethylene (8) stearate (Myrj 45) and polyoxyethylene (40) stearate (Myrj 52), and mixtures thereof. Further nonionics include, polyoxyethylene polyoxypropylene block polymers, such as poloxamers and Pluronics.

Another suitable class of non-ionic surfactants that can be used in the emulsifier are polyoxyethylene fatty ethers, such as, the materials sold under the trademark Brij. Examples of such materials are polyoxyethylene (4) lauryl ether (Brij 30), polyoxyethylene (23) lauryl ether (Brij 35), polyoxyethylene (2) cetyl ether (Brij 52), polyoxyethylene (10) cetyl ether (Brij 56), polyoxyethylene (20) cetyl ether (Brij 58), polyoxyethylene (2) stearyl ether (Brij 72), polyoxyethylene (10) stearyl ether (Brij 76), polyoxyethylene (20) stearyl ether (Brij 78), polyoxyethylne (2) oleyl ether (Brij 93), polyoxyethylene (10) oleyl ether, and polyoxyethylene (20) oleyl ether (Brij 99), and mixtures thereof.

A portion of a non-ionic surfactant may be substituted with a lipophilic surfactant, such as, sorbitan fatty acid esters such as the materials sold under the trademark Arlacel. Suitable lipophilic surfactants include sorbitan monolaurate (Arlacel 20), sorbitan monopalmitate (Arlacel 40), sorbitan monostearate (Aracel 60), sorbitan monooleate (Arlacel 80), sorbitan sesquioleate (Arlacel 83), and sorbitan trioleate (Arlacel 85), and mixtures thereof. Typically, from about 2% to about 90% of the level of the nonionic surfactant may be substituted by a lipophilic surfactant, or from about 25% to about 50%.

Each emulsifier and/or blends of multiple emulsifiers can have a hydrophilic-lipophilic balance (HLB) value. An emulsifier that is lipophilic in character is assigned a low HLB number (below about 9), and one that is hydrophilic is assigned a high HLB number (above about 11). In certain embodiments, the skilled formulator will recognize the importance of selecting an emulsifier (or blend of multiple emulsifiers) with a suitable balance of hydrophilic and lipophilic properties to encourage the formation of a high internal phase emulsion or preferably a jammed emulsion. The HLB is calculated according to the procedure specified previously. Information on emulsifiers and HLB values can be found in 1) "Emulsion science and technology" edited by Tharwat F. Tadros, Wiley VCH, ISBN: 978-3-527-32525-2, 2) "Classification of surface-active agents by HLB" by W. C. Griffin of the Atlas Powder Company in the Journal of Cosmetic Chemists 1949, 3) "Calculation of HLB of non-ionic surfactants" by W. C. Griffin in the Journal of Cosmetic Chemists 1954, 4) "Interfacial phenomena", Chapter 8 "Disperse systems and adhesion" by J. T. Davies and E. K. Rideal Academic Press, New York, 1963, 5) "A quantitative kinetic theory of emulsion type I, physical chemistry of the emulsifying agent" by J. T. Davies J. H. Schulman (Ed.), Proceedings of the 2nd International Congress on Surface Activity, 1, Academic Press, New York (1957), 6) "Span and Tween" brochure 08/10 D1005/1 by Croda Europe Ltd. England, 7) "Food enrichment with Omega-3 fatty acids", Chapter 5 "Stabilization of omega-3 oils and enriched foods using emulsifiers" by C. Genot, T.-H. Kabri and A. Meynier, France, Woodhead Publishing, and 8) "Health Care Prodoct Guide—North America", brochure "Pharmaceuticals, Dermatology, Delivering your solution, Animal Health, Nutraceuticals" by Croda. The emulsifiers and blends of multiple emulsifiers along with their HLB values specified in these documents are incorporated herein by reference.

An emulsifier that tends to form a water-in-oil emulsion and an emulsifier that forms an oil-in-water emulsion may be blended to achieve an HLB suitable for an oil-in-water emulsion. The average HLB number of the blend may be calculated from additivity:

$$\text{HLB of blend} = (a)*\text{HLB}_1 + (b)*\text{HLB}_2$$

Wherein a and b are the weight fractions of the two emulsifiers with $HLB_1$ and $HLB_2$.

For example, to determine the HLB value of a blend comprising 70% of TWEEN 80 (HLB=15) and 30% Of SPAN 80 (HLB=4.3), the calculation would be:

The contribution from TWEEN 80 is 70%×15.0=10.5
The contribution from SPAN 80 is 30%×4.3=1.3
Thus, the HLB of blend is 11.8 (i.e. 10.5+1.3)

The HLB values of various emulsifiers and/or blends of multiple emulsifiers can be from about are from about 0 to about 60, above 11, from about 11 to about 60, from about 11 to about 40, preferably from about 11 to about 20, or more preferred from about 16 to about 18, or combinations thereof; or from about 20 to about 40, or from about 30 to about 40.

The emulsifier or blend of multiple emulsifiers can be hydrophilic, miscible with water, immiscible with mineral oil, or combinations thereof.

Each emulsifier can comprise at least one hydrophobic tail group and at least one hydrophilic head group. There can be from about 6 to about 20, from about 8 to about 16, or from about 10 to 14 carbon atoms in from about 1 to about 4, from about 1 to about 3, or from about 1 to about 2 hydrophobic tails, or in 1 hydrophobic tail. Each hydrophobic tail can have up to about 4, up to about 3, or up to about 1 branch, or 0 branches. Each hydrophobic tail can have up to about 3, up to about 2, up to about 1, or 0 alkene functional groups (or carbon-carbon double bonds). The hydrophilic head group of each emulsifier molecule can comprise from about PEG-4 to about PEG-40, from about PEG-8 to about PEG-30, or preferably from about PEG-16 to about PEG-24 attached to sorbitan. The emulsifier can comprise from about 4 to about 60, from about 8 to about 30, from about 16 to about 34 of moles of ethylene oxide in each emulsifier molecule.

The emulsifier or blend of multiple emulsifiers can comprise PEG-20 sorbitan monolaurate (Tween 20), PEG-20 sorbitan monooleate (Tween 80), and/or sodium lauryl sulfate. Preferably, the emulsifier can comprise PEG-20 sorbitan monolaurate.

The emulsifier (and HLB) may comprise one or more of the following list, and blends of multiple emulsifiers may comprise blends of these in any combination thereof: Span 20 (HLB of 8.6), Span 40 (6.7), Span 60 (4.7), Span 80 (4.3), Span 83 (3.7), Span 85 (1.8), Span 120 (4.7), Tween 20 (16.7), Tween 21 (13.3), Tween 40 (15.6), Tween 60 (14.9), Tween 61 (9.6), Tween 65 (10.5), and Tween 80 (15).

Other Optional Components

The multi-phase oral care composition as disclosed herein may comprise additional optional ingredients, and which will be described below in further detail.

The multi-phase oral care compositions herein may comprise a safe and effective amount of a thickening agent, viscosity modifier or particulate fillers. A thickening agent may further provide acceptable rheology of the composition. The viscosity modifier may further function to inhibit settling and separation of components or control settling in a manner that facilitates re-dispersion and may control flow properties of the composition. In addition, a thickening agent or viscosity modifier may facilitate use of the present compositions with suitable applications devices, such as strips, films or dental trays by increasing the retention onto the surfaces of the application devices. The thickening agent, as described herein, may also serve as an adhesive. When present a thickening agent, viscosity modifier, or particulate filler may be present from about 0.1% to about 50%, from about 1% to about 25%, or from about 1% to about 10%, by weight of the multi-phase oral care composition.

Suitable thickening agents, viscosity modifiers, or particulate fillers that can be used herein include organo modified clays, silicas, synthetic polymers such as crosslinked siloxanes, cellulose derivatives (e.g. methylcellulose, carboxymethylcellulose, hydroxyethylcellulose, hydroxypropyl-cellulose, hydroxy-propylmethylcellulose, etc.), carbomer polymers (e.g. crosslinked polyacrylic acid copolymer or homopolymer and copolymers of acrylic acid cross linked with a polyalkenyl polyether), natural and synthetic gums, karaya gum, guar gum, gelatin, algin, sodium alginate, tragacanth, chitosan, polyethylene oxide, acrylamide polymers, polyacrylic acid, polyvinyl alcohol, polyamines, polyquarternary compounds, ethylene oxide polymers, polyvinylpyrrolidone, cationic polyacrylamide polymers, waxes (which includes paraffin wax and microcrystalline waxes), polyethylene, fumed silica, polymethacrylates, olefin copolymers, hydrogenated styrene-diene copolymers, styrene polyesters, rubber, polyvinylchloride, nylon, fluorocarbon, polyurethane prepolymer, polyethylene, polystyrene, alkylated polystyrene, polypropylene, cellulosic resins, acrylic resins, elastomers, poly(n-butyl vinyl ether), poly(styrene-co-maleic anhydride), poly(alkyl fumarate co-vinyl acetate), poly(t-butyl styrene), and mixtures thereof.

Examples of polyethylene include A-C 1702 or A-C 6702 made by Honeywell Corp. (Morristown, N.J.), with a penetration value of about 98.5 and about 90.0, respectively, under ASTM D1321; polyethylene Performalene series from Baker Hughes; this includes polyethylene Performalene 400 from Baker Hughes Inc. (Houston, Tex.). Examples of microcrystalline wax include the Multiwax series from Sonneborn (Parsippany, N.J.), Crompton (Witco); these include Multiwax 835, Multiwax 440, Multiwax 180, and mixtures thereof.

Examples of polymethacyrlates include, for example, polyacrylate-co-methacrylate, polymethacrylate-co-styrene, or combinations thereof. Examples of elastomers include, for instance, hydrogenated styrene-co-butadiene, hydrogenated styrene-co-isoprene, ethylene-ethylene-propylene polymer, ethylene-propylene polymer, styrene-ethylene-ethylene-propylene-styrene polymer or combinations thereof. An example of a rubber includes hydrogenated polyisoprene. Other examples of viscosity modifiers can be found in "Chemistry and Technology of Lubricants," Chapman and Hall ($2^{nd}$ Ed. 1997).

Suitable carbomers comprises the class of homopolymers of acrylic acid crosslinked with an alkyl ether of pentaerythritol or an alkyl ether of sucrose. Carbomers are commercially available from B.F. Goodrich as the Carbopol® series, such as Carbopol 934, 940, 941, 956, and mixtures thereof. Homopolymers of polyacrylic acid are described, for example, in U.S. Pat. No. 2,798,053. Other examples of homopolymers which are useful include Ultrez 10, ETD 2050, and 974P polymers, which are available from The B.F. Goodrich Company (Greenville, S.C.). Such polymers include homopolymers of unsaturated, polymerizable carboxylic monomers such as acrylic acid, methacrylic acid, maleic acid, itaconic acid, maleic anhydride, and the like.

Coolants, desensitizing agents and numbing agents can be used as optional ingredients in compositions of the present invention, such as at a level of from about 0.001% to about 10%, or preferably from about 0.1% to about 1%, by weight of the composition. Coolants, desensitizing agents and numbing agents may decrease potential negative perceptions, such as tingling, burning etc. . . . Coolant can be any of a wide variety of materials. Included among such materials are carboxamides, menthol, ketals, diols, and mixtures thereof. Optional coolants in the present compositions may be the paramenthan carboxyamide agents such as N-ethyl-p-menthan-3-carboxamide (known as "WS-3"), N,2,3-trimethyl-2-isopropylbutanamide (known as "WS-23"), menthol, 3-1-menthoxypropane-1,2-diol (known as TK-10), menthone glycerol acetal (known as MGA) menthyl lactate (known as Frescolat®), and mixtures thereof. The terms menthol and menthyl as used herein include dextro- and levorotatory isomers of these compounds and racemic mixtures thereof. Desensitizing or Anti-pain agent may include, but are not limited to, strontium chloride, potassium nitrate, oxalate salts or acids, natural herbs such as gall nut, Asarum, Cubebin, Galanga, scutellaria, Liangmianzhen, Baizhi, etc. Suitable numbing agents include benzocaine, lidocaine, clove bud oil, and ethanol.

In addition, the compositions as disclosed herein may optionally comprise a safe and effective amount of a flavoring agent. Suitable flavoring agents include oil of wintergreen, oil of peppermint, oil of spearmint, clove bud oil, menthol, anethole, methyl salicylate, eucalyptol, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal (known as CGA), and mixtures thereof. If present the flavoring agents are generally used at levels of from about 0.01% to about 30%, preferably from about 0.5% to about 20%, more particular from about 1.5% to about 15%, by weight of the composition.

In addition, the present compositions may optionally comprise sweetening agents including sucralose, sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. If present, the composition contains from about 0.1% to about 10% of these agents, or preferably from about 0.1% to about 1%, by weight of the composition.

In addition, dyes, pigments, colorants, and mixtures thereof may optionally be included in the present composition to give the compositions herein colored appearance. An advantage of adding pigments and/or colorants to the compositions herein is that it will allow the patient to see if the composition covers their teeth evenly and completely, since coverage is easier to see with a colored composition. In addition, the colorant may provide color similar to the color of bleached teeth. Colorants useful herein are stable with the bleach agent and are those recognized as safe. The levels of dye, pigments and colorants that are optionally used herein are in the range of about 0.05% to about 20%, preferably from about 0.10% to about 15% and more preferably from about 0.25% to about 5% by weight of the composition.

Multi-Phase Compositions Comprising a Peroxide Compound

For multi-phase oral care compositions that comprise peroxide, it has been surprisingly found that the standard deviation of the peroxide concentration of a multi-phase oral care composition smeared onto peroxide test strips is a factor to decrease oral/topical irritation and/or tooth-sensitivity during use. Each peroxide test strip has two reaction-zones that change color (driving the R value intensity lower) in areas or spots that are contacted with peroxide. Thus, without being bound by theory, peroxide test strips may conveniently be used as a proxy for oral/topical/tooth surfaces to identify spots of high peroxide concentration that may lead to oral/topical irritation and/or tooth-sensitivity.

Furthermore, since contact with peroxide drives the R value intensity lower in the reaction-zones, the mean R value intensity of peroxide test strips smeared with the multi-phase oral care composition subtracted from the mean baseline R value intensity of untreated peroxide test strips may conveniently be used as a measure of the mean peroxide concentration. Multi-phase oral care compositions that have large spots of high peroxide concentration when the multi-phase oral care composition is smeared on peroxide test strips may also have large spots of high peroxide concentration when the multi-phase oral care composition is applied to oral/topical/tooth surfaces—this in turn may lead to oral/topical irritation and/or tooth-sensitivity. In contrast, multi-phase oral care compositions that have only small spots of high peroxide concentration when the multi-phase oral care composition is smeared onto peroxide test strips may also have only small spots of high peroxide concentration when the multi-phase oral care composition is applied to oral/topical/tooth surfaces—this in turn may lead to low oral/topical irritation and/or tooth-sensitivity. The spots of peroxide concentration when the multi-phase oral care composition is smeared onto peroxide test strips can be quantified by the standard deviation of the peroxide concentration on the test strips measured using the method specified herein. Multi-phase oral care compositions that have large spots of high peroxide concentration when the multi-phase oral care composition is smeared onto peroxide test strips have a high standard deviation of the peroxide concentration on the test strips. In contrast, multi-phase oral care compositions that have only small spots of high peroxide concentration when the multi-phase oral care composition is smeared onto peroxide test strips have a low standard deviation of the peroxide concentration on the test strips.

Furthermore, multi-phase oral care compositions with large droplets of the aqueous phase may cause large spots of high peroxide concentration when the multi-phase oral care composition is smeared onto peroxide test strips—this in turn may lead to a high standard deviation of the peroxide concentration on the test strips. In contrast, multi-phase oral care compositions that have little or no large droplets of the aqueous phase may cause only small spots of high peroxide concentration when the multi-phase oral care composition is smeared onto peroxide test strips—this in turn may lead to a low standard deviation of the peroxide concentration on the test strips.

The standard deviation of the peroxide concentration of a multi-phase oral care composition smeared onto peroxide test strips measured using the method specified herein can be up to about 50, up to about 25, up to about 10, from about 5 to about 15, or preferably from about 1 to about 10.

For multi-phase oral care compositions that comprise peroxide, it has surprisingly been found that the mean peroxide concentration of a multi-phase oral care composition smeared onto peroxide test strips is a factor to deliver bleaching efficacy. Without being bound by theory, if the mean peroxide concentration of a multi-phase oral care composition smeared onto peroxide test strips is low, the mean peroxide concentration delivered to the tooth surface during use may also be low, which could lead to low bleaching effectiveness. In contrast, if the mean peroxide concentration of a multi-phase oral care composition smeared onto peroxide test strips is high, the mean peroxide concentration delivered to the tooth surface during use may also be high, which could lead to high bleaching effectiveness.

The mean peroxide concentration of a multi-phase oral care composition smeared onto peroxide test strips measured using the method specified herein may be from about 10 to about 225, from about 25 to about 200, or preferably from about 40 to about 100.

In contrast, if the ratio of the mean peroxide concentration of a multi-phase oral care composition smeared onto peroxide test strips to the standard deviation of the peroxide concentration of a multi-phase oral care composition smeared onto peroxide test strips is low, the composition may deliver low efficacy combined with high oral/topical irritation and/or tooth-sensitivity during use. The ratio of the mean peroxide concentration of a multi-phase oral care composition smeared onto peroxide test strips measured using the method specified herein to the standard deviation of the peroxide concentration of a multi-phase oral care composition smeared onto peroxide test strips measured using the method specified herein may be no less than about 0.25, 0.5, 1, 1.5, 2, 2.5, 3, 3.5, 4, 4.5, 5, 6, 7, 8, 9, 10, 15, 20, 25, 50 or any other numerical range, which is narrower and which falls within such broader numerical range, as if such narrower numerical ranges were all expressly written herein. The ratio of the mean peroxide concentration of a multi-phase oral care composition smeared onto peroxide test strips measured using the method specified herein to the standard deviation of the peroxide concentration of a multi-phase oral care composition smeared onto peroxide test strips measured using the method specified herein may be no less than about 0.5, preferably no less than about 1, more preferably no less than about 2, and most preferably no less than about 3.5, or any other numerical range, which is narrower and which falls within such broader numerical range, as if such narrower numerical ranges were all expressly written herein.

It has surprisingly been found that the Brookfield Viscosity of the multi-phase oral care compositions of the present invention impacts the mean peroxide concentration of a multi-phase oral care composition smeared onto peroxide test strips measured according to the method specified herein. Specifically, it has been surprisingly found that multi-phase oral care compositions of the present invention with a lower Brookfield Viscosity deliver a higher mean peroxide concentration of the multi-phase oral care compositions smeared onto peroxide test strips measured according to the method specified herein.

The components of the aqueous phase and hydrophobic phase are chosen to allow for the release of the oral care active, which may be a bleaching agent dissolved in the aqueous phase, readily from the composition.

Without being bound by theory it is believed that when the present invention, which may be in the form of a jammed oil-in-water emulsion, is brought into contact with a tooth surface, the aqueous phase and the components of the aqueous phase may migrate to the tooth surface. The possible net effect is that the active effect, which may be a tooth whitening effect, is started only after contact with the tooth surface to be treated. That means, the active which may be a bleaching agent may be protected against environmental influence and thereby stabilized by the hydrophobic phase of the multi-phase oral care composition until use. Thereby, the active effect may be applied to the tooth surface and the active agent, e.g. the bleaching agent may be potentially shielded against the oral environment during use. Thereby the efficacy of a whitening multi-phase oral care composition may be enhanced and/or accelerated.

Without further being bound by theory, the present invention may improve the delivery of the whitening agent to the tooth surface and thus the whitening performance due to the partial hydrophobic and partial hydrophilic nature of the composition. Due to the driving force resulting therefrom the active agent, which may be a bleaching agent present in the aqueous phase, may be driven towards the tooth surface. Thereby increased speed of whitening and increased efficacy of the bleaching agent may be achieved, even though surprisingly low total levels of the bleaching agent can be used. Certain embodiments of the present invention, at a given total overall concentration, such as 0.1%, 0.5%, 1%, 2,%, 3%, 4%, 5%, 6%, 7%, 8%, 9% or 10%, by weight or below of a bleaching agent, delivers a surprisingly high level of whitening efficacy, may require fewer applications to get the same degree of whitening, or may require a lower gel load (milligrams of gel per unit area) to get the same degree of whitening.

In addition, retention of the multi-phase oral care composition on the tooth surfaces may be improved as the hydrophobic phase resists salivary dilution and salivary enzymes which can decompose the peroxide. Even furthermore, the hydrophobic phase likely does not dehydrate the teeth creating an outward flux of water created by many hydrophilic compositions containing hydrophilic adhesives such as polycarboxylic acid. Since the hydrophobic phase likely does not dehydrate the teeth it may result in a surprisingly low level of tooth sensitivity even while delivering a surprisingly high level of whitening efficacy.

In addition, the hydrophobic phase may provide further advantages. For example, the hydrophobic phase represents a stable matrix for ingredients which can be soluble in the hydrophobic phase. For example, many oil-soluble active agents or flavor ingredients usually used in oral compositions may be soluble in the hydrophobic phase. That means the flavor ingredients may be protected from any influence of the active agent, for example the bleaching agent, in the oral composition. In addition, during use of the oral composition at the tooth surface at least part of the hydrophobic phase may be located—without being bound by theory—towards the soft oral tissues, such as the mucosa, thereby presenting the ingredients which can be present in the hydrophobic phase, such as flavor compounds, to the oral cavity. In addition, the hydrophobic phase may shield the active agent, such as the bleaching agent against any influence from the oral cavity, such as dilution by saliva. The shielding effect may also apply to the tooth surface(s) themselves, wherein the hydrophobic phase may provide greater hydration of the teeth surfaces.

The multi-phase oral care compositions of the present invention may be in the form of a liquid, viscous liquid, gel, semisolid, solid, particulate, powder, viscoelastic liquid, viscoelastic gel, sol, viscoelastic solid, or any combination thereof.

Without being bound by theory, macroscopic separation of one or more of the components of the multi-phase oral care composition at temperatures (for example $-7°$ C., $4°$ C., $23°$ C., $25°$ C., $30°$ C., $40°$ C., $50°$ C., or $60°$ C.) and conditions that the multi-phase oral care composition may be exposed to during manufacture, filling, shipping, or storage (for example 1 day, 2 days, 1 week, 2 weeks, 1 month, 2 months, 3 months, 6 months, 12 months, 18 months, or 24 months) prior to use by the consumer may compromise the efficacy, comfort, usage experience, concentration of actives or bleaching agents at the tooth surface over time, active or bleaching efficiency, or compatibility between ingredients. The multi-phase oral care composition can be considered stable if there is no more than about 1%, 2%, or 5%, by total volume of the multi-phase oral care composition, macroscopic separation for at least 2 days or 7 days while being stored at 23° C., 40° C., and/or 60° C., as measured according to the method described herein.

For example, compositions that exhibit macroscopic separation of the bleaching agent or phases that contain a bleaching agent prior to use by the consumer may cause the concentration of bleaching agent to change from one dose to the other, and/or over time. This can compromise the efficacy, comfort, or usage experience (via oral irritation or tooth sensitivity for example) in certain doses; and this may vary from dose to dose, and/or over time. Specifically, if for example, a substantial portion of the bleaching agent has macroscopically separated into multiple visual phases, a dose that is disproportionately rich in this phase may cause oral irritation or tooth sensitivity when it comes in contact with the oral soft tissue or teeth, while a dose that is disproportionately poor in this phase may deliver decreased bleaching efficacy. Both these conditions can be undesirable because one can lead to higher discomfort, and the other leads to lower efficacy.

The macroscopic separation of one or more of the components of the multi-phase oral care composition measured according to the method specified herein after 2 days at 23° C. or 60° C. can be less than about 20%, less than about 10%, less than about 5%, or preferably less than about 2%, by weight or volume of the multi-phase oral care composition.

The bleaching efficacy of the present invention, as measured per the clinical protocol disclosed herein, and calculated as $-\Delta b^*$ may be at least about 0.25, preferably at least about 0.5, more preferred at least about 1.0, even more preferred at least about 1.5, even more preferred at least about 2, even more preferred at least about 2.5, even more preferred at least about 3, even more preferred at least about 3.5, and even more preferred at least about 4, or any other numerical range, which is narrower and which falls within such broader numerical range, as if such narrower numerical ranges were all expressly written herein. Generally, a change in yellowness, as measured per the clinical protocol as disclosed herein, and calculated as $-\Delta b^*$ of at least 0.25 is noticeable.

The present invention can deliver a surprisingly high ratio of bleaching efficacy of the present invention, as measured per the clinical protocol disclosed herein, and calculated as $-\Delta b^*$, to the weight percent of bleaching agent present in the overall multi-phase oral care composition. For example, a $-\Delta b^*$ of 1.5 with a composition containing 3% of bleaching agent, would deliver a ratio of bleaching efficacy, as measured per the clinical protocol as disclosed herein, and calculated as $-\Delta b^*$, to the weight percent of bleaching agent present in the overall multi-phase oral care composition of 0.5.

The ratio of bleaching efficacy of the present invention, as measured per the clinical protocol disclosed herein, and calculated as $-\Delta b^*$ to the weight percent of bleaching agent present in the overall multi-phase oral care composition may be at least about 2.5, preferably at least about 5, more preferred at least about 10, even more preferred at least about 15.

The bleaching efficacy of the present invention, as measured per the clinical protocol disclosed herein and calculated as $-\Delta b^*$ may be at least about 10%, at least about 100%, at least about 1000%, or at least about 10,000% more than the bleaching efficacy of a comparative oral care composition in the form of an aqueous solution or aqueous gel. The comparative oral care composition comprises the same bleaching agent at the same overall concentration dissolved into the aqueous solution or aqueous gel.

The present invention delivers: 1) a surprisingly high ratio of bleaching efficacy, as measured per the clinical protocol as disclosed herein, and calculated as $-\Delta b^*$, to the fraction of participants who reported oral irritation or were observed to have oral irritation that was possibly or probably attributed to the composition tested; 2) a surprisingly high ratio of bleaching efficacy of the present invention, as measured per the clinical protocol as disclosed herein, and calculated as $-\Delta b^*$ to the fraction of participants who reported tooth sensitivity that was possibly or probably attributed to the composition; or 3) a surprisingly high ratio of bleaching efficacy of the present invention, as measured per the clinical protocol as disclosed herein, and calculated as $-\Delta b^*$, to the fraction of participants who reported tooth sensitivity or reported oral irritation or were observed to have oral irritation that was possibly or probably attributed to the composition.

The ratio of bleaching efficacy of the present invention, as measured per the clinical protocol as disclosed herein, and calculated as $-\Delta b^*$, to the fraction of participants who report tooth sensitivity that is possibly or probably attributed to the present invention may be at least about 1, at least about 2, at least about 5, at least about 6, preferably at least about 7, more preferred at least about 8, even more preferred at least about 9, even more preferred at least about 10, even more preferred at least about 15, even more preferred at least about 20, even more preferred at least about 25, and even more preferred at least about 50, or any other numerical range, which is narrower and which falls within such broader numerical range, as if such narrower numerical ranges were all expressly written herein.

The ratio of bleaching efficacy of the present invention, as measured per the clinical protocol as disclosed herein, and calculated as $-\Delta b^*$, to the fraction of participants who report oral irritation or are observed to have oral irritation that is possibly or probably attributed to the present invention may be at least about 1, at least about 2, at least about 5, at least about 6, preferably at least about 7, more preferred at least about 8, even more preferred at least about 9, even more preferred at least about 10, even more preferred at least about 15, even more preferred at least about 20, even more preferred at least about 25, and even more preferred at least about 50, or any other numerical range, which is narrower and which falls within such broader numerical range, as if such narrower numerical ranges were all expressly written herein.

The ratio of bleaching efficacy of the present invention, as disclosed herein, and calculated as $-\Delta b^*$, to the fraction of participants who report tooth sensitivity or report oral irritation or are observed to have oral irritation that is possibly or probably attributed to the present invention may be at least about 6, preferably at least about 7, more preferred at least about 8, even more preferred at least about 9, even more preferred at least about 10, even more preferred at least about 15, even more preferred at least about 20, even more preferred at least about 25, and even more preferred at least about 50, or any other numerical range, which is narrower and which falls within such broader numerical range, as if such narrower numerical ranges were all expressly written herein.

The residual peroxide intensity of the multi-phase oral care composition, as described herein, can be up to about 200, up to about 100, or preferably up to about 10.

Delivery Carrier

The present invention may further be related to a delivery system or methods for delivering the multi-phase oral care compositions and/or jammed oil-in-water emulsion directly to the oral cavity or at least one tooth within the oral cavity of a consumer. The multi-phase compositions can be used in combination with a re-usable delivery carrier, such as a tray, mouth guard, retainer, or combinations thereof. As the delivery carrier may be re-usable, it is desirable for the multi-phase oral care composition to be rinseable or water-dispersible, as described herein. The multi-phase compositions can also be used in combination with a disposable or single-use delivery carrier, such as a disposable strip.

For example, the delivery system may comprise a first layer of a carrier material and a second layer comprising a multi-phase oral care composition described herein, whereby the bleaching agent is releasably located within the present composition. A suitable first layer may comprise a delivery carrier including a strip of material, a dental tray, a sponge material, and mixtures thereof. The delivery carrier may be a strip of material, such as a permanently deformable strip. Suitable strips of material or permanently deformable strips are for example disclosed in U.S. Pat. Nos. 6,136,297; 6,096,328; 5,894,017; 5,891,453; and 5,879,691; and in U.S. Pat. Nos. 5,989,569 and 6,045,811; and in patent application US 2014/0178443 A1.

The delivery carrier may be attached to the teeth via an attachment means that is part of the delivery carrier, for example the delivery carrier may be of sufficient size that, once applied the delivery carrier overlaps with the oral soft tissues rendering more of the teeth surface available for bleaching. The delivery carrier may also be attached to the oral cavity by physical interference or mechanical interlocking between the delivery carrier and the oral surfaces including the teeth.

The delivery carrier maybe transparent or translucent to electromagnetic radiation with wavelengths from about 200 nm to about 1700 nm. The delivery carrier can allow from about 10%, 20%, or 30% to about 40%, 50%, 60%, 70%, 80%, 90%, or 100% of electromagnetic radiation from about 1 nm to about 750 nm, 400 nm to about 500 nm, or from about 250 nm to about 700 nm to pass through.

The delivery carrier may comprise a dissolvable film, such as the dissolvable film strip disclosed in U.S. Pat. No. 6,709,671, which can be adhered to the oral cavity thereby releasing an active, the dissolvable film comprising water-soluble polymers, one or more polyalcohols, and one or more actives. In addition to one or more actives, a dissolvable film may contain a combination of certain plasticizers or surfactants, colorants, sweetening agents, flavors, flavor enhancers, or other excipients commonly used to modify the taste of formulations intended for application to the oral cavity. The resulting dissolvable film is characterized by an instant wettability which causes the dissolvable film to soften soon after application to the mucosal tissue, thus preventing the patient from experiencing any prolonged adverse feeling in the mouth, and a tensile strength suitable for normal coating, cutting, slitting, and packaging operations.

The dissolvable film may comprise a water-soluble polymer or a combination of water-soluble polymers, one or more plasticizers or surfactants, one or more polyalcohols, and an active. The polymers used for the dissolvable film include polymers which are hydrophilic and/or water-dispersible. Examples of polymers that can be used include polymers that are water-soluble cellulose-derivatives, such as hydroxypropylmethyl cellulose, hydroxyethyl cellulose, or hydroxypropyl cellulose, either alone, or mixtures thereof. Other optional polymers, without limiting the invention, include polyvinyl pyrrolidone, carboxymethyl cellulose, polyvinyl alcohol, sodium alginate, polyethylene glycol, natural gums like xanthan gum, tragacantha, guar gum, acacia gum, arabic gum, water-dispersible polyacrylates like polyacrylic acid, methylmethacrylate copolymer, carboxyvinyl copolymers. The concentration of the water-soluble polymer in the final film can very between 20 and 75% (w/w), or between 50 and 75% (w/w).

The strip of material may contain shallow pockets. When the multi-phase oral care composition is coated on a strip of material, bleach agents and/or oral care actives, fill shallow pockets to provide reservoirs of additional bleach agents and/or oral care actives. Additionally, the shallow pockets help to provide texture to the delivery system. The strip of material may have an array of shallow pockets. Generally, the shallow pockets are approximately 0.4 mm across and about 0.1 mm deep. When shallow pockets are included in the strip of material and multi-phase oral care compositions herein are applied to it in various thicknesses, such as an overall thickness of the delivery system of less than about 1 mm, or preferably less than about 0.5 mm.

The delivery systems as used herein may comprise an adhesion means, such that they are capable of adhesion to oral surfaces, especially the teeth. This adhesion means may be provided by the present compositions herein or the adhesion means may be provided independently of the compositions herein (for example the adhesion means is a separate phase from the compositions herein where the compositions may also have an adhesive means). The strip of material may be held in place on the oral surface by adhesive attachment provided by the present composition. The viscosity and general tackiness of the multi-phase oral care composition to dry surfaces may cause the strip to be adhesively attached to the oral surface without substantial slippage from the frictional forces created by the lips, teeth, tongue, and other oral surfaces rubbing against the strip of material while talking drinking, etc. However, this adhesion to the oral surface may be low enough to allow the strip of material to be easily removed by the wearer by simply peeling off the strip of material using one's finger. The delivery system may be easily removable from the oral surfaces without the use of an instrument, a chemical solvent or agent or excess friction.

In addition, the strip of material may be held in place on the oral surface by adhesive means and attachment provided by the delivery carrier itself. For example, the strip of material can extend, attach, and adhere to the oral soft tissue. In addition, an adhesive can be applied to that portion of the strip of material that will attach the delivery systems to the oral soft tissue. The delivery carrier may also be attached to the oral cavity by physical interference or mechanical interlocking between the delivery carrier and the oral surfaces including the teeth. In addition, the strip of material may be held in place by an adhesion means that is independent of the composition of the present inventions herein, as disclosed in WO 03/015656.

Suitable adhesion means are known to the skilled person. When the adhesive means, if present, is provided by an adhesive, the adhesive may be any adhesive which may be used to adhere materials to the tooth surface or to a surface of the oral cavity surfaces. Suitable adhesives include, but are not limited to, skin, gum and muco-adhesives, and should be able to withstand the moisture, chemicals and enzymes of the oral environment for long enough for the oral care actives and/or bleach to take effect, but may be soluble and/or biodegradable thereafter. Suitable adhesives may for example comprise water soluble polymers, hydrophobic and/or non-water-soluble polymers, pressure and moisture sensitive adhesives, e.g. dry adhesives which become tacky upon contact with the mouth environment, e.g. under the influence of moisture, chemicals or enzymes etc. in the mouth. Suitable adhesives include natural gums, synthetic resins, natural or synthetic rubbers, those gums and polymers listed above under "Thickening Agents", and various other tacky substances of the kind used in known adhesive tapes, those known from U.S. Pat. No. 2,835,628.

In addition, the delivery system may comprise an optional release liner. Such a release liner may be formed from any material which exhibits less affinity for the second layer composition than the second layer composition exhibits for itself and for the first layer strip of material. The release liner may comprise a rigid sheet of material such as polyethylene, paper, polyester, or other material, which is then coated with a nonstick type material. The release liner may be cut to substantially the same size and shape as the strip of material or the release liner may be cut larger than the strip of material to provide a readily accessible means for separating the material from the strip. The release liner may be formed from a brittle material that cracks when the strip is flexed or from multiple pieces of material or a scored piece of material. Alternatively, the release liner may be in two overlapping pieces such as a typical adhesive bandage design. A description of materials suitable as release agents is found in Kirk-Othmer, Encyclopedia of Chemical Technology, Fourth Edition, Volume 21, pp. 207-218.

The delivery carrier may be a permanently deformable strip of material having a yield point and thickness such that the strip of material substantially conforms to a shape of a tooth via permanent deformation under a pressure less than about 250,000 Pascals as it has been found that wearers will press a strip onto each tooth using one fingertip having about one square centimeter surface area. They typically apply force at each tooth for one second or less with a typical application pressure ranging from about 100,000 Pascals to about 250,000 Pascals.

The strip of material can have visco-elastic properties which enable it to creep as well as bend in order to conform across several teeth and around the arch of the wearer's mouth. It is important that the necessary permanent deformation occurs under minimum normal force being applied by the wearer.

The multi-phase oral care composition may also be applied to the tooth surface and may be covered with the deformable strip before or after it has been shaped. In addition or alternatively, the multi-phase oral care composition may be applied to the deformable strip as pre-coating and may be applied together with the strip to the tooth surface before or after the deformable strip has been shaped, wherein the strip is applied such that when the delivery system is placed on a surface of the tooth, the multi-phase oral care composition contacts the tooth surface providing an active onto the tooth surface. In addition or alternatively, the deformable strip of material may be applied to the teeth with a force sufficient to shape the delivery carrier such that it at least partially conforms to the shape of the teeth, then the shaped strip of material may be removed from the tooth surface, the oral care composition may be applied to the shaped strip of material, and the shaped strip of material may be re-applied to the tooth surface such that it at least partially conforms to a shape of the tooth and contacts the oral care composition against the tooth surface. If the deformable strip is applied together with the multi-phase oral care composition to the tooth surface the multi-phase oral care composition may also comprise adhesive agents to hold the delivery system in place for a sufficient time to allow the active of the multi-phase oral care composition to act upon the surface. The multi-phase oral care composition, if used together with a deformable strip, may have an extrusion resistance sufficient to withstand a normal force applied to shape the deformable strip of material so that the substance is not substantially extruded from between the deformable strip of material and the surface during manual shaping of the deformable strip of material. By "substantially extruded from" is meant that at least 50% or more of the multi-phase oral care composition is extruded from between the deformable strip of material and the tooth and adjoining soft tissue surfaces.

The deformable strip of material may be made of a permanently deformable material, such as wax, putty, tin or foil, as a single layer or a combination of layers or materials, such as a laminate. In certain embodiments, the deformable strip may be wax, such as #165 sheet wax formulated and manufactured by Freeman Mfg. & Supply Co. of Cleveland, Ohio. This particular wax readily conforms to the shape of a tooth under a pressure of about 133,000 Pascal which is the pressure generated when the wearer applies a normal force of about 3 pounds (1.36 kg) over an area of about one square centimeter. The deformable strip of material may have a nominal film thickness of about 0.8 mm, wherein the deformable strip may be substantially flat and rectangular in shape with rounded corners. The deformable strip of material may have a length sufficient to cover a plurality of adjacent teeth while conforming to the curvature of the wearer's mouth and gaps between the adjacent teeth. If the deformable strip of material includes the multi-phase oral care composition coated thereon, the multi-phase oral care composition may have an overall thickness less than about 1.5 mm. Deformable strips as disclosed herein may also be used as the material for the strip of material 12 shown in FIGS. 1 to 4. Thus, general features of a strip of material as described above for example with respect to FIGS. 1 to 4 may also apply to the deformable strip of material. In addition, a release liner and/or shallow pockets may also be combined with a deformable strip of material.

The present compositions may be used in combination with a delivery carrier including a dental tray and/or foam material. Dental trays are well known in the whitening art. The general process for preparing dental trays 30 is known in the art. Dentists have traditionally utilized three types of dental appliances for bleaching teeth.

The first type is a rigid appliance which is fitted precisely to the patient's dental arches. For example, an alginate impression which registers all teeth surfaces plus gingival margin is made and a cast is promptly made of the impression. If reservoirs are desired they are prepared by building a layer of rigid material on the cast on specific teeth surfaces to be treated. A dental tray is then vacuum formed from the modified cast using conventional techniques. Once formed, the tray is preferably trimmed barely shy of the gingival margin on both buccal and lingual surfaces. Enough tray material should be left to assure that all of the tooth will be covered to within about ¼ to about ⅓ mm of the gingival border upon finishing and beveling the tray periphery. One can scallop up and around interdental papilla so that the finished tray does not cover them. All tray edges are preferably smoothed so that the lip and tongue will not feel an edge prominence. The resulting tray can provide a perfect fit of the patient's teeth optionally with reservoirs or spaces located where the rigid material was placed on the cast. Dental trays may comprise of soft transparent vinyl material having a preformed thickness from about 0.1 cm to about 0.15 cm. Soft material is more comfortable for the patient to wear. Harder material (or thicker plastic) may also be used to construct the tray.

A second type of rigid custom dental appliance is an "oversized" rigid custom dental appliance. The fabrication of rigid, custom dental appliances entails fabricating cast models of the patient's dental arch impressions, and heating and vacuum-forming a thermoplastic sheet to correspond to the cast models of a patient's dental arches. Thermoplastic films are sold in rigid or semi rigid sheets and are available in various sizes and thickness. The dental laboratory fabrication technique for the oversized rigid dental appliance involves augmenting the facial surfaces of the teeth on the cast models with materials such as die spacer or light cured acrylics. Next, thermoplastic sheeting is heated and subsequently vacuum formed around the augmented cast models of the dental arch. The net effect of this method results in an "oversized" rigid custom dental appliance.

A third type of rigid custom dental appliance, used with less frequency, is a rigid bilaminated custom dental appliance fabricated from laminations of materials, ranging from soft porous foams to rigid, non-porous films. The non-porous, rigid thermoplastic shells of these bilaminated dental appliances encase and support an internal layer of soft porous foam.

A fourth type of dental tray replaces rigid custom dental appliances with disposable U-shaped soft foam trays, which may be individually packaged, and which may be saturated with a pre-measured quantity of the composition of the present invention. The soft foam material is generally an open celled plastic material. Such a device is commercially available from Cadco Dental Products in Oxnard, Calif. under the tradename VitalWhite™. These soft foam trays may comprise a backing material (e.g. a closed cell plastic backing material) to minimize the elution of the bleaching agent from the device, into the oral cavity to minimize ingestion by the patient and/or irritation of the oral cavity tissues. Alternatively, the soft foam tray is encased by a nonporous flexible polymer or the open cell foam is attached to the frontal inner wall of the dental appliance and/or the open cell foam is attached to the rear inner wall of the dental appliance. Those of ordinary skill in the art will readily recognize and appreciate, that the present compositions must be thick enough not to simply run out between the open cell structure of the foam and must be thin enough to slowly pass through the open cell foam over time. In other words, the open cell foam material has an internal structural spacing sized relative to the viscosity of the compositions to absorb and allow the composition to pass there through.

An example of a closed cell material is a closed-cell polyolefin foam sold by the Voltek division of Sekisui America Corporation of Lawrence, Mass. under the tradename Volora which is from 1/32" to 1/8" in thickness. A closed cell material may also comprise of a flexible polymeric material. An example of an opened cell material is an open celled polyethylene foam sold by the Sentinel Foam Products division of Packaging Industries Group, Inc. of Hyannis, Mass. under the tradename Opcell which is from 1/16" to 3/8" in thickness. Other open cell foam useful herein include hydrophilic open foam materials such as hydrogel polymers (e.g Medicell™ foam available from Hydromer, Inc. Branchburg, J. J.). Open cell foam may also be hydrophilic open foam material imbibed with agents to impart high absorption of fluids, such as polyurethane or polyvinylpyrrolidone chemically imbibed with various agents.

In certain aspects, the tray may have pockets built into the surface covering or contacting one or more teeth. Such pockets may help hold the oral composition in contact with the teeth. The pockets may be from about 0.05 to about 5 mm deep, preferably from about 0.1 to about 3 mm deep, more preferably from about 0.3 to about 3 mm deep, or most preferably from about 0.5 to about 1.5 mm deep. Examples of such trays include those specified in the Clinical Protocol section.

In addition, or alternatively, the fit of the tray to the teeth may have a tolerance or gap built into it on one or more teeth. Such as tolerance or gap may help hold the oral composition in contact with the teeth. The tolerance or gap may be from about 0.01 mm to about 2 mm, preferably from about 0.05 mm to about 1 mm, more preferably from about 0.1 mm to about 1 mm, or most preferably from about 0.1 mm to about 0.5 mm.

Clinical Protocol

The bleaching efficacies of compositions are measured according to the following clinical protocol. Per treatment group, 17 to 25 participants are recruited to complete the clinical study when testing compositions with less than about 1% bleaching agent, and 8 to 25 participants when testing compositions with at least about 1% bleaching agent. Recruited participants must have four natural maxillary incisors with all measurable facial sites. The mean baseline L* of the group of participants must be from 71 to 76, and the mean baseline b* of the group of participants must be from 13 to 18. In addition, participants with malocclusion on maxillary anterior teeth, severe or atypical intrinsic staining, such as that caused by tetracycline, fluorosis or hypocalcification, dental crowns or restorations on the facial surfaces of maxillary anterior teeth, self-reported medical history of melanoma, current smoking or tobacco use, light-sensitivity or a pigmentation skin disorder, self-reported tooth sensitivity, or previous tooth whitening using a professional treatment, over-the-counter kit, or investigational product, are excluded from the study. Participants are provided with take-home kits with Crest Cavity Protection toothpaste and Oral-B Indicator soft manual toothbrush (both from Procter & Gamble, Cincinnati, Ohio, USA) to be used twice a day in the customary manner.

The participants use a toothbrush ("Anchor 41 tuft white toothbrush" from Team Technologies, Inc. Morristown, Tenn., USA) to brush their teeth with water for 30 seconds prior to being treated with the composition.

The maxillary anterior teeth of the participants are treated with the composition for 60 minutes once daily using a tray with pockets as the delivery carrier. Specifically, about 0.1 ml of the composition is applied to each pocket using a syringe (BD 1 ml TB syringe with Slip-Tip REF 309659, purchased from VWR, Batavia, Ill.) on the facial surface of 8 maxillary anterior teeth of the tray (generally this translates to a total dose of about 0.7 gram per application). A trained hygienist then carefully fits the tray onto the maxillary teeth within 1 minute, taking care not to tilt the composition out of the pockets.

The tray with pockets is made using the following procedure:

An impression is taken of the maxillary arch. The impression is poured with dental stone. About 1 to 1.5 mm thick layer of block-out material (Premier Perfecta Block-out) is applied to the facial surfaces of the anterior teeth of the stone model leaving about 0.5 mm from the mesial edge. The block-out material is cured for at least 5 seconds after applying to every 2 teeth. This is repeated for all anterior teeth.

Pro-form tray material (Keystone Vacuum Forming Material Pro-form, Soft EVA 1 mm, Clear) is heated with a vacuum former. Once the material sags about 1 inch, it is pulled down on top of the stone model and held under vacuum for at least 15 seconds, cooled, and the stone model is carefully removed. The tray is then trimmed to desired fit.

Within each 60-minute treatment, the composition is re-applied to the tray every 20 minutes for a total of 3×20-minute applications. The three 20-minute applications are applied back-to-back for a total of 60 minutes per treatment, once daily.

Electromagnetic radiation is applied as follows:
1) Within each 20-minute application, a trained hygienist applies electromagnetic radiation toward the facial surfaces of the maxillary anterior teeth during the last 10 minutes.
2) The electromagnetic radiation is directed toward the maxillary anterior teeth through the tray and through the composition,
3) The tray needs to allow at least about 90% of the electromagnetic radiation from 400 nm to 500 nm to pass through, and
4) The electromagnetic radiation is delivered via four fiber-optic cables (model number M71L01 from Thorlabs, Newton, N.J., USA) connected to four high power LEDs with a peak intensity wavelength of 455 nm (model number M455F1 from Thorlabs, Newton, N.J., USA) as shown in FIG. 6. The four LEDs are run at 1000 mA each using an LED Driver and Hub (model numbers DC4104 and DC4100-HUB from Thorlabs, Newton, N.J., USA). The exit ends of the four fiber-optic cables are mounted behind a transparent mouthpiece to help position the electromagnetic radiation reproducibly against the outer surface of the strip. The exit ends of the four fiber-optic cables are about 7 mm away from the exit surface of the mouthpiece with the electromagnetic radiation passing through the transparent mouthpiece. The bite-shelf of the mouthpiece is offset such that the transparent window through which the electromagnetic radiation passes toward the maxillary anterior teeth is 7.4 mm high. Also, the transparent window through which the electromagnetic radiation passes toward the maxillary anterior teeth is 40 mm long measured linearly from end to end (not including the curvature). The exit ends of the fiber-optic cables are positioned and angled such that the cones of electromagnetic radiation exiting from the fiber-optic cables are centered within the transparent window through which the electromagnetic radiation passes toward the maxillary anterior teeth as shown in FIG. 6. Also, the exit ends of the four fiber-optic cables are spaced such that the cones of electromagnetic radiation are spaced across the length of the transparent window through which the electromagnetic radiation passes toward the maxillary anterior teeth as shown in FIG. 6. The intensity of the electromagnetic radiation from 400 nm to 500 nm measured at the central axis of each cone of electromagnetic radiation exiting at the exit surface of the transparent window through which the electromagnetic radiation passes toward the maxillary anterior teeth needs to be from about 175 $mW/cm^2$ to about 225 $mW/cm^2$ as measured by the method disclosed herein.

Once 60 minutes of the treatment with the composition is completed, the tray is removed. This treatment is applied once daily for a minimum of 7 days for compositions with less than about 1% bleaching agent, and a minimum of 3 days for compositions with at least about 1% bleaching agent.

The change in tooth color due to the treatment with the composition is measured using the procedure described below the day after the $7^{th}$ treatment for compositions with less than about 1% bleaching agent and the day after the $3^{rd}$ treatment for compositions with at least about 1% bleaching agent.

Tooth color is measured using a digital camera having a lens equipped with a polarizer filter (Camera model no. CANON EOS 70D from Canon Inc., Melville, N.Y. with NIKON 55 mm micro-NIKKOR lens with adapter). The light system is provided by Dedo lights (model number DLH2) equipped with 150 watt, 24V bulbs model number (Xenophot model number HL X64640), positioned about 30 cm apart (measured from the center of the external circular surface of one of the glass lens through which the light exits to the other) and aimed at a 45 degree angle, such that the light paths intersect at the vertical plane of the chin rest about 36 cm in front of the focal plane of the camera. Each light has a polarizing filter (Lee 201 filter), and a cutoff filter (Rosco 7 mil Thermashield filter from Rosco, Stamford, Conn., USA).

At the intersection of the light paths, a fixed chin rest is mounted for reproducible repositioning in the light field. The camera is placed between the two lights such that its focal plane is about 36 cm from the vertical plane of the chin rest. Prior to beginning the measurement of tooth color, color standards are imaged to establish calibration set-points. A Munsell N8 grey standard is imaged first. The white balance of the camera is adjusted, such that the RGB values of grey are 200. Color standards are imaged to get standard RGB values of the color chips. The color standards and grey standard are listed below (from Munsell Color, Division of X-rite, Grand Rapids, Mich., USA). Each color standard is labeled with the Munsell nomenclature. To create a grid of color standards they can be arranged in the following manner. This enables multiple color standards to be contained in a single image captured of the grid of color standards.

| Color standard grid 1 | | | | | |
|---|---|---|---|---|---|
| 7.5R 6 8 | 2.5R 6 10 | 10YR 6.5 3 | POLARIZATION CHECK | 5R 7 8 | N 3.5 0 |
| 7.5RP 6 6 | 10R 5 8 | 5YR 7 3 | 2.5Y 8.5 2 | 2.2YR 6.47 4.1 | 7.5YR 7 4 |
| 5YR 8 2 | N 8 0 | 10R 7 4 | N 8 0 | 5YR 7.5 2.5 | 2.5Y 8 4 |
| 5YR 7 3.5 | 5YR 7 2.5 | 5YR 5 2 | 5YR 7.5 2 | N 6.5 0 | N 9.5 0 |

| Color standard grid 2 | | | | | |
|---|---|---|---|---|---|
| 5YR 7.5 3.5 | 2.5Y 6 4 | 10YR 7.5 3.5 | 2.5R 7 8 | 7.5R 7 8 | 10YR 7.5 2 |
| 10YR 7.5 2.5 | N 5 0 | 2.5R 6 8 | 10YR 7 2 | 5R 7 4 | 10YR 7 2.5 |
| N 6.5 0 | 7.5RP 6 8 | 7.5R 8 4 | 5Y 8 1 | 7.5YR 8 2 | 2.2YR 6.47 4.1 |
| N 5 0 | 2.5Y 8 4 | 10YR 7 3 | N 9.5 0 | 10RP 7 4 | 2.5Y 7 2 |

| Color standard grid 3 | | | | | |
|---|---|---|---|---|---|
| 5R 6 10 | N 8.5 0 | 10YR 6.5 3.5 | 10RP 6 10 | N 8 0 | 7.5YR 7 3 |
| 2.5Y 3.5 0 | 10YR 7 3.5 | 5Y 8.5 1 | 5YR 8 2.5 | 5YR 7.5 3 | 5R 5 6 |
| 10YR 7.5 3 | 5YR 6.5 3.5 | 2.5YR 5 4 | 2.5Y 8 2 | 10YR 8 2 | 2.5Y 7 2 |
| 2.5R 6 6 | 5R 7 6 | 10YR 8 2.5 | 10R 5 6 | N 6.5 0 | 7.5YR 8 3 |

For baseline tooth color, participants use a toothbrush ("Anchor 41 tuft white toothbrush" from Team Technologies, Inc. Morristown, Tenn., USA) to brush their teeth with water to remove debris from their teeth. Each participant then uses cheek retractors (from Washington Scientific Camera Company, Sumner, Wash., USA; treated with at frosted matte finish at A&B Deburring Company, Cincinnati, Ohio, USA) to pull the cheeks back and allow the facial surfaces of their teeth to be illuminated. Each participant is instructed to bite their teeth together such that the incisal edges of the maxillary incisors contact the incisal edges of the mandibular incisors. The participants are then positioned on the chin rest at the intersection of the light paths in the center of the camera view and the tooth images are captured. After all participants are imaged, the images are processed using image analysis software (Optimas manufactured by Media Cybernetics, Inc. of Silver Spring, Md.). The central four incisors are isolated and the average RGB values of the teeth are extracted.

After the participants have used a whitening product, but prior to capturing participant's tooth images, the system is set to the baseline configuration and calibrated as previously discussed. After calibration, each participant is imaged a second time using the same procedure as before making sure the participant is in the same physical position as the pre-treatment image including orientation of the teeth. The images are processed using the image analysis software to obtain the average RGB values of the central four maxillary incisors. The RGB values of all of the images are then mapped into CIE L*a*b* color space using the RGB values and the L*a*b* values of the color chips on the color standard. The L*a*b* values of the color chips on the color standard are measured using a Photo Research SpectraScan PR650 from Photo Research Inc., LA using the same lighting conditions described for capturing digital images of the facial dentition. The PR650 is positioned the same distance from the color standards as the camera. Each chip is individually measured for L*a*b* after calibration according to the manufacturer's instructions. The RGB values are then transformed into L*a*b* values using regression equations such as:

$$L^* = 25.16 + 12.02*(R/100) + 11.75*(G/100) - 2.75*(B/100) + 1.95*(G/100)^3$$

$$a^* = -2.65 + 59.22*(R/100) - 50.52*(G/100) + 0.20*(B/100) - 29.87*(R/100)^2 + 20.73*(G/100)^2 + 8.14*(R/100)^3 - 9.17(G/100)^3 + 3.64*[(B/100)^2]*[R/100]$$

$$b^* = -0.70 + 37.04*(R/100) + 12.65*(G/100) - 53.81*(B/100) - 18.14*(R/100)^2 + 23.16*(G/100)*(B/100) + 4.70*(R/100)^3 - 6.45*(B/100)^3$$

The $R^2$ for L*, a*, and b* should be >0.95. Each study should have its own equations.

These equations are generally valid transformations in the area of tooth color (60<L*<95, 0<a*<14, 6<b*<25). The data from each participant's set of images is then used to calculate product whitening performance in terms of changes in L*, a* and b*—a standard method used for assessing whitening benefits. When evaluating compositions with less than about 1% bleaching agent: Changes in L* is defined as $\Delta L^* = L^*_{day\ after\ 7\ treatments} - L^*_{baseline}$ where a positive change indicates improvement in brightness; Changes in a* (red-green balance) is defined as $\Delta a^* = a^*_{day\ after\ 7\ treatments} - a^*_{baseline}$ where a negative change indicates teeth which are less red; Changes in b* (yellow-blue balance) is defined as $\Delta b^* = b^*_{day\ after\ 7\ treatments} - b^*_{baseline}$ where a negative change indicates teeth are becoming less yellow. When evaluating compositions with at least about 1% bleaching agent: Changes in L* is defined as $\Delta L^* = L^*_{day\ after\ 3\ treatments} - L^*_{baseline}$ where a positive change indicates improvement in brightness; Changes in a* (red-green balance) is defined as $\Delta a^* = a^*_{day\ after\ 3\ treatments} - a^*_{baseline}$ where a negative change indicates teeth which are less red; Changes in b* (yellow-blue balance) is defined as $\Delta b^* = b^*_{day\ after\ 3\ treatments} - b^*baseline$ where a negative change indicates teeth are becoming less yellow. $-\Delta b^*$ is used as the primary measure of bleaching efficacy. The overall color change is calculated by the equation $\Delta E = (\Delta L^{*2} + \Delta a^{*2} + \Delta b^{*2})^{1/2}$.

After using the whitening products, color changes in CIE Lab color space can be calculated for each participant based on the equations given.

To validate the above clinical protocol, the bleaching efficacy (calculated as $-\Delta b^*$) of Example I-B made according to the procedure specified herein (delivered on a tray with pockets and used with electromagnetic radiation as disclosed herein) needs to be measured the day after the 3$^{rd}$ treatment and demonstrated to be >3

Preparation of the Present Multi-Phase Oral Care Compositions

Preparation of emulsions is well known in the art and any suitable manufacturing process can be used to make the multi-phase oral care compositions which may be in the form of an emulsion; see for example, Remington: the Science and Practice of Pharmacy, 19$^{th}$ ed., Vol. II, Chapters 20, 80, 86, etc. Generally, the components are separated into those that are oil-soluble and those that are water-soluble.

These are dissolved in their respective solvents by heating if necessary. The two phases are then mixed and the product is stirred and cooled. After combining the phases, the present multi-phase oral care compositions, which may be in the form of emulsions may be agitated or sheared by various methods, including shaking, intermittent shaking, high shear mixing, or by using high speed mixers, blenders, colloid mills, homogenizers, or ultrasonic techniques. Depending on the specific ingredients, it may be recognized by one of skill in the art that certain modifications may need to be made to the manufacturing process to accommodate the specific properties of the ingredients. The type of multi-phase oral care composition prepared may be observed using a microscope. Further description of test methods are disclosed in *Remington: The Science and Practice of Pharmacy*, 19$^{th}$ ed., volume 1, 1995, pp. 282-283.

In certain aspects, multi-phase oral care compositions, which may be in the form of a jammed oil-in-water emulsion, as disclosed herein may be made as follows:

1) The water-soluble ingredients are dissolved in the aqueous phase, and the oil-soluble components in the hydrophobic phase.
2) The hydrophobic phase is added to the aqueous phase in portions in a SpeedMixer container with thorough mixing (with a rubber spatula for about 1 to 2 minutes for example, depending on the size of the batch) between portions. Ideally, 1) the size of the initial portion is less than 20% of the amount aqueous phase, 2) the size of subsequent portions may be increased gradually toward the amount of aqueous phase, and 3) the size of each portion is less than the amount of aqueous phase. As the jamming concentration is approached, an oil-in-water emulsion forms during this step, and the composition develops a lotion-like semi-solid consistency—this is evidence that the droplets of the hydrophobic phase are jammed against each other and deform each other (note, they are still separated by a region of aqueous phase). This jamming is evidenced by the development of a lotion-like consistency of the composition.
3) Once all the hydrophobic phase has been incorporated, the contents of the Speedmixer container are mixed 3 times at 800 RPM for 2 minutes each time in a Speedmixer.

Note, in certain aspects, 1) it may be possible to add the hydrophobic phase to the aqueous phase at a suitably slow but continuous or pulsed rate with concurrent mixing in step-2 above, and 2) the mixing in step-3 above may be accomplished with other types of mixers over various lengths of time, such as a recirculation loop through static mixers, rotor-stator mixers, or other mixing devices, such as those described in the Handbook of Industrial Mixing.

The mixing procedure of the SpeedMixer™ series is based on the double rotation of the mixing cup using a dual asymmetric centrifugal mixing. This combination of centrifugal forces acting on different levels enables very rapid mixing of the entire cup. Optionally the composition may be heated, if necessary, to facilitate mixing. When the active is included in solid particulate form, the addition of an optional viscosity modifier, may be appropriate to keep the particulate dispersed and suspended within the composition. Flavorants or sweeteners may also be added to one of the phases of the composition, as desired. Thereafter the composition may be added to the delivery carrier, as desired.

Methods of Using the Compositions and/or Delivery Systems

The present invention can be applied to the teeth of a consumer in the dental office by a dental professional, or the present invention can be applied at home by the consumer. Generally, the recommended treatment period is a sufficient period of time to achieve whitening.

In practicing the present invention, the patient applies the multi-phase oral care composition or jammed oil-in-water emulsion, as described herein, that contains the bleaching agent to obtain the desired effect, such as, whitening, to one or more teeth. The composition can be applied with a paint-on device, a syringe or unit dose syringe, squeezable tube, a brush, a pen or brush tip applicator, a doe's foot applicator, swab, lip gloss applicator, strip that is removed after application, tray that is removed after application, or the like, or even with the fingers. The composition can also be combined with a delivery carrier, such as a strip of material, a dental tray, or a sponge material, and thereafter applied to the teeth. In certain aspects, the compositions or delivery systems herein are almost unnoticeable when applied to the teeth. After a desired period of time has elapsed, any residual composition may be easily removed by wiping, brushing or rinsing the oral surface.

In general, it is not necessary to prepare the teeth before applying the present composition. For example, the patient may choose to brush the teeth or rinse the mouth before applying the compositions of the present invention, but the surfaces of the oral cavity are neither required to be clean, to be dried, nor to be excessively wet with saliva or water before the application. However, it is believed that adhesion to the tooth enamel surfaces can be improved if the teeth are dry prior to application.

Dental tray appliances may be used as follows. The patient or dental professional dispenses the present composition into a soft or rigid dental appliance and then the participant places the appliance over the participant's dental arch (or fits the device around his or her teeth to keep the tray in position). Generally, the recommended treatment period is a sufficient period of time to achieve whitening as disclosed above. At the end of the treatment period, the dental appliance is removed, cleaned with water to remove any remaining composition, and then stored until the next application.

The described compositions and delivery systems, described herein, may be combined in a kit which comprises: 1. present composition and 2. instructions for use; or which comprises: 1. present composition, 2. instructions for use, and 3. a delivery carrier. In addition, if the tooth shall be radiated by electromagnetic radiation, the kit may further comprise an electromagnetic radiation source of the appropriate wavelength and instruction for use, so that the kit can be used by consumers in a convenient manner.

Optional Electromagnetic Radiation Treatment

The multi-phase oral care composition as disclosed herein may be used to whiten teeth and/or removing stain from tooth surfaces. In addition, the bleaching efficacy may be further increased by directing electromagnetic radiation of a suitable wavelength toward at least one tooth. A suitable wavelength may be any wavelength, which corresponds to a maximum absorption band of the tooth and/or the tooth stain to be bleached. For example, the multi-phase oral care composition may be radiated with an electromagnetic radiation with one or more wavelengths in the range of from about 200 nm to about 1200 nm. The electromagnetic radiation may be directed toward at least one tooth. In addition, more than one tooth may be irradiated. For example, the electromagnetic radiation may have a peak intensity at one or more wavelengths in the range of from about 1 nm to about 750 nm, from about 200 nm to about 700 nm, from about 300 nm to about 700 nm, from about 400 nm to about 600 nm, from about 400 nm to about 500 nm, or up to about 750 nm. Additionally, the electromagnetic radiation may have a peak intensity at one or more wavelengths in the range of from about 400, 405, 410, 415, 420, 425, 430, 435, 440, or 445, 446 nm to about 450, 455, 460, 465, 470, 475, 480, 481, 485, 490, 495, or 500 nm or any other numerical range, which is narrower and which falls within such broader numerical range, as if such narrower numerical ranges were all expressly written herein. The electromagnetic radiation can have a peak intensity at a wavelength in the range of from about 425 nm to about 475 nm, from about 445 nm to about 465 nm, or wherein the peak intensity wavelength of the electromagnetic radiation is similar to the wavelength at which the stain absorbs the most electromagnetic radiation. Electromagnetic radiation may be directed toward at least one tooth for partial or whole wearing time of the composition; or after the composition has been removed from the tooth. Electromagnetic radiation may be applied at least for a sufficient period of time for whitening, e.g. for at least about 1 minute, for at least about 5 minutes, or for at least about 10 min. The electromagnetic radiation may be applied using the procedure disclosed in US 2013/0295525. Preferably the multi-phase oral care composition as disclosed herein is applied to at least one tooth and maintained on the at least one tooth for a first period of time; after the first period of time electromagnetic radiation is directed toward the at least one tooth for a second period of time, wherein the first period of time has a duration greater than 50%, preferably 80% of a total duration of the first and second periods of time; and finally, the multi-phase oral care composition is removed from the at least one tooth. Suitable sources of electromagnetic radiation include the sources described herein.

The multi-phase oral care compositions as disclosed herein may be transparent or translucent to electromagnetic radiation with wavelengths from about 400 nm to about 500 nm. In certain aspects, the multi-phase oral care compositions as disclosed herein when applied in a thickness of from about 0.0001, 0.001, or 0.01 cm to about 0.01, 0.1, or 0.5 cm thick allow from about 10%, 20%, or 30% to about 40%, 50%, 60%, 70%, 80%, 90%, or 100% of electromagnetic radiation at one or more wavelengths in the range of from about 1 nm to about 750 nm, from about 200 nm to about 700 nm, from about 300 nm to about 700 nm, from about 400 nm to about 600 nm, from about 400 nm to about 500 nm, or up to about 750 nm to pass through, as measured by a spectrophotometer. When a multi-phase oral care composition is applied in a thickness of about 0.1 cm, from about 80% to about 100% of electromagnetic radiation from about 400 nm to about 500 nm can pass through, as measured by a spectrophotometer. The multi-phase oral care compositions, as disclosed herein, may when applied in an amount from about 0.0001, 0.001, or 0.01 grams to about 0.01, 0.1, 1, or 5 grams, on a delivery carrier or tray with a surface area from about 5 cm$^2$ to about 20 cm$^2$, allow from about 10%, 20%, or 30% to about 40%, 50%, 60%, 70%, 80%, 90%, or 100% of electromagnetic radiation from about 400 nm to about 500 nm to pass through.

The electromagnetic radiation impinging on the surface of the tooth or outer surface of the carrier, which may be a strip or tray, at one or more wavelengths in the range of from about 1 nm to about 750 nm, from about 200 nm to about 700 nm, from about 300 nm to about 700 nm, from about 400 nm to about 600 nm, from about 400 nm to about 500 nm, or up to about 750 nm. may range in intensity from about 5, 10, 25, 50, 75, or 100 mW/cm$^2$ to about 10000, 5000, 2000, 1000, 500, 250, 225, 205, 200, 175, 150, 125, 100, 75, 50, 25, 10, or 5 mW/cm$^2$ or any other numerical range, which is narrower and which falls within such broader numerical range, as if such narrower numerical ranges were all expressly written herein.

The intensity of the electromagnetic radiation can be measured using a spectrometer (USB 2000+ from Ocean Optics) connected to a UV-VIS 200 micron fiber-optic cable with a cosine corrector at the tip (OP 200-2-UV-VIS from Ocean Optics). The spectrometer is connected to a computer running the spectrometer software (Oceanview 1.3.4 from Ocean Optics). The tip of the fiber-optic cable is held pointing toward the light source at the location where the light intensity is to be measured. The photons collected at the detector surface are guided via the fiber-optic cable to the charge-coupled device in the spectrometer (CCD). The CCD counts photons arriving to the CCD during a pre-determined time period at each wavelength from 200 nm to 1100 nm, and uses a software algorithm to convert these photon counts to spectral irradiance (mW/cm$^2$/nm). The spectral irradiance is integrated from 200 nm to 1100 nm by the software to yield the Absolute Irradiance (mW/cm$^2$), which is the intensity of electromagnetic radiation from 200 nm to 1100 nm. The spectral irradiance is integrated from 400 nm to 500 nm by the software to yield the Absolute Irradiance (mW/cm$^2$), which is the intensity of electromagnetic radiation from 400 nm to 500 nm.

For consumer convenience, the multi-phase oral care composition as disclosed herein may be provided as a Kit comprising the bleaching composition as disclosed herein, a delivery carrier for easier application, an electromagnetic radiation source emitting electromagnetic radiation in a suitable wavelength, and instructions for use.

The electromagnetic radiation source emitting electromagnetic radiation in a suitable wavelength can be a device capable of producing electromagnetic radiation, such as the devices described in U.S. Pat. No. 10,099,064, or curing lights used in dental offices, or devices similar to that described in the clinical protocol section specified herein.

The compositions of this invention are useful for both human and other animals (e.g. pets, zoo, or domestic animals) applications.

Methods

Method to Measure the Two-Dimensional Density of Droplets of Aqueous Phase or the Two-Dimensional Density of Regions of Hydrophobic Phase of a Multi-Phase Oral Care Composition 1. Use a small spatula and place a small sample of the composition on a glass microscope slide (VWR Micro Slides, Super Frost Plus, 25×75×1 mm, manufactured by VWR International, Radnor, Pa.; purchased from VWR, Batavia, Ill., catalog number 48311-703). The amount of sample should be such that after it has been pressed down per step 2, at least about 100 square millimeters of the slide are completely covered with the composition and can be measured. Take care to place the sample as a single blob on the adhesive grid sticker—this helps minimize air-entrapment when the coverslip is placed over it.
2. Place a coverslip (VWR Microscope Cover Glasses, 22×22 mm, purchased from VWR, Batavia, Ill., catalog number 16004-094) over the sample-composition and press down (if needed) until the sample-composition is about 120 microns thick. Spacers (Electron Microscopy Sciences, Hatfield Pa., Cat. 70327-20S or 70327-13S) may be used to control the thickness.

3. Place the microscope slide on a microscope and focus on the sample using light transmitted through the sample. Use a microscope and a magnification level that enable the measurement of the cross-sectional area of droplets of aqueous phase or regions of hydrophobic phase larger than the specified value.
4. Count the number of droplets of aqueous phase or regions of hydrophobic phase whose cross-sectional area at the two-dimensional focal plane is larger than the specified value. Take care not to count residual air-bubbles (unlike droplets of aqueous phase or regions of hydrophobic phase, air bubbles may be identified by thick dark walls in the field of view).
5. The "two-dimensional density of droplets of aqueous phase" or "two-dimensional density of regions of hydrophobic phase" with a cross-sectional area larger than a specified value (expressed as number of droplets of aqueous phase per square centimeter or number of regions of hydrophobic phase per square centimeter) for this slide is calculated as: The number of droplets of aqueous phase or the number of regions of hydrophobic phase whose cross-sectional area at the two-dimensional focal plane is larger than the specified value measured in this slide DIVIDED by the total area of the slide covered by the composition expressed in square centimeters.
6. Repeat steps 1 to 5 for a total of at least twelve slides. Average the calculation from step 5 across all the slides measured. This is the final "two-dimensional density of droplets of aqueous phase" or "two-dimensional density of regions of hydrophobic phase" with a cross-sectional area larger than a specified value (expressed as number of droplets of aqueous phase per square centimeter or number of regions of hydrophobic phase per square centimeter).

Method to Measure the Dv 50, D[4,3], and D[3,2] of Regions of Hydrophobic Phase of a Multi-Phase Oral Care Composition
1. Weigh 0.20 g (+/−0.02 g) of the sample to be tested into a 20 ml HDPE scintillation vial (VWR 66021-690).
2. Add water (for example WFI Quality OmniPur Sterile Filtered CAS #7732-18-5) 19.80 g (+/−0.02 g) to the vial and secure cap.
3. Roll the vial on a countertop gently until the sample to be tested is dispersed throughout the water. Avoid shaking or mixing vigorously.
4. Set up the Mastersizer 3000 (Malvern Panalytical Inc., Westborough, Mass.) and the Hydro unit (Model #MAZ3210), and ensure the hoses are securely attached.
5. Add water (for example MilliporeSigma Ultrapure Lab water system) to the lowest edge of silver rim and initialize the system (this measures the background).
6. When the system is ready, roll the vial gently about 4 or 5 times to mix the contents, and then slowly pipet contents of the vial (generally from about 0.1 gram to about 5 grams) using a 1.7 ml pipet (VWR #414004-031) into the Hydro unit until Obscuration is in range to be measured (1-10%). If the obscuration % is >10%, remove some of the sample solution from the vessel and add water (for example MilliporeSigma Ultrapure Lab water system) until Obscuration is less than 10%.
7. Start testing. Testing is done for 10 measurements and the sample is flushed upon completion. Stirrer speed is set at 500 rpm.
8. Add water when indicated for rinsing the system between samples (water is added generally about 5 to 6 times)
9. Repeat testing 2 more times with rinses in between.
10. Record the average Dv 50, D[4,3], and D[3,2] for each set of data (10 measurements×3 replications).

Additional information on the use of the Mastersizer 3000 can be found in the user manual (MAN0474 MRK1953-0 on the website malvernpanalytical.com).

To validate the above method, the D[4,3] of Example I-B made according to the procedure specified herein must be measured and demonstrated to be from 15 microns to 30 microns.

Method to Measure the Water-Dispersibility of a Multi-Phase Oral Care Composition
1. Allow the multi-phase oral care composition and sterile filtered water (Calbiochem catalog number 4.86505.1000 from EMD Millipore Corporation, Billerica, Mass.) to equilibrate at the desired temperature for at least 12 hours.
2. Record the tare weight of the bottom portion of a petri dish (VWR, Polystyrene, 100 mm×15 mm, catalog number 25384-342, purchased from VWR, Batavia, Ill.).
3. Weigh 0.30 to 0.35 gram of the multi-phase oral care composition into the center of the petri dish in one single blob. Record the initial weight of the sample.
4. Add 30 ml of sterile filtered water to the petri dish without disturbing the sample—with a syringe (30 ml BD Syringe with Luer Lok tip, item number 302832), taking care to go around the edges of the petri dish and directing the stream away from the sample.
5. After 10 minutes, decant the contents of the petri dish, dry it in an oven set at 60 C for at least 60 minutes, allow it to cool, and record the weight of petri dish+residual sample.
6. Calculate:

Weight of residual sample=(Weight of petri dish+residual sample from step-5) MINUS (Tare weight of petri dish from step-2)

7. Calculate:

Water-dispersibility=100 MINUS [100×(Weight of residual sample from step-6)/(Initial weight of sample from step-3)]

8. Repeat steps-1-7 for a total of at least 3 measurements. Calculate the average. This is the water-dispersibility of the multi-phase oral care composition.

To validate the above method, the water-dispersibility of 1) Example I-B made according to the procedure specified herein must be measured and demonstrated to be from 60 to 100%, and 2) Comparative Example VI and Comparative Example VII made according to the procedure specified herein must be measured and demonstrated to be from 0 to 10%.

Method to Measure the Mean and Standard Deviation of the Peroxide Concentration of a Multi-Phase Oral Care Composition Smeared onto Peroxide Test Strips
1. Weigh 0.60 to 0.80 gram of the composition onto the end of a clean hard rubber spatula (4" long blade, from VWR, Batavia, Ill. 60510, USA., catalog number 57930-025).
2. Take a fresh peroxide test strip (EMD Millipore Corporation, Billerica, Mass., supplier number 1.16974.0001; purchased from VWR, Batavia, Ill., catalog number EM1.16974.0001) out of the container, and start a timer.
3. Take a digital image of the peroxide test strip. The equipment and system configuration used to take the digital image of the test strip are specified herein. Place the peroxide test strip on a fresh paper towel.

4. Hold the spatula and peroxide test strip. Smear the composition (pre-weighed in step-1) with firm pressure from left to right onto both reaction-zones on the test strip. Repeat the smearing motion a total of three strokes from left to right with the same sample of composition that has already been pre-weighed onto the spatula.
5. Move the peroxide test strip to a clean area of the paper towel. Place a filter paper (Whatman Grade 1 Qualitative Filter Paper Standard Grade, circle, 90 mm, supplier number 1001-090; from VWR, Batavia, Ill. 60510, USA., catalog number 28450-081) on top of the test strip. Apply finger pressure on top of the filter paper. Pull the peroxide test strip out from under the filter paper (while maintaining finger pressure on the filter paper) in a single stroke such that excess gel is wiped off onto the filter paper and paper towel. Make sure the reaction-zones do not get dislodged from the peroxide test strip.
6. Take a digital image of the peroxide test strip. The equipment and system configuration used to take the digital image of the test strip are specified herein.
7. Steps 2 to 6 should be completed within 90 seconds on the timer.
8. Repeat steps 1 to 7 for a total of at least eighteen peroxide test strips.
9. Use Adobe Photoshop CS4 with the procedure specified herein to measure the mean and standard deviation of the Red intensities of the strip of Munsell N8 Matte Color sheet attached to the holder that serves as a built-in Munsell N8 reference within each image. The mean R value intensity of the built-in Munsell N8 reference within each image should be from 204 to 212 and the standard deviation should be no more than 3.
10. Use Adobe Photoshop CS4 with the procedure specified herein to measure the mean and standard deviation of the Red intensities of each reaction-zone on all peroxide test strips at BASELINE (before smearing with the composition).
11. Use Adobe Photoshop CS4 with the procedure specified herein to measure the mean and standard deviation of the Red intensities of each reaction-zone on all peroxide test strips AFTER smearing with the composition.
12. The mean peroxide concentration of the composition smeared on peroxide test strips is calculated as follows: First, calculate the mean baseline R value intensity of each reaction-zone from step-10 MINUS the mean R value intensity of the same reaction-zone after smearing with the composition from step-11. Repeat this calculation for all reaction-zones, and average the results across all reaction-zones on all peroxide test strips. This is the mean peroxide concentration of the composition smeared on peroxide test strips.
13. The standard deviation of the peroxide concentration of the composition smeared on peroxide test strips is calculated as: Average the standard deviation of the Red intensities across all reaction-zones on all peroxide test strips AFTER they have been smeared with the composition from step-11. This is the standard deviation of the peroxide concentration of the composition smeared on peroxide test strips.

To validate the equipment, system configuration, and method specified herein, the mean and standard deviation of the Red intensities of a Munsell N8 Matte Color sheet (from Munsell Color, Division of X-rite, Grand Rapids, Mich., USA) needs to be measured and demonstrated to be from 204 to 212 for the mean and no more than 3 for the standard deviation.

Equipment to Take Digital Images of Peroxide Test Strips

1—Digital camera capable of capturing images at 18 million pixels (5184×3456) resolution jpg image and capable of a shutter speed of $1/1250^{th}$ of a second (such as Canon 60D camera from Canon USA Inc., Lake Success, N.Y. 11042)
1—Memory card
1—Lens adapter if needed (such as Canon body to Nikon lens adapter)
1-105 mm lens (such as 105 mm Micro Nikkor lens from Nikon USA Inc. Melville, N.Y. 11747)
1-52 mm Flash adapter ring
1—Macro ring lite with polarization filter attached (such as Canon MR-14EX Macro ring lite with polarization filter attached from Canon USA Inc., Lake Success, N.Y. 11042)
1-52 mm Rotating Circular Polarizer on the lens
1—Tripod
1—Sheet Munsell N8 Matte Color sheet (from Munsell Color, Division of X-rite, Grand Rapids, Mich., USA)
1—Holder for the peroxide test strips made using DGK Plastic Gray card XL (from DGK Color Tools on Amazon.com) as the background, and a strip of Munsell N8 Matte Color sheet attached to serve as a built-in Munsell N8 reference within each image.
1—mm scale mounted to a blank specimen strip System Configuration to Take Digital Images of Peroxide Test Strips 1. The tripod is configured with the tripod mount attached to the underside of the tripod to accommodate macro photography, with the camera pointing down toward the table. The subject plane is 317 mm from the sensor plane.
2. The Nikon 105 mm lens is attached to the Canon 60D camera body using the Canon to Nikon adapter mount.
3. The rotating polarizer is attached to the 105 mm Micro Nikkor lens.
4. The 52 mm flash adapter ring is attached to the front of the 105 mm lens.
5. The Canon MR-14EX Macro ring lite with polarization filter is attached to the front of the lens to the flash adapter ring.
6. The rotating circular polarizer on the lens is rotated until the maximum gloss/glare is removed and complete cross polarization is achieved.
7. The flash is set to 'manual' mode with the power setting set to ⅛ power.
8. The Canon 60D camera is set to 'manual' mode with the ISO set to 100.
9. The Shutter is set to $1/250^{th}$ of a Second.
10. The aperture is set at f=8 on the 105 mm Micro Nikkor lens.
11. Manual Focus is used on the 105 mm Micro Nikkor lens with the focus to 317 mm distance from the sensor plane to the subject plane.
12. A mounted sheet of calibrated Munsell N8 material is used to achieve White Balance for the images.
13. The camera is set to capture images at the 18 million pixels (5184×3456) resolution jpg image.
14. The total exposure setting for the camera and flash needs to be configured such that a captured image of the Munsell N8 Matte Color sheet has a mean R value intensity of 204 to 212 and a standard deviation of no more than 3 measured using the procedure specified herein.

Procedure in Adobe Photoshop CS4 to Measure the Mean and Standard Deviation of the Red Intensities
1. Open Adobe Photoshop CS4.
2. On the top edge of the screen select "Window", followed by "Histogram". This displays the histogram of the image. In the Histogram window, select "Expanded view" and "Show statistics". This displays the histogram with statistics. Make sure the "Channel" is set to "Red". In Adobe Photoshop CS4, a histogram panel displays the tonal range of an image. It shows how the pixels are distributed by graphing the number of pixels at each of the 256 intensity levels from 0-255 in the region of interest selected. Pixels with the same intensity level are stacked in bars along the vertical axis. The higher the bar the greater number of pixels at that intensity level. The vertical bars toward the right side of the histogram indicate pixels with higher intensities, while bars toward the left side of the histogram indicate pixels with lower intensities.
3. The mean and standard deviation of the Red intensities of the Munsell N8 Matte Color sheet is measured as follows: Open a captured image of the Munsell N8 Matte Color sheet using Adobe CS4. On the left edge of the screen, select the "Rectangular Marquee Tool". On the top edge of the screen, set "Feather" to 0 px, "Style" to Fixed size, "Width" to 5000 px, and "Height" to 3300 px. This defines a rectangle containing 16500000 pixels whose size & shape matches the size & shape of images of the Munsell N8 Matte Color sheet. Select the image of the Munsell N8 Matte Color sheet using the "Rectangular Marquee Tool". Make sure the edges of the rectangle are within the edges of the image of the Munsell N8 Matte Color sheet. Click the circular symbol on the Histogram panel and make sure "Cache Level" reads 1 in the Histogram panel. This measures and displays the mean and standard deviation of the Red intensities the Munsell N8 Matte Color sheet. Record these values.
4. The mean and standard deviation of the Red intensities of the built-in Munsell N8 reference within each image is measured as follows: Open a captured image of the built-in Munsell N8 reference within each image using Adobe CS4. On the left edge of the screen, select the "Rectangular Marquee Tool". On the top edge of the screen, set "Feather" to 0 px, "Style" to Fixed size, "Width" to 5000 px, and "Height" to 800 px. This defines a rectangle containing 4000000 pixels whose size & shape matches the size & shape of the built-in Munsell N8 reference within each image. Select the built-in Munsell N8 reference within each image using the "Rectangular Marquee Tool". Make sure the edges of the rectangle are within the edges of the built-in Munsell N8 reference within each image. Click the circular symbol on the Histogram panel and make sure "Cache Level" reads 1 in the Histogram panel. This measures and displays the mean and standard deviation of the Red intensities of the built-in Munsell N8 reference within each image. Record these values.
5. The mean and standard deviation of the Red intensities of each reaction-zone on the peroxide test strip is measured as follows: Open a captured image of the peroxide test strip using Adobe CS4. On the left edge of the screen, select the "Rectangular Marquee Tool". On the top edge of the screen, set "Feather" to 0 px, "Style" to Fixed size, "Width" to 1300 px, and "Height" to 1750 px. This defines a rectangle containing 2275000 pixels whose size & shape matches the size & shape of images of each reaction-zone on the peroxide test strip. Select one of the two reaction-zones on the peroxide test strip using the "Rectangular Marquee Tool". Make sure the edges of the rectangle are within the edges of the reaction-zone. Click the circular symbol on the Histogram panel and make sure "Cache Level" reads 1 in the Histogram panel. This measures and displays the mean and standard deviation of the Red intensities of one of the two reaction-zones on the peroxide test strip. Record these values.

Method to Measure the Brookfield Viscosity of a Multi-Phase Oral Care Composition or Hydrophobic Phase
1. Transfer 40 to 50 ml of the multi-phase oral care composition or hydrophobic phase into a 50 ml polypropylene conical tube (Falcon brand catalog number REF 352098, Corning Science, Tamaulipas, Mexico). If the multi-phase oral care composition or hydrophobic phase exhibits macroscopic separation of one or more components prior to transferring into the conical tube, mix the multi-phase oral care composition or hydrophobic phase in a Speedmixer (for example at 800 RPM for 2 minutes) and transfer into the conical tube before it exhibits macroscopic separation of one or more components. If the multi-phase oral care composition or hydrophobic phase has macroscopic air-bubbles or voids: 1) Tap the conical tube on a hard surface or mix the conical tube on a vortex mixer (for example Vortex Genie 2 from Scientific Industries Inc. Bohemia, N.Y., or Mini Vortexer from VWR Scientific Products) until it is substantially free of macroscopic air-bubbles or voids or 2) Use a different method to transfer the multi-phase oral care composition into the conical tube such that it is substantially free of macroscopic air-bubbles or voids.
2. Allow the multi-phase oral care composition or hydrophobic phase to equilibrate in the conical tube for at least 12 hours at the desired temperature (for example −7° C., 4° C., 23° C., 25° C., 30° C., 40° C., 50° C., or 60° C.).
3. Confirm the viscometer (Brookfield 1/2RV DVII+Pro Viscometer) is level, turn it on, and autozero it according to the instruction manual.
4. Attach the appropriate spindle (for example Spindle D, E, or F, depending on the viscosity range of interest) and set the appropriate speed (for example 0.5, 1.0, 2.0, 2.5, 4.0, 5.0, 10, 20, 50 and 100 RPM) for the Brookfield Viscosity anticipated to be measured.
5. Place the conical tube under the spindle, lower the spindle until the t-bar is a few mm above the surface of the multi-phase oral care composition, and center the conical tube under the spindle.
6. Turn on the viscometer allow it to spin 3 to 5 rotations to confirm the spindle spins freely without grazing the walls of the conical tube. Turn on the helipath stand. When helipath lowers the t-bar completely under the multi-phase oral care composition or hydrophobic phase, turn on a timer set to 60 seconds. At 60 seconds record the Brookfield Viscosity in cPs.
7. Tap the conical tube on a hard surface or mix the conical tube on a vortex mixer (for example Vortex Genie 2 from Scientific Industries Inc. Bohemia, N.Y., or Mini Vortexer from VWR Scientific Products) until it is substantially free of macroscopic air-bubbles or voids, repeat steps-5-6 for a minimum of 3 measurements, with about 10 minutes between measurements.
8. Tap the conical tube on a hard surface or mix the conical tube on a vortex mixer (for example Vortex Genie 2 from Scientific Industries Inc. Bohemia, N.Y., or Mini Vortexer from VWR Scientific Products) until it is substantially free of macroscopic air-bubbles or voids, and repeat steps 2-7 for a second set od 3 measurements. Calculate the average of all 6 measurements. This is the Brookfield Viscosity of the multi-phase oral composition or hydrophobic phase.

To validate the above method, the Brookfield Viscosity of Example I-B made according to the procedure specified herein must be measured at 2.5 RPM with Spindle D at 23° C. and demonstrated to be from 15,000 to 45,000 cPs.

Method to Measure the Yield Stress of a Multi-Phase Oral Care Composition or Hydrophobic Phase 1. Transfer 40 to 50 ml of the multi-phase oral care composition or hydrophobic phase into a 50 ml polypropylene conical tube (Falcon brand catalog number REF 352098, Corning Science, Tamaulipas, Mexico). If the multi-phase oral care composition or hydrophobic phase exhibits macroscopic separation of one or more components prior to transferring into the conical tube, mix the multi-phase oral care composition or hydrophobic phase in a Speedmixer (for example at 800 RPM for 2 minutes) and transfer into the conical tube before it exhibits macroscopic separation of one or more components. If the multi-phase oral care composition or hydrophobic phase has macroscopic air-bubbles or voids: 1) Tap the conical tube on a hard surface or mix the conical tube on a vortex mixer (for example Vortex Genie 2 from Scientific Industries Inc. Bohemia, N.Y., or Mini Vortexer from VWR Scientific Products) until it is substantially free of macroscopic air-bubbles or voids or 2) Use a different method to transfer the multi-phase oral care composition into the conical tube such that it is substantially free of macroscopic air-bubbles or voids.
2. Allow the multi-phase oral care composition or hydrophobic phase to equiliberate in the conical tube for at least 12 hours at the desired temperature (for example −7° C., 4° C., 23° C., 25° C., 30° C., 40° C., 50° C., or 60° C.).
3. Confirm the rheometer (Brookfield HAYR-1 Rheometer) is level, turn it on, and autozero it according to the instruction manual.
4. Attach the appropriate spindle-vane (for example V72, V73, or V75, depending on the viscosity range of interest) and set to program for the specific spindle-vane being used. The program parameters are specified below:

| Spindle>> | V-72 | V-73 | V-75 |
| --- | --- | --- | --- |
| Yield Stress Range (Pa) | 4-40 | 20-200 | 80-800 |
| Immersion | Primary | Primary | Primary |
| Pre-Sheer rpm | 0 | 0 | 0 |
| Pre-Sheer time | 0 | 0 | 0 |
| Zero Speed (rpm) | 0.1 | 0.1 | 0.1 |
| Wait Time (sec) | 30 | 30 | 30 |
| Run Speed (rpm) | 0.1 | 0.1 | 0.3 |

5. Place the conical tube under the spindle-vane, and lower the spindle-vane slowly into the sample, taking care to minimize any disturbance to the sample this may cause. Continue lowering the spindle-vane until the top surface of the sample is at the primary immersion mark (bulge on the shaft) or secondary immersion mark (notch on the spindle-vane). If the spindle-vane is immersed to the secondary immersion mark, the value generated by this method will need to be multiplied by two.
6. Run the program selected in step-4. Without removing the spindle-vane run the program a total of 3 times. Record the 3 measurements. If the spindle-vane was immersed to the secondary immersion mark, multiply each measurement by 2; and if the spindle-vane was immersed to the primary immersion mark, multiply each measurement by 1. Record the 3 calculated values.
7. Tap the conical tube on a hard surface or mix the conical tube on a vortex mixer (for example Vortex Genie 2 from Scientific Industries Inc. Bohemia, N.Y., or Mini Vortexer from VWR Scientific Products) until it is substantially free of macroscopic air-bubbles or voids, and repeat steps 2-6 for a second set of 3 values. Calculate the average of all 6 values. This is the Yield Stress of the multi-phase oral composition or hydrophobic phase.

To validate the above method, the Yield Stress of Example I-B made according to the procedure specified herein must be measured with spindle-vane V72 immersed to the secondary immersion mark at 23° C. and demonstrated to be from 5 to 20 Pa.

Method to Measure the Slide Flow Distance of a Multi-Phase Oral Care Composition or Hydrophobic Phase 1. Prepare a piece of plexiglass to be 9" long, 3" wide, and ⅛" thick. This is a holder for the microscope slides to be used in following steps.
2. Place a microscope slide (VWR Micro Slides, Super Frost Plus, 25×75×1 mm, manufactured by VWR International, Radnor, Pa.; purchased from VWR, Batavia, Ill., catalog number 48311-703) with the frosted side facing down on the slide holder. Orient the microscope slide such that the longest edge of the microscope slide is parallel to the 3" long edge of the holder and square the microscope slide to the top 9" long edge of the holder. Repeat this for 3 microscope slides side-by-side on the same holder. Note, the holder has room to hold up to 9 slides—making it possible to measure the slide flow distance of up to 3 multi-phase compositions or hydrophobic phases at the same time. Secure the top edge of the microscope slides to the holder using 1" wide tape (see FIG. 13).
3. While the slides and holder are horizontal, apply 0.10 to 0.12 gram of the multi-phase oral care composition or hydrophobic phase to the clear section of each slide in a bead about 20 to 25 mm long across the width of the slide within 5 mm of the bottom edge of the frosted section of the slide (see FIG. 13) using a syringe (3 ml BD Syringe with a Luer Lok tip, REF 309657, purchased from VWR, Batavia, Ill.). Mark the initial lowest point for each bead on the microscope slide.
4. Carefully tilt the holder (with the slides) such that the slides are leaning at a 45 degree angle and hold it motionless in this position for 60 seconds. This may done using a 45 degree stand (see FIG. 14). At 60 seconds, carefully bring the holder (with the slides) back to the horizontal position, and mark the final lowest point for each bead on the microscope slide.
5. Measure the distance from the initial lowest point to the final lowest point of the bead in mm. If the bead has flowed down past the bottom edge of the slide, record the distance from initial lowest point of the bead, and also note this as "greater than" the distance from initial lowest point of the bead.
6. Repeat steps-2-5 for a minimum of 2 sets of 3 slides (minimum total of 6 slides) per multi-phase oral care composition or hydrophobic phase. Calculate the average distance measured on all slides. This is the "slide flow distance" of the multi-phase oral care composition or hydrophobic phase.

To validate the above method, the slide flow distance of 1) Example I-B made according to the procedure specified herein must be measured and demonstrated to be from 0 mm to 15 mm, and, 2) the validation composition specified below made according to the procedure specified herein must be measured and demonstrated to be greater than 40 mm.

| VALIDATION COMPOSITION FOR THE METHOD TO MEASURE THE SLIDE FLOW DISTANCE | (Wt %) |
| --- | --- |
| 35% aqueous solution $H_2O_2$[1] | 1.43 |
| Sterile Filtered Water[2] | 4.24 |
| Aerosol OT[3] | 1.00 |
| Mineral Oil[4] | 93.33 |

[1]ultra Cosmetic Grade from Solvay, Houston, Texas
[2]Calbiochem catalog number 4.86505.1000 from EMD Millipore Corporation, Billerica, Massachusetts
[3]Aerosol OT-100 from Cytec Industries, Princeton, NJ
[4]Kaydol grade from Sonneborn LLC, Petrolia, Pennsylvania Procedure to Make the Validation Composition for the Method to Measure the Slide Flow Distance A 50-gram batch of the validation composition is made according to the following procedure:

a) The Aerosol OT and mineral oil are weighed into a Speedmixer container ("Max 40 Long Cup Translucent", item number 501 223Lt from Flacktek Inc., Landrum, S.C.). The mixture is heated in a convection oven at 60 C and swirled to dissolve the Aerosol OT in the mineral oil.

b) In a separate plastic container, 42.4 grams of sterile filtered water and 14.3 grams of 35% aqueous solution of $H_2O_2$ are weighed and swirled to dissolve the $H_2O_2$ into the water. This diluted solution of $H_2O_2$ is heated in a convection oven at 60 C for about 10 minutes. 2.84 grams of this diluted solution of $H_2O_2$ in water is weighed into the Speedmixer container.

c) The contents of the Speedmixer container are mixed at 800 RPM for 5 seconds, 1200 RPM for 5 seconds, and 1950 RPM for 2 minutes. The walls of the container are then scraped down with a rubber spatula, and the contents are mixed a second time at 800 RPM for 5 seconds, 1200 RPM for 5 seconds, and 1950 RPM for 2 minutes. The walls of the container are then scraped down with a rubber spatula, and the contents are mixed a third time at 800 RPM for 5 seconds, 1200 RPM for 5 seconds, and 1950 RPM for 2 minutes.

Method to Measure the Percent Macroscopic Separation of One or More Components of a Multi-Phase Oral Care Composition 1. Transfer 50 ml of the multi-phase oral composition into a 50 ml polypropylene conical tube (Falcon brand catalog number REF 352098, Corning Science, Tamaulipas, Mexico). If the multi-phase oral composition exhibits macroscopic separation of one or more components prior to transferring into the conical tube, mix the multi-phase oral composition in a Speedmixer (in a "Max 300 Long Cup Translucent", item number 501 218t from Flacktek Inc., Landrum, S.C.) (for example at 800 RPM for 2 minutes) and transfer into the conical tube before it exhibits macroscopic separation of one or more components. If the multi-phase oral composition has macroscopic air-bubbles or voids: 1) Tap the conical tube on a hard surface until it is free of macroscopic air-bubbles or voids, or 2) Use a different method to transfer the multi-phase oral composition into the conical tube such that it is substantially free of macroscopic air-bubbles or voids. Screw the cap onto the conical tube. Repeat for a total of three conical tubes.

2. Position all three conical tubes in a vertical orientation (for example in a test tube rack) with the conical end on the bottom and the cap on top.

3. Allow all three conical tubes to stay undisturbed in the vertical position in a room or chamber in which the air is maintained at the temperature (for example −7° C., 4° C., 23° C., 25° C., 30° C., 40° C., 50° C., or 60° C.) for the period of time after which the macroscopic separation is to be measured.

4. At the end of period of time after which the macroscopic separation is to be measured (for example 1 day, 2 days, 1 week, 2 weeks, 1 month, 2 months, 3 months, 6 months, 12 months, 18 months, or 24 months) in the vertical position, measure the volume of material that has macroscopically separated on the bottom of the conical tube (aided by the graduations on the conical tube). If the volume of material that has macroscopically separated on the bottom of the conical tube is greater than 25 ml, measure the volume of material that has macroscopically separated to the top of the conical tube.

Calculate the average volume of material that has macroscopically separated in all three tubes.

Assess the tube to tube variability of the volume of material that has macroscopically separated as follows: The volume of material that has separated in each and every tube must be within the range of +/−2.5 ml of the average. If the volume of material that has separated in any one or more of the tubes is outside the range of +/−2.5 ml of the average: This is an indication of sample to sample variability potentially due to macroscopic separation of one or more components prior to transferring into the conical tubes, and the method needs to be repeated starting at step-1 to minimize sample to sample variability.

5. Calculate the percent macroscopic separation as: 100× (average volume of material that has macroscopically separated measured and calculated in step-4 DIVIDED by 50 ml).

To validate the above method, the percent macroscopic separation of one or more components of the validation composition specified below must be measured and demonstrated to be from 6% to 10%.

| VALIDATION COMPOSITION FOR METHOD TO MEASURE PERCENT MACROSCOPIC SEPARATION | (Wt %) |
| --- | --- |
| 35% aqueous solution $H_2O_2$[1] | 1.43 |
| Sterile Filtered Water[2] | 4.24 |
| Aerosol OT[3] | 1.00 |
| Mineral Oil[4] | 93.33 |

[1]ultra Cosmetic Grade from Solvay, Houston, Texas
[2]Calbiochem catalog number 4.86505.1000 from EMD Millipore Corporation, Billerica, Massachusetts
[3]Aerosol OT-100 from Cytec Industries, Princeton, NJ
[4]Kaydol grade from Sonneborn LLC, Petrolia, Pennsylvania Procedure to Make the Validation Composition for Method to Measure Percent Macroscopic Separation Three 50-gram batches of the validation composition are made according to the following procedure:

d) The Aerosol OT and mineral oil are weighed into a Speedmixer container ("Max 40 Long Cup Translucent", item number 501 223Lt from Flacktek Inc., Landrum, S.C.). The mixture is heated in a convection oven at 60 C and swirled to dissolve the Aerosol OT in the mineral oil.

e) In a separate plastic container, 42.4 grams of sterile filtered water and 14.3 grams of 35% aqueous solution of $H_2O_2$ are weighed and swirled to dissolve the $H_2O_2$ into the water. This diluted solution of $H_2O_2$ is heated in a convection oven at 60 C for about 10 minutes. 2.84 grams of this diluted solution of $H_2O_2$ in water is weighed into the Speedmixer container.

f) The contents of the Speedmixer container are mixed at 800 RPM for 5 seconds, 1200 RPM for 5 seconds, and 1950 RPM for 2 minutes. The walls of the container are then scraped down with a rubber spatula, and the contents are mixed a second time at 800 RPM for 5 seconds, 1200 RPM for 5 seconds, and 1950 RPM for 2 minutes. The walls of the container are then scraped down with a rubber spatula, and the contents are mixed a third time at 800 RPM for 5 seconds, 1200 RPM for 5 seconds, and 1950 RPM for 2 minutes.

Method to Measure the Mean Residual Peroxide Concentration of a Composition Smeared on Teeth 1. Cut a circular disc (7.5 to 7.8 mm diameter×1.2 to 1.3 mm thickness) out of the front surface of a human incisor tooth. Leave the front surface intact but flatten the back surface that has been cut out of tooth using sandpaper. Soak the tooth-disc in 15 to 20 ml of water that meets USP specification in a glass vial for at least 24 hours. Take the tooth-disc out of the water and place it on a fresh paper towel with the front surface facing upward.
2. Weigh 290 to 310 grams of water that meets USP specifications into a cylindrical plastic container with a screw-top lid 82 to 107 mm in diameter×106 to 108 mm height ("Max 200 Long Cup Translucent", item number 501 220t from Flacktek, Landrum, S.C.). Pre-heat the water in the container with the lid screwed on tight in a convection oven with air temperature at 33 C to 35 C for at least 12 hours.
3. Weigh 0.04 to 0.06 gram of the composition onto the tip of a disposable lip gloss applicator ("Flocked Doe Foot Lip Gloss Applicator" made of Nylon and Polystyrene, purchased from Qosmedix Inc., Ronkonkoma, N.Y., catalog number 74111).
4. Smear the composition onto the front surface of the wet tooth-disc by first rolling the tip of the lip gloss applicator loaded with the composition on the front surface of the tooth-disc to transfer the composition onto the tooth-disc and then fanning out toward the circular edge.
5. Pick up the tooth-disc with a tweezer. Make sure the tweezer touches only the circular edge of the tooth-disc and not the surface of the tooth-disc smeared with the composition. Tilt the plastic container and gently place the tooth-disc in the water on the cylindrical wall of the container where the cylindrical wall and flat bottom meet. Make sure the treated surface of the tooth-disc is facing upward away from the cylindrical wall of the container.
6. Place the cylindrical container on a roller mixer (model number TSRT9 by Techne purchased from VWR, Batavia, Ill., catalog number 89132-186; or item number 04750-30 from Cole-Parmer Inc., Vernon Hills, Ill.). Turn on the roller mixer—this gently rotates the container at 12 to 14 RPM. The tooth-disc should continue to remain immersed in the water and the treated surface should continue to face away from the rotating cylindrical wall. This rotating motion causes the water to flow gently over the tooth-disc similar to the gentle movement of saliva and other liquids over teeth in the mouth.
7. After 58 to 62 minutes shut off the roller mixer, take a fresh peroxide test strip (supplied by EMD Millipore Corporation, Billerica, Mass., supplier number 1.16974.0001; purchased from VWR, Batavia, Ill., catalog number EM1.16974.0001) out of the container, and start a timer.
8. Take a digital image of the peroxide test strip. The equipment and system configuration used to take the digital image of the test strip are specified herein.
9. Remove the tooth-disc from the water using a tweezer. As before, make sure the tweezer touches only the circular edge of the tooth-disc and not the surface of the tooth-disc smeared with the composition. Place the tooth-disc on a gloved finger-tip. Make sure the surface of the tooth-disc smeared with the composition is facing upward away from the gloved finger-tip.
10. Place the peroxide test strip against the tooth-disc such that one of the reaction-zones contacts the surface of the tooth-disc with the residual composition. Pinch the peroxide test strip against the tooth-disc between thumb and forefinger and apply firm finger pressure between thumb and forefinger for 2 to 3 seconds.
11. Move the peroxide test strip to a clean area of a paper towel. Place a filter paper (Whatman Grade 1 Qualitative Filter Paper Standard Grade, circle, 90 mm, supplier number 1001-090; purchased from VWR, Batavia, Ill., catalog number 28450-081) on top of the test strip. Apply finger pressure on top of the filter paper. Pull the peroxide test strip out from under the filter paper (while maintaining finger pressure on the filter paper) in a single stroke such that excess gel is wiped off onto the filter paper and paper towel. Make sure the reaction-zones do not get dislodged from the peroxide test strip.
12. Take a digital image of the peroxide test strip. The equipment and system configuration used to take the digital image of the test strip are specified herein.
13. Steps 7 to 12 must be completed within 3 minutes on the timer.
14. Repeat steps 1 to 13 for a minimum of twelve teeth.
15. Use Adobe Photoshop CS4 with the procedure specified herein to measure the mean and standard deviation of the Red intensities of the strip of Munsell N8 Matte Color sheet attached to the holder that serves as a built-in Munsell N8 reference within each image. The mean R value intensity of the built-in Munsell N8 reference within each image should be from 204 to 212 and the standard deviation should be no more than 3.
16. Use Adobe Photoshop CS4 with the procedure specified herein to measure the mean of the Red intensities of the reaction-zone on all peroxide test strips at BASELINE (before pressing against the tooth-disc).
17. Use Adobe Photoshop CS4 with the procedure specified herein to measure the mean of the Red intensities of same the reaction-zone on all peroxide test strips AFTER pressing against the tooth-disc.
18. The mean residual peroxide concentration of a composition smeared on teeth is calculated as follows: First, calculate the mean baseline R value intensity of each reaction-zone from step-16 MINUS the mean R value intensity of the same reaction-zone after pressing with the residual composition on the tooth-disc from step-17. Repeat this calculation for all reaction-zones pressed against the tooth-disc, and average the results. This is the mean residual peroxide concentration of a composition smeared on teeth.

Method to Determine if a Composition is Easy to Manually Dispense from a Tube
1. Select a foil laminate tube with the following dimensions:
    a. Total length from tip of nozzle to bottom of barrel: About 112 mm
    b. Internal diameter of barrel: About 28 mm
    c. Length of nozzle: About 21 mm
    d. Internal diameter of nozzle: About 9.7 mm for half the length of the nozzle attached to the barrel, and about 4.2 mm for the other half the of the nozzle leading to the exit orifice of the nozzle.
2. Fill from about 35 to about 40 grams of the composition through the bottom of the barrel into the tube from step-1. Seal the bottom of the barrel using an ultrasonic sealer.
3. Allow the tube to stay undisturbed in a room or chamber in which the air is maintained at the temperature (for example −7° C., 4° C., 23° C., 25° C., 30° C., 40° C., 50° C., or 60° C.) for the period of time after which the ease of dispensing is to be measured.
4. Allow the tube to equilibrate at about 23° C. for at least a day.
5. Pick up the tube between the thumb and fingers of one hand. While holding the tube in the air, squeeze the tube firmly between the thumb and fingers for about 10 seconds. Measure the length of the bead of the composition dispensed out of the nozzle of the tube.
6. The composition is considered easy to dispense manually from a tube after the specified period of time at the specified temperature if at least 1 inch of product is dispensed in step-5.

Examples

The following non-limiting examples further describe preferred embodiments within the scope of the present invention. Many variations of these examples are possible without departing from the scope of the invention. All examples were performed at room temperature (RT) and atmospheric pressure unless stated otherwise.

TABLE 1

| Weight %* | A | B | C | D | E | F |
|---|---|---|---|---|---|---|
| EXAMPLE I | | | | | | |
| 35% aqueous solution of $H_2O_2$[1] | 15 | 8.5714 | 5 | 2.5 | 1.5 | 8.5714 |
| PEG-20 Sorbitan monolaurate (Tween 20)[2] | 1 | 1 | 1 | 1 | 1 | 3.43 |
| Mineral oil[3] | 84 | 90.4286 | 94 | 96.5 | 97.5 | 87.9986 |
| % $H_2O_2$ | 5.25 | 3 | 1.75 | 0.875 | 0.525 | 3 |
| % Aqueous phase | 16 | 9.5714 | 6 | 3.5 | 2.5 | 12.0014 |
| % Hydrophobic phase | 84 | 90.4286 | 94 | 96.5 | 97.5 | 87.9986 |
| % Aqueous phase by volume | 12.8341 | 7.57190 | 4.7147 | 2.7433 | 1.9610 | 9.5893 |
| % Hydrophobic phase by volume | 87.1659 | 92.4290 | 95.2853 | 97.2567 | 98.0390 | 90.4107 |

[1]Ultra cosmetic grade 35% from Solvay, Houston, TX
[2]Tween20-LQ-(AP) from Croda Inc. Edison, NJ
[3]Kaydol grade from Sonneborn LLC., Parsippany, NJ
*% wt of total multi-phase composition unless otherwise indicated

TABLE 2

| | EXAMPLE II-V | | | |
|---|---|---|---|---|
| Component | Example II (wt %) | Example III (wt %) | Example IV (wt %) | Example V (wt %) |
| 35% aqueous solution of $H_2O_2$ | 2.8571[1] | 8.5714[2] | 8.5714[2] | 8.5714[2] |
| PEG-20 Sorbitan monolaurate (Tween 20)[3] | 1 | 1 | 1 | 1 |
| Mineral oil | 96.1429[4] | 90.4286[5] | 45.2143 | — |
| Petrolatum[6] | — | — | 45.2143 | — |
| Mineral Oil (and) Ethylene/Propylene/Styrene Copolymer (and) Butylene/Ethylene/Styrene Copolymer[7] | — | — | — | 90.4286 |
| % $H_2O_2$ | 0.5 | 3 | 3 | 3 |
| % Aqueous phase | 3.8571 | 9.5714 | 9.5714 | 9.5714 |
| % Hydrophobic phase | 96.1429 | 90.4286 | 90.4286 | 90.4286 |

[1]Ultra cosmetic grade 35% from Solvay, Houston, TX diluted with water (1:1 17.5% $H_2O_2$)
[2]Ultra cosmetic grade 35% from Solvay, Houston, TX
[3]Tween20-LQ-(AP) from Croda Inc. Edison, NJ
[4]Kaydol grade from Sonneborn LLC., Parsippany, NJ
[5]Hydrobrite HV grade from Sonneborn LLC., Parsippany, NJ
[6]G-2218 Grade from Sonneborn, LLC., Parsippany, NJ
[7]Versagel grade M 750 from Penreco Inc., Karns City, PA Batches of Examples I, II, and III were made according to the following procedure:
1. The Tween 20 and aqueous solution of $H_2O_2$ were weighed into a Speedmixer container (Max 300 Long Cup Translucent item number 501 218t or Max 300× Long Cup Translucent item number 501 217t, for the 150-gram and 250-gram batches, and Max 200 Long Cup Translucent item number 501 220t for the 50-gram batches, all containers from Flacktek Inc., Landrum, S.C.) and mixed by manually swirling the container until dissolved.
2. The mineral oil was added in portions (see table below, generally starting with small portions and increasing to larger portions) and mixed for about 1 to 2 minutes between portions with a rubber spatula. An oil-in-water emulsion formed during this step, and the composition developed a lotion-like semisolid consistency.

3. Once all the mineral oil was added, the contents of the Speedmixer container were mixed 3 times at 800 RPM for 2 minutes each time in a Speedmixer.

A batch of Example IV was made according to the following procedure:

1. The Tween 20 and aqueous solution of $H_2O_2$ were weighed into a Speedmixer container (Max 300 Long Cup Translucent, item number 501 218t from Flacktek Inc., Landrum, S.C.) and mixed by manually swirling the container until dissolved.

2. 30 grams of mineral oil was added in 2 portions of about 15 grams each and mixed for about 1 to 2 minutes between portions with a rubber spatula. Separately, 44.61 grams of mineral oil and 80 grams of petrolatum were blended together after heating to about 80 C in a convection oven. 105.44 grams of this blend was then added in a portions (increasing from about 13 grams to about 33 grams per portion) and mixed for about 1 to 2 minutes between portions with a rubber spatula. The speedmixer container was immersed in water at 60 C during mixing, and the blend was re-heated to 75 C to 80 C after the first two portions.

3. The contents of the Speedmixer container were mixed 2 times at 800 RPM for 2 minutes each time in a Speedmixer.

A batch of Example V was made according to the following procedure:

1. The Tween 20 and aqueous solution of $H_2O_2$ were weighed into a Speedmixer container (Max 300 Long Cup Translucent, item number 501 218t from Flacktek Inc., Landrum, S.C.) and mixed by manually swirling the container until dissolved.

2. The Versagel was added in a portions (see table below, generally starting with small portions and increasing to larger portions) and mixed for at least 2 minutes between portions with a rubber spatula.

Once all the Versagel was added, the contents of the Speedmixer container were mixed 3 times at 800 RPM for 2 minutes each time in a Speedmixer.

| EXAMPLE NUMBER | Batch size (g) | Approximate portion size (g) |
| --- | --- | --- |
| I-A | 150 | 10 to 25 |
| I-B | | |
| Batch-1 | 150 | 25 |
| Batch-2 | 150 | 15 to 25 |
| Batch-3 | 250 | 23 to 51 |
| Batch-4 | 150 | 20 to 25 |
| Batch-5 | 150 | 20 to 25 |
| Batch-6 | 150 | 20 to 25 |
| Batch-7 | 250 | 5 to 20 |
| Batch-8 | 250 | 5 to 20 |
| I-C | 150 | 5 to 10 |
| I-D | 150 | 2 to 10 |
| I-E | 150 | 2 to 10 |
| I-F | 50 | 10 |
| II | 150 | 4 to 15 |
| III | 150 | 25 |
| IV | 150 | 12 to 33 |
| V | 150 | 5 to 10 |

TABLE 3

COMPARATIVE EXAMPLES
COMPARATIVE EXAMPLE I-IV

| | I (wt %) | II (wt %) | III (wt %) | IV (wt %) |
| --- | --- | --- | --- | --- |
| 35% aqueous solution of $H_2O_2$[1] | 25 | 8.5714 | 8.5714 | 8.5714 |
| PEG-20 Sorbitan monolaurate (Tween 20)[2] | 1 | — | — | 3.43 |
| PEG-20 Sorbitan monostearate (Tween 60)[3] | — | 3.43 | — | — |
| PEG-20 Sorbitan monopalmitate (Tween 40)[4] | — | — | 3.43 | — |
| Mineral oil[5] | 74 | 87.9986 | 87.9986 | 87.9986 |
| % $H_2O_2$ | 8.75 | 3 | 3 | 3 |
| % Aqueous phase | 26 | 12.0014 | 12.0014 | 12.0014 |
| % Hydrophobic phase | 74 | 91.3286 | 87.9986 | 87.9986 |
| % Aqueous phase by volume | 21.3475 | — | — | — |
| % Hydrophobic phase by volume | 78.6525 | — | — | — |

[1]35% Aqueous Solution Ultra cosmetic grade from Solvay, Houston, TX
[2]Tween20-LQ-(AP) from Croda Inc. Edison, NJ
[3]Tween60-LQ-(AP) from Croda Inc. Edison, NJ
[4]Tween40-LQ-(AP) from Croda Inc. Edison, NJ
[5]Kaydol grade from Sonneborn LLC., Parsippany, NJ

TABLE 4

COMPARATIVE EXAMPLES V-VIII

| | V (wt %) | VI (wt %) | VII (wt %) | VIII (wt%) |
| --- | --- | --- | --- | --- |
| 35% aqueous solution of $H_2O_2$[1] | 8.5714 | 8.6055 | 8.571 | 8.5714 |
| PEG-20 Sorbitan monolaurate (Tween 20)[6] | — | — | — | 1 |
| Sorbitan monolaurate (Span 20)[2] | 1 | — | — | — |
| Sorbitan monopalmitate (Span 40)[3] | — | 0.02876 | — | — |
| Mineral oil[4] | 90.4286 | — | — | 90.4286 |
| Petrolatum[5] | — | 91.3658 | 91.429 | — |
| % $H_2O_2$ | 3 | 3.0119 | 3 | 3 |
| % Aqueous phase | 8.5714 | 8.6055 | 8.571 | 9.5714 |
| % Hydrophobic phase | 91.4286 | 91.3945 | 91.429 | 90.4286 |

[1]Ultra cosmetic grade 35% from Solvay, Houston, TX
[2]Span20-LQ-(AP) from Croda Inc. Edison, NJ
[3]Span 40 from Croda Inc., Edison, NJ, USA.
[4]Hydrobrite HV grade from Sonneborn LLC., Parsippany, NJ
[5]G-2218 Grade from Sonneborn, LLC., Parsippany, NJ
[6]Tween20-LQ-(AP) from Croda Inc. Edison, NJ Batches of Comparative Examples I, II, and III, were made according to the following procedure:

1. The Tween 20, Tween 40, or Tween 60, was weighed into a Speedmixer container (Max 300 Long Cup Translucent, item number 501 218t from Flacktek Inc., Landrum, S.C.) followed by the aqueous solution of $H_2O_2$. The batch of Comparative Examples I and II were mixed by manually swirling the container until dissolved. The batch of Comparative Example III was vigorously mixed with a rubber spatula until it was dissolved.

2. The mineral oil was added in portions (see table below) and mixed for about 1 to 2 minutes between portions with a rubber spatula.

3. Once all the mineral oil was added, the contents of the Speedmixer container were mixed 3 times at 800 RPM for 2 minutes each time in a Speedmixer.

| COMPARATIVE EXAMPLE NUMBER | Batch size (g) | Approximate portion size (g) |
|---|---|---|
| I | 150 | 10 |
| II | 150 | 25 |
| III | 150 | 25 |
| IV | 50 | All mineral oil added in 1 single portion |
| V | 150 | n/a |
| VI | 250 | n/a |
| VII | 250 | n/a |
| VIII | 150 | 2 |

A batch of Comparative Example IV was made according to the following procedure:
1. The Tween 20 was weighed into a Speedmixer container (Max 200 Long Cup Translucent item number 501 220t from Flacktek Inc., Landrum, S.C.) followed by the aqueous solution of H2O2, and mixed by manually swirling the container until dissolved.
2. All the mineral oil was weighed into the Speedmixer container in 1 single portion.
3. Once the mineral oil was added, the contents of the Speedmixer container were mixed 1 time at 800 RPM for 2 minutes followed by 1 time at 2600 RPM for 2 minutes in a Speedmixer.

A batch of Comparative Example V was made according to the following procedure:
1. The Span 20 was weighed into a Speedmixer container (Max 300 Long Cup Translucent, item number 501 218t from Flacktek Inc., Landrum, S.C.) followed by the mineral oil, and mixed at 800 RPM for two minutes in a Speedmixer until dissolved.
2. The aqueous solution of $H_2O_2$ was weighed into the Speedmixer container.
3. The contents of the Speedmixer container were mixed 3 times at 800 RPM for 2 minutes each time in a Speedmixer.

A batch of Comparative Example VI was made according to the following procedure:
1. The Span 40 and petrolatum were weighed into a Speedmixer container (Max 300 Long Cup Translucent, item number 501 218t from Flacktek Inc., Landrum, S.C.). This container was then placed in an convection oven set at 60 C until the temperature of the contents was >58 C. The contents of the container were then mixed at 2350 RPM for 30 seconds in a speedmixer to dissolve the Span 40 into the petrolatum.
2. The container was then placed in an convection oven set at 34 C until the temperature of the contents was <38 C. The aqueous solution of H2O2 was weighed into the Speedmixer container.
3. The contents of the Speedmixer container were mixed 3 times at 800 RPM for 2 minutes each time in a Speedmixer.

A batch of Comparative Example VII was made as follows:
1. The petrolatum and 35% aqueous solution of H2O2 were added into a Max 300 Long Speedmixer container (Flacktek Inc., Landrum, S.C.) and mixed in a SpeedMixer (Flacktek Inc., Landrum, S.C.) at 1600 RPM for 30 seconds.
2. The mixture was transferred to an empty 12.8 oz Caulk Cartridge (McMaster Carr, Robbinsville, N.J.) and stored in a refrigerator until the measured product temperature was 8° C.
3. The Caulk Cartridge was inserted into a Pneumatic Caulk Gun (McMaster Can, Robbinsville, N.J.), and connected to the inlet of a Microfluidizer model M-110Y (Microfluidics, Westwood, Mass. 02090). The outlet piping of the Microfluidizer was arranged such that the product passed through only a F20Y Interaction Chamber and several cm of piping before and after. The inlet pressure to the Microfludizer was adjusted to 40 psig, and the inlet pressure to the Caulk Cartridge was adjusted to 94 psig. The final product was collected in a plastic container.

A batch of Comparative Example VIII was made according to the following procedure:
1. The mineral oil was weighed into a Speedmixer container (Max 300 Long Cup Translucent, item number 501 218t from Flacktek Inc., Landrum, S.C.).
2. The Tween 20 was weighed into a separate Speedmixer container ("Max 40 Long Cup Translucent", item number 501 223Lt from Flacktek Inc., Landrum, S.C.) followed by the aqueous solution of H2O2, and mixed by manually swirling the container until dissolved. This mixture was then added in multiple portions (see table above) to the mineral oil from step-1 and mixed for about 1 to 2 minutes between portions with a rubber spatula. The composition remained liquid and did not develop a lotion-like semisolid consistency during this step.
3. Once all the mixture of Tween 20 and aqueous solution of $H_2O_2$ was added, the contents of the Speedmixer container were mixed 3 times at 800 RPM for 2 minutes each time in a Speedmixer.

TABLE 5

| Mean Peroxide Concentration | | |
|---|---|---|
| | Comparative Example VI (Water-in-oil) (3% H2O2) | Example I-B (Jammed oil-in-water) (3% H2O2) |
| Mean peroxide concentration smeared onto test strips | 26.97 | 69.51 |

TABLE 6

| Whitening Efficacy | | |
|---|---|---|
| | Comparative Example VII (Water-in-oil) (90 minutes per treatment) | Example I-B (Jammed oil-in-water) (60 minutes per treatment) |
| Mean decrease in yellowness (−Δb*) after 1 treatment (measured the next day) | 2.185 | 2.908 |
| Mean decrease in yellowness (−Δb*) after 2 treatments (measured the next day) | 3.333 | 4.214 |
| Mean decrease in yellowness (−Δb*) after 3 treatments (measured the next day) | — | 5.070 |

TABLE 7

Stability of Active Agents

| Example I-B | Target for % $H_2O_2$ remaining is 3% | | |
|---|---|---|---|
| Oil-in-water emulsion | Sample-1 | Sample-2 | Sample-3 |
| % $H_2O_2$ remaining in sample after 90 days at 40° C. | 2.926 | 2.938 | 2.915 |

TABLE 8

Slide Flow Distance

| Measured according to the methods specified herein | Slide flow distance (mm) |
|---|---|
| Example I-B | 5 mm |
| Validation composition for the method to measure the slide flow distance specified herein | >45 mm |

TABLE 9

Yield Stress

| Measured according to the method specified herein | Yield Stress (Pa) |
|---|---|
| Example I-B | 12 |

TABLE 10

Water Dispersibility and Whitening Efficacy

| | Comparative Example VII (Water-in-oil) (90 minutes per treatment) | Example I-B (Oil-in-water) (60 minutes per treatment) |
|---|---|---|
| Water-dispersibility (%) measured according to the method specified herein at 23° C. | 2 | 70 |
| Mean decrease in yellowness (−Δb*) after 1 treatment (measured the next day) | 2.185 | 2.908 |
| Mean decrease in yellowness (−Δb*) after 2 treatments (measured the next day) | 3.333 | 4.214 |
| Mean decrease in yellowness (−Δb*) after 3 treatments (measured the next day) | — | 5.070 |

TABLE 11

Brookfield Viscosity of Example I-B

| | Brookfield Viscosity (cPs) |
|---|---|
| Example I-B | 29,000[1] |
| Hydrophobic Phase (Mineral Oil) | 170[2] |
| Aqueous Phase (Plus $H_2O_2$ and Tween 20) | 22[2] |

[1] Using spindle D, 2.5 RPM
[2] Below detection limit for spindle D at 2.5 RPM, measured using spindle D at 100 RPM

TABLE 12

Yield Stress of Example I-B

| | Yield Stress (Pa) |
|---|---|
| Example I-B | 12 |
| Hydrophobic Phase (Mineral Oil) | <Detection Limit of 4 |
| Aqueous Phase (Plus $H_2O_2$ and Tween 20) | <Detection Limit of 4 |

TABLE 13

D[4,3] equivalent-diameter of regions of hydrophobic phase of Examples I-A, I-B, I-C, and I-D.

| | I-A | I-B | I-C | I-D |
|---|---|---|---|---|
| D[4,3] equivalent-diameter of regions of hydrophobic phase measured according to the method specified herein at 23° C. (microns) | 50 | 23 | 12 | 4 |
| % Aqueous phase | 16 | 9.5714 | 6 | 3.5 |
| % Hydrophobic phase | 84 | 90.4286 | 94 | 96.5 |

TABLE 14

D[4,3] equivalent-diameter of regions of hydrophobic phase of Examples I-B and I-F.

| | I-B | I-F |
|---|---|---|
| D[4,3] equivalent-diameter of regions of hydrophobic phase measured according to the method specified herein at 23° C. (microns) | 23 | 9 |
| % Emulsifier | 1 | 3.4 |

Figure 2:
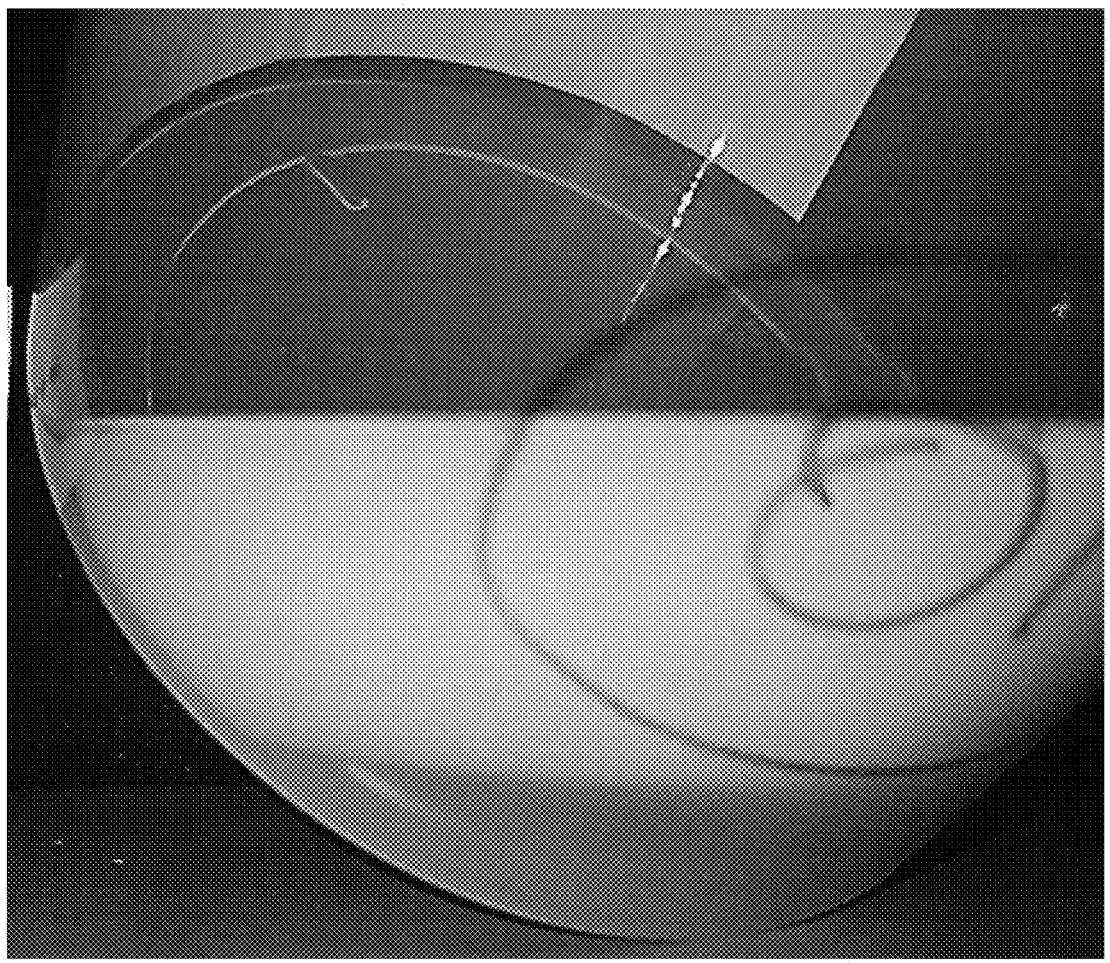
FIG. 2 shows the macroscopic separation of Comparative Example 1 (74% hydrophobic phase).
Figure 3A:
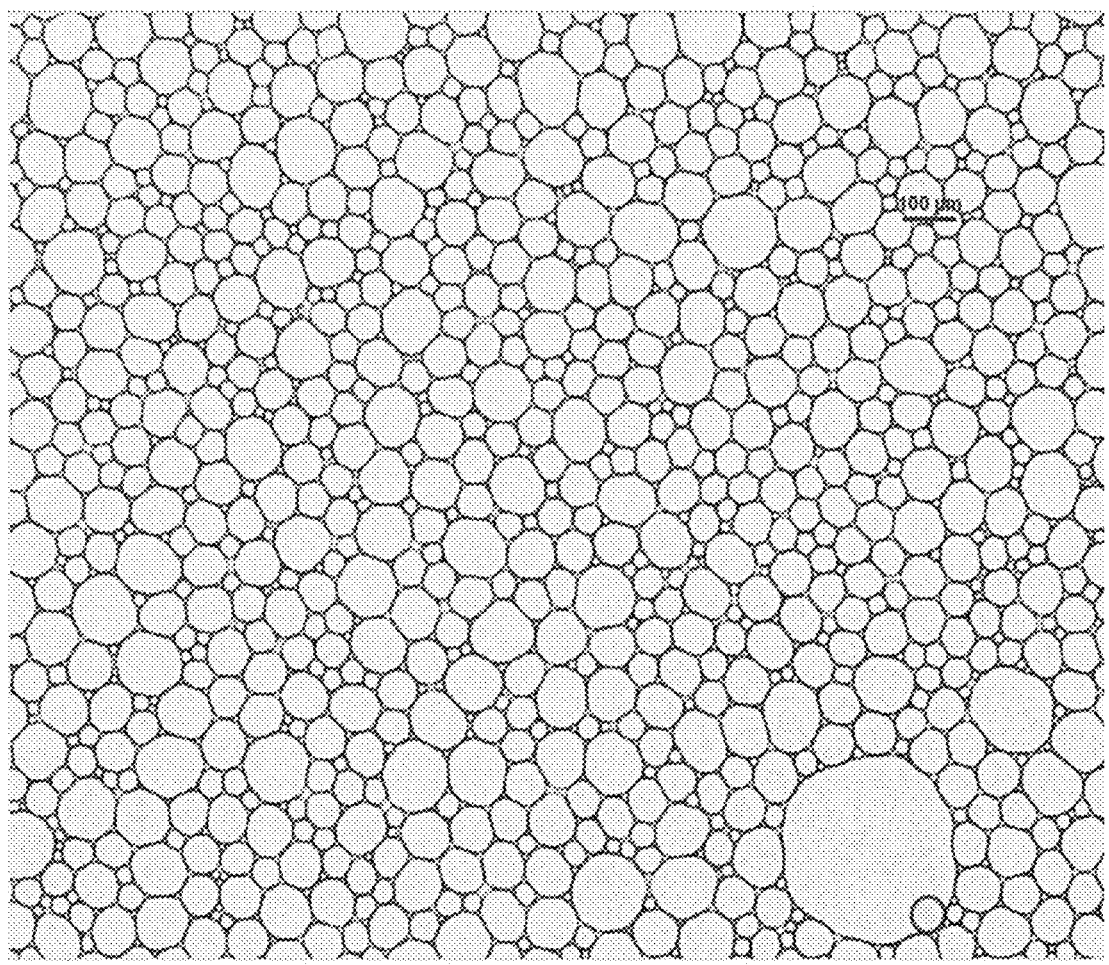
FIG. 3A shows the microscope image of the stable jammed oil-in-water emulsion of Example I-A (84%).
Figure 3B:
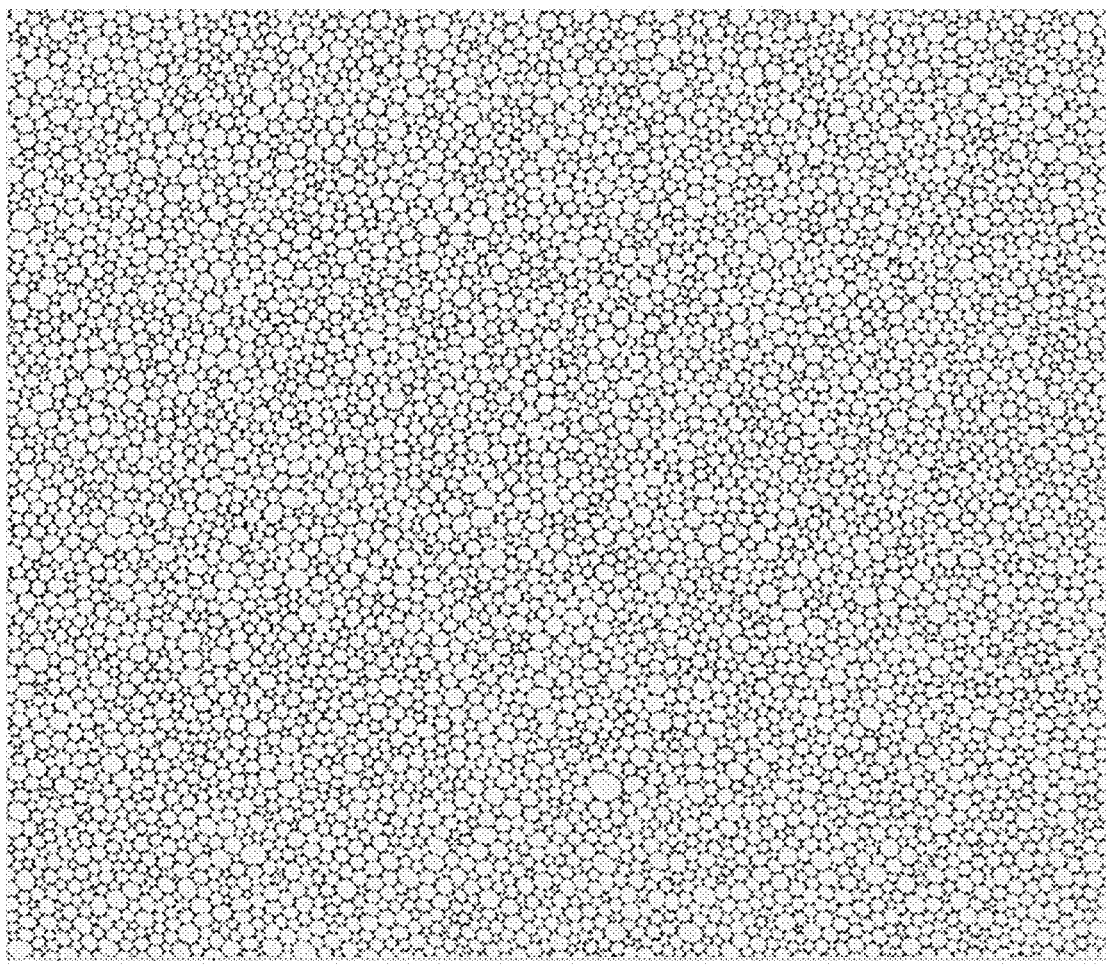
FIG. 3B shows the microscopic image of the stable jammed oil-in-water emulsion of Example I-B (90.4%).
Figure 3C:
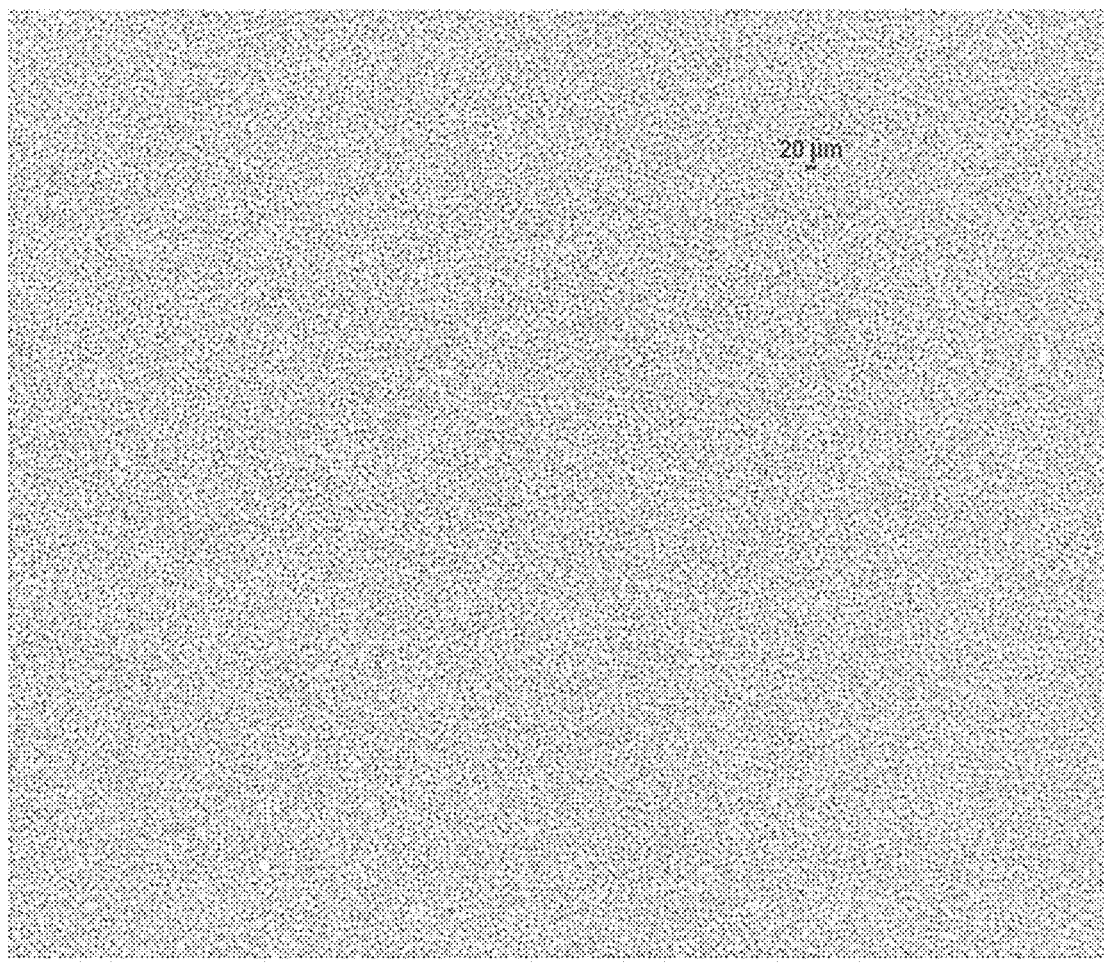
FIG. 3C shows the microscopic image of the stable jammed oil-in-water emulsion of Example I-C (94%).
Figure 3D:
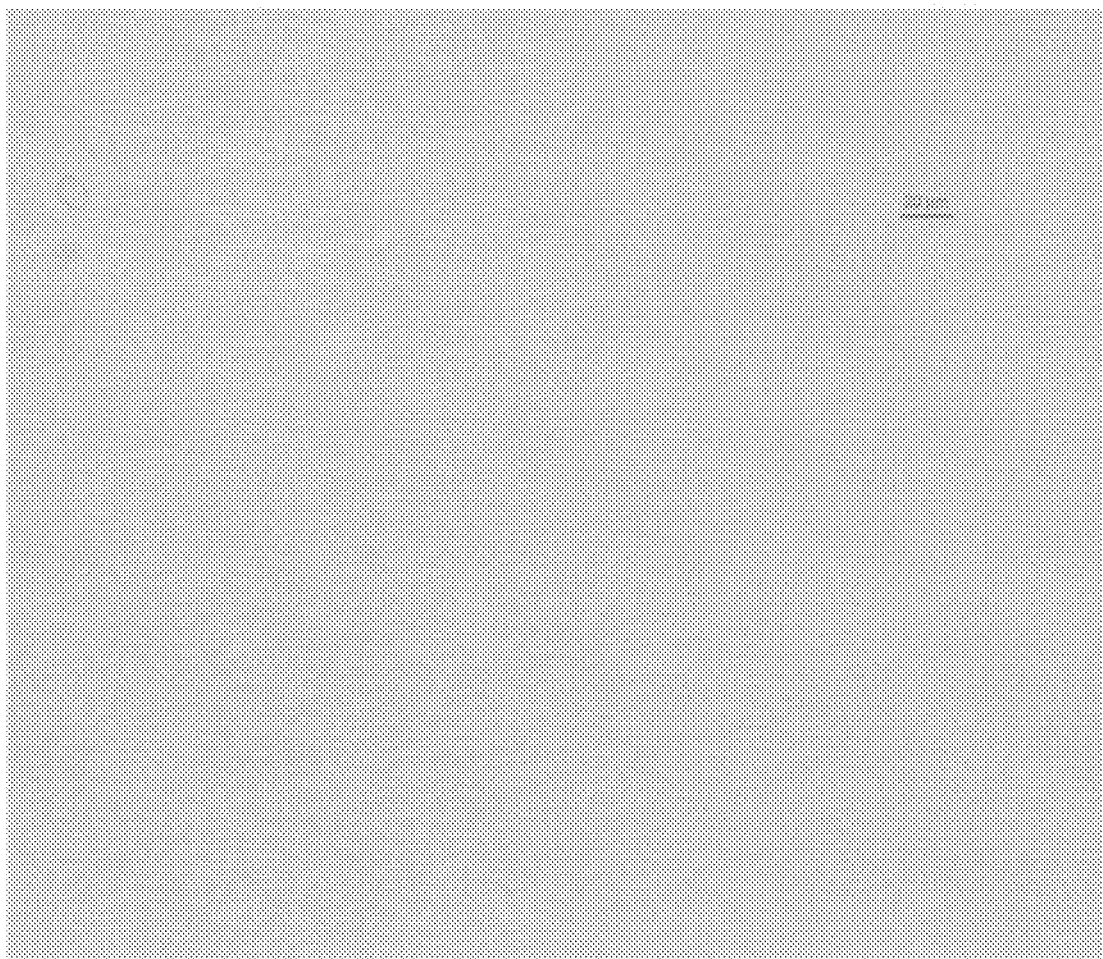
FIG. 3D shows the microscopic image of the stable jammed oil-in-water emulsion of Example I-D (96.5%).
Figure 3E:
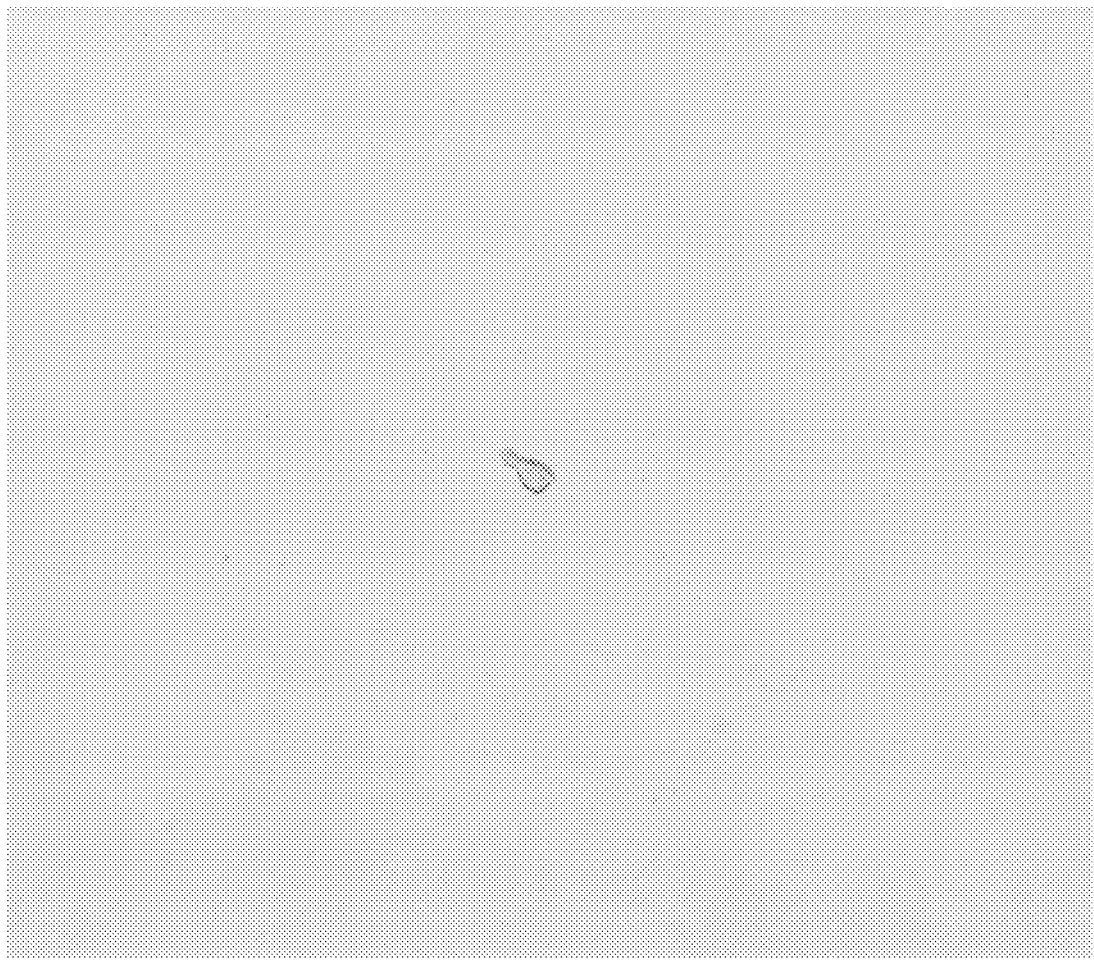
FIG. 3E shows the microscopic image of the stable jammed oil-in-water emulsion of Example I-E (97.5%).

FIG. 1A-1E show the stable jammed oil-in-water emulsions of Example IA-IE. These compositions are shown in TABLE 1. In contrast, FIG. 2, shows a high internal phase oil-in-water emulsion that demonstrated macroscopic separation. Importantly and unexpectedly, Examples 1A-1E (≥84% hydrophobic phase) all had a higher proportion of hydrophobic phase than Comparative Example I (74% hydrophobic phase).

FIG. 3A-3E are microscopic images of the stable jammed oil-in-water emulsions. Examples IA-IE. In these images, the hydrophobic phase appears as large regions with a thin region of continuous aqueous phase with hydrogen peroxide. In certain embodiments, as the concentration of the hydrophobic phase passes the jamming concentration, the ability for hydrophobic regions to move becomes less as hydrophobic regions influence the shape of adjacent or neighboring regions. This is seen in FIG. 3A-3E with the regions pressing against one another resulting in polyhedral shapes instead of spherical droplets. As seen in the images, Example I-A had minimal macroscopic separation and Examples I-B to I-E had no macroscopic separation after 2 days at 60° C.

Figure 4A:
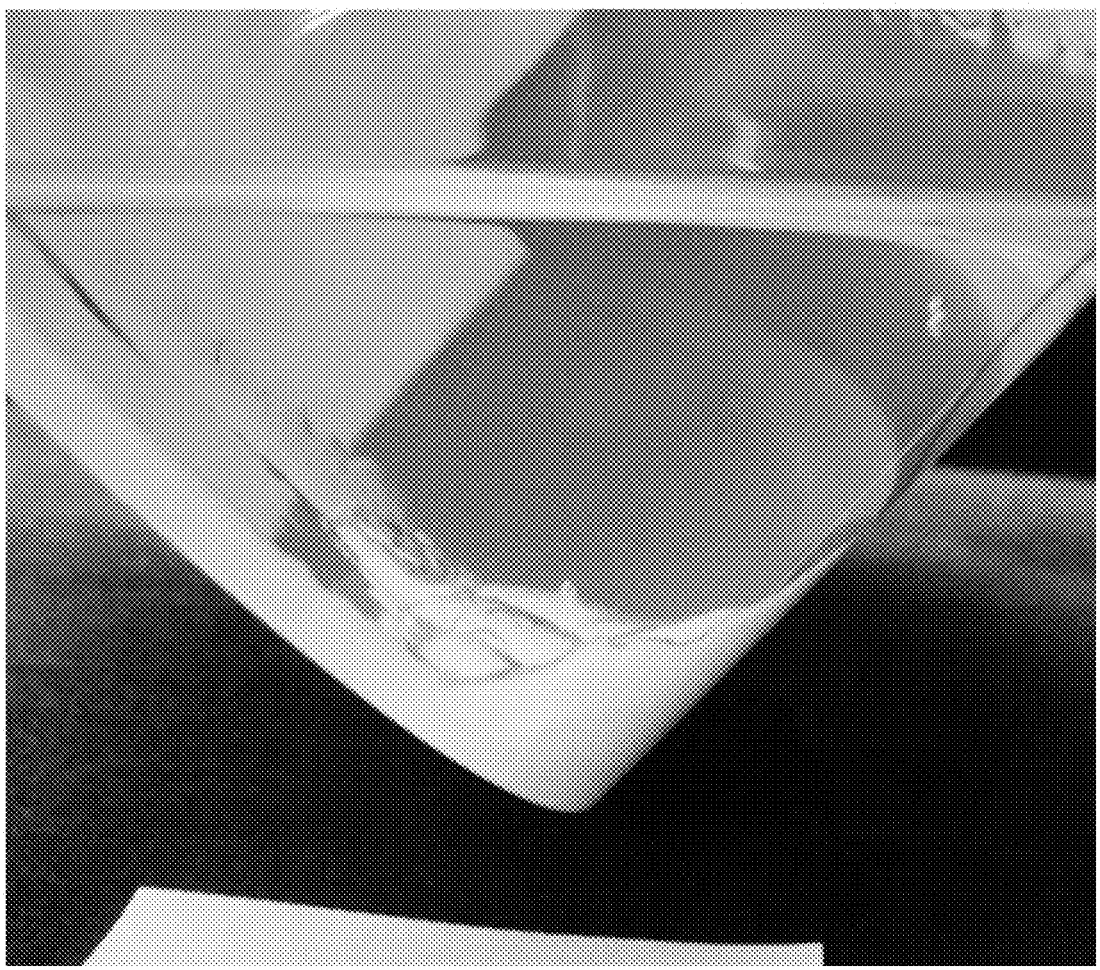
FIG. 4A shows the macroscopic separation of Comparative Example II (3.43% Tween 60).
Figure 4B:
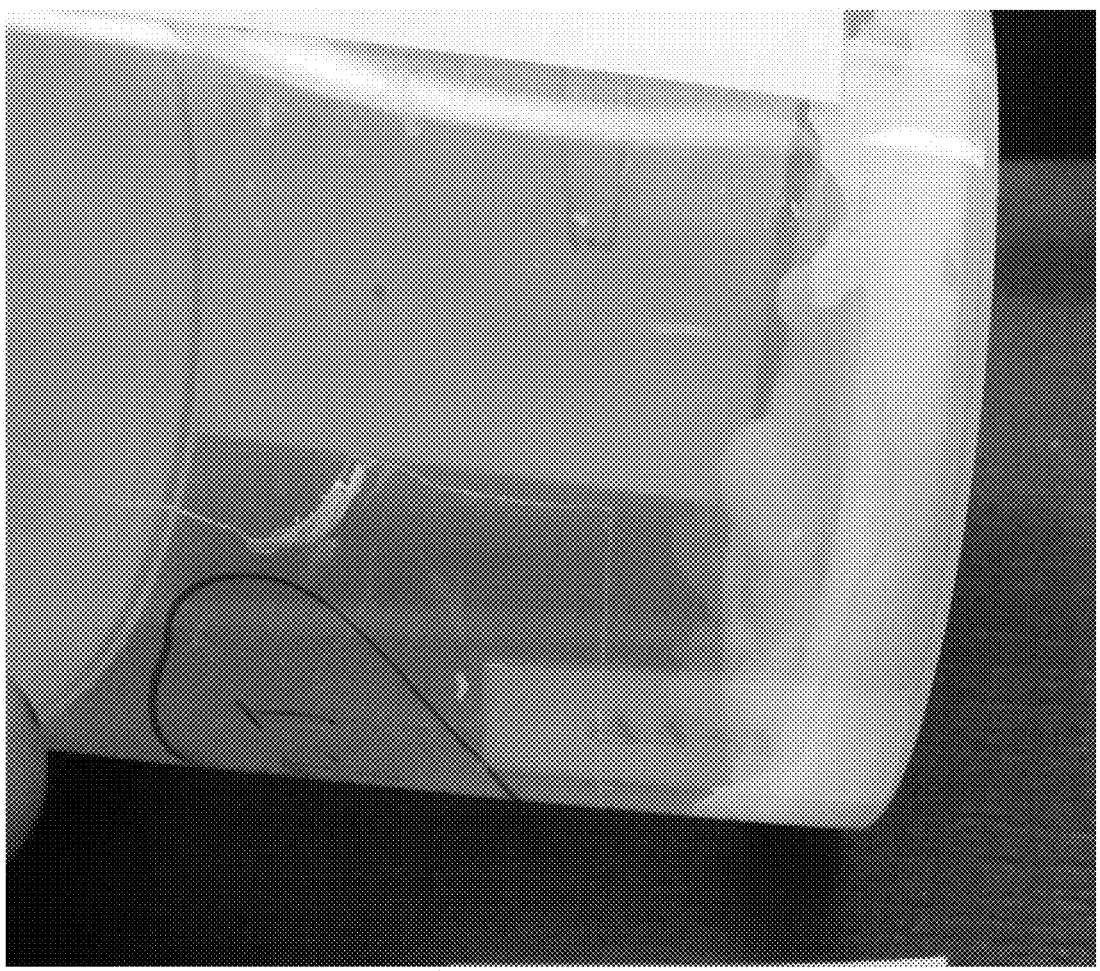
FIG. 4B shows the stable jammed oil-in-water emulsion of Example I-F (3.43% Tween 20).
Figure 5:
FIG. 5 shows the macroscopic separation of Comparative Example III (3.43% Tween 40).

FIG. 4A (Comparative Example II) shows the macroscopic separation of a high internal phase oil-in-water emulsion when 3.43% of Tween 60 was used as the emulsifier. FIG. 5 (Comparative Example III) shows the macroscopic separation of a high internal phase oil-in-water emulsion when Tween 40 was used as the emulsifier. In contrast, FIG. 4B (Example IF) shows a stable jammed oil-in-water emulsion when using Tween 20 as the emulsifier.

Figure 6A:
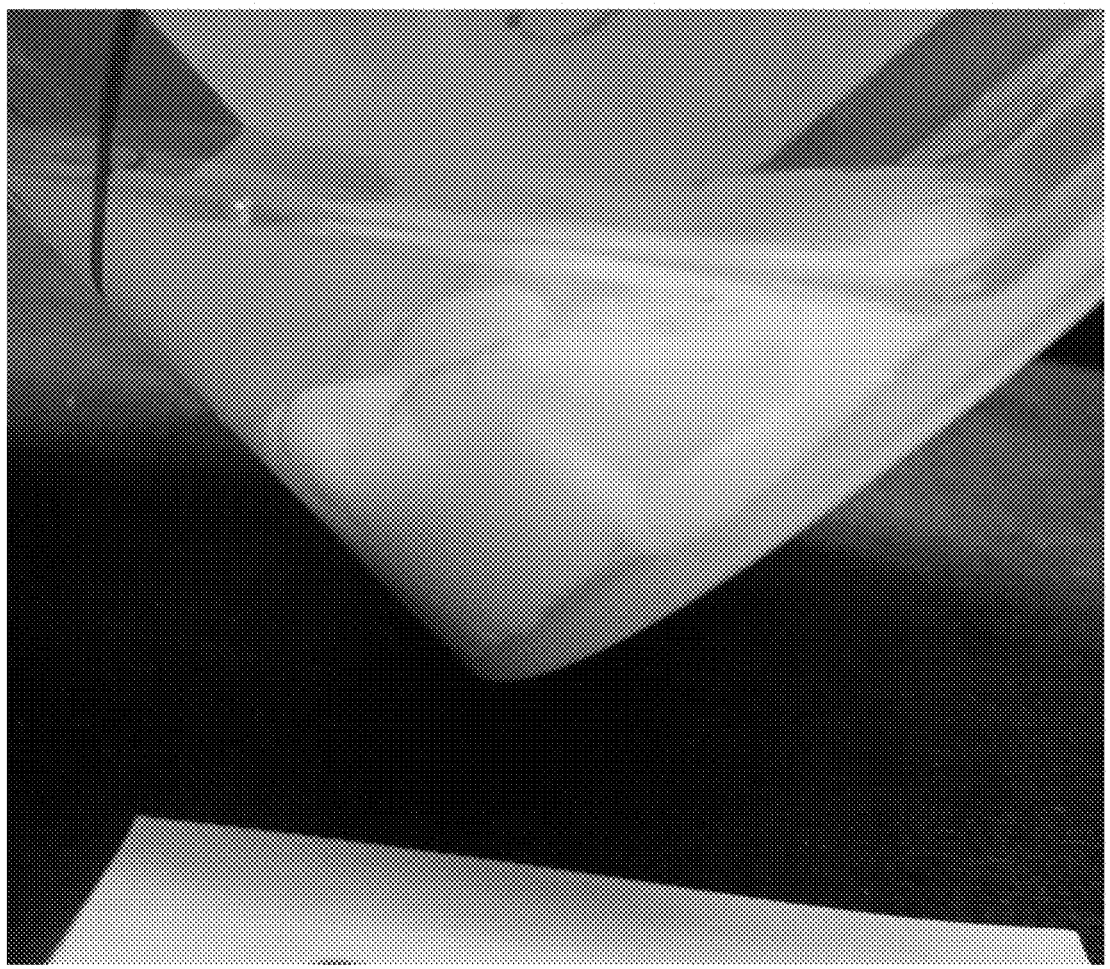
FIG. 6A shows the macroscopic separation of Comparative Example IV where the hydrophobic phase was added in a single addition.
Figure 6B:
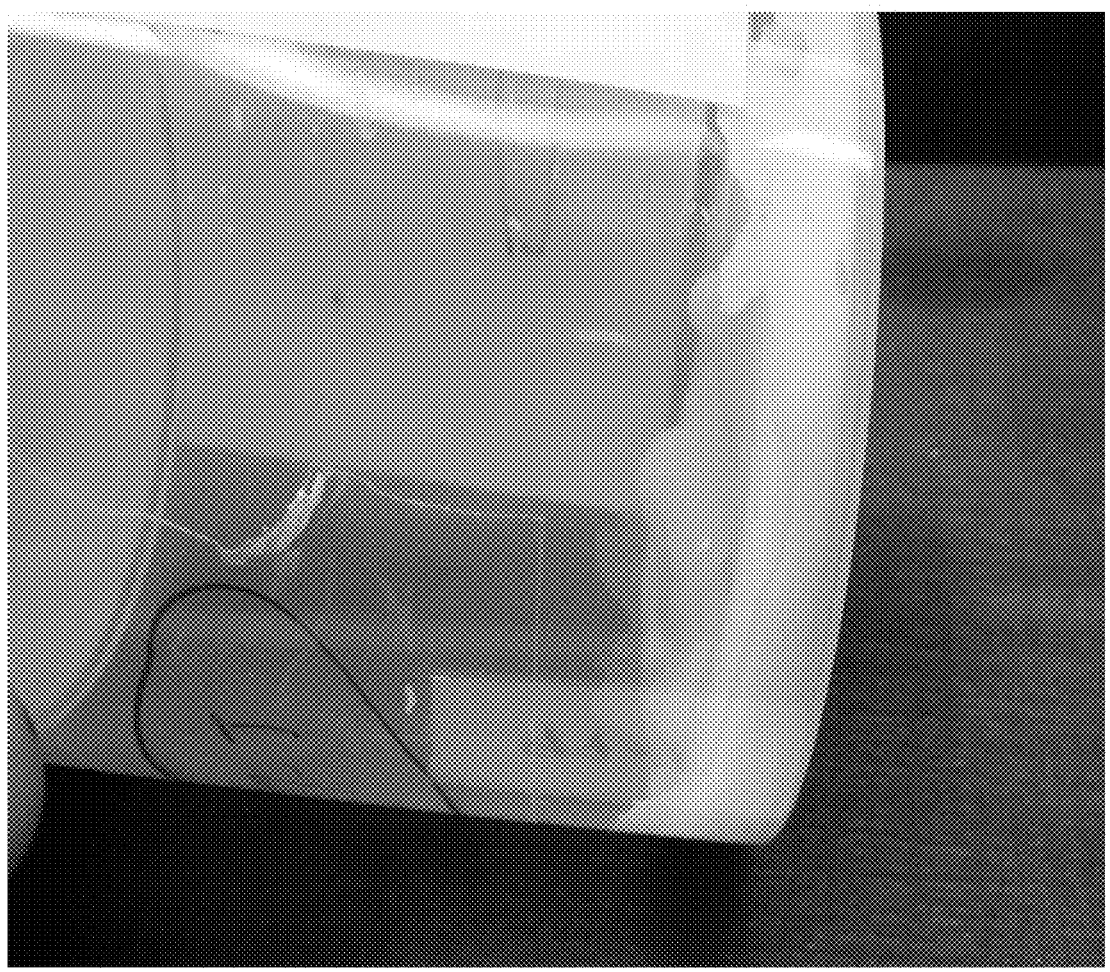
FIG. 6B shows the stable jammed oil-in-water emulsion of Example I-F where the hydrophobic phase was added sequentially with mixing after each addition.

FIG. 6A (Comparative Example IV) shows the macroscopic separation of a high internal phase oil-in-water emulsion while FIG. 6B (Example IF) shows a stable jammed oil-in-water emulsion. As shown in TABLE 1 and TABLE 3, Comparative Example IV and Example IF are identical except in the method of making. In Comparative Example IV, the hydrophobic phase was added in one single portion to the aqueous phase. In contrast, Example IF was made by adding the hydrophobic phase in multiple portions with mixing in between added portions.

Figure 7:
FIG. 7 shows Example II as a cohesive semi-solid bead when dispensed from a tube.

FIG. 7 shows that Example II is a stable jammed oil-in-water emulsion upon preparation. It appears as a cohesive semisolid bead when dispensed from a tube.

Figure 8A:
FIG. 8A shows macroscopic separation of Comparative Example V (Span 20 as an emulsifier).
Figure 8B:
FIG. 8B shows the stable jammed oil-in-water emulsion of Example III (Tween 20 as an emulsifier).

FIG. 8A shows the macroscopic separation of Comparative Example V when Span 20 was used as the emulsifier, while FIG. 8B shows a stable jammed oil-in-water emulsion of Example III when Tween 20 was used as an emulsifier. Example III showed no macroscopic separation after seven months at 23° C.

FIG. 9A shows a microscopic image of Comparative Example VI, which comprises a water-in-oil emulsion. FIG. 9A shows discrete droplets of aqueous phase dispersed in the hydrophobic phase. In contrast, FIG. 9B shows the stable jammed oil-in-water emulsion of Example IB. FIG. 9B shows discrete regions of hydrophobic phase with a thin continuous aqueous phase comprising the oral care active, which is hydrogen peroxide.

Figure 10A:
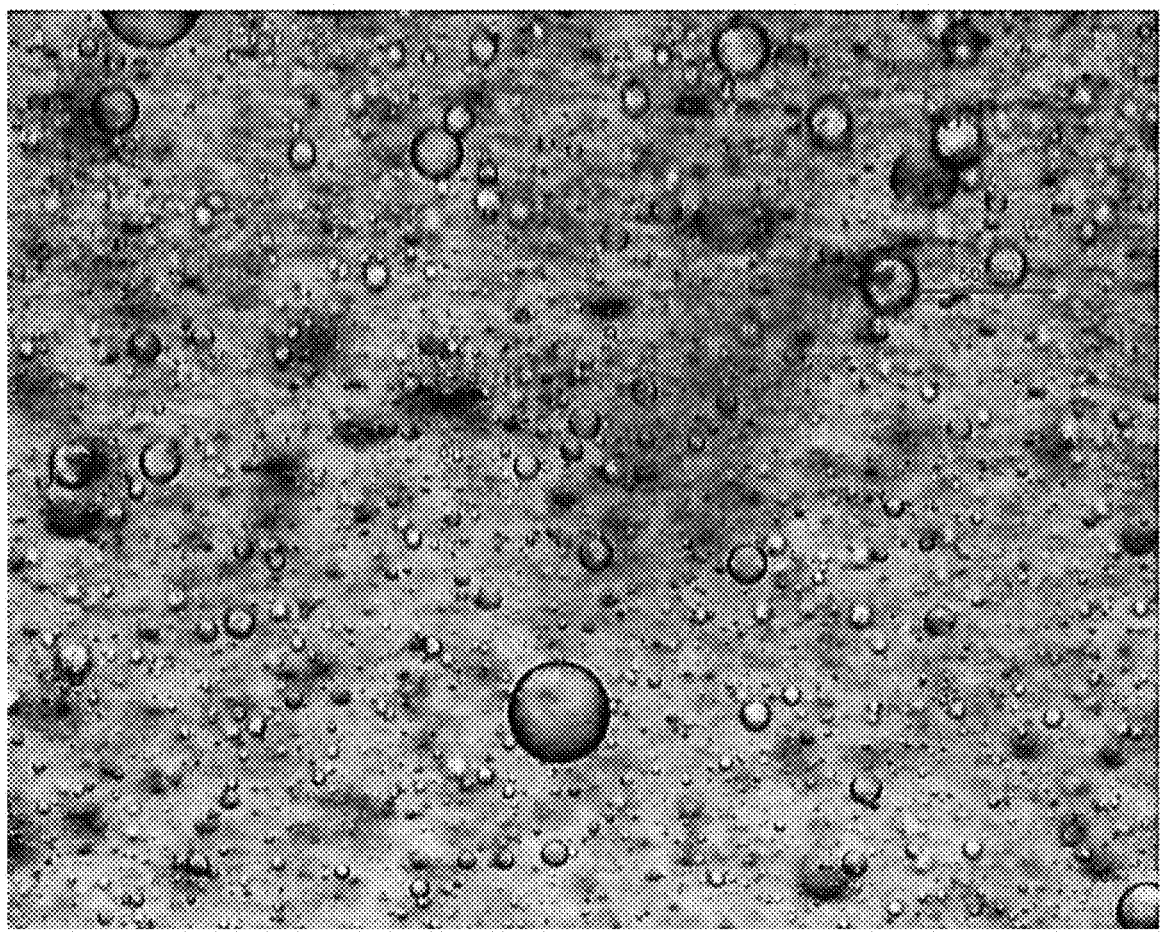
FIG. 10A shows a microscopic image of Comparative Example VII as a water-in-oil emulsion with discrete droplets of aqueous phase dispersed in the hydrophobic phase.
Figure 10B:
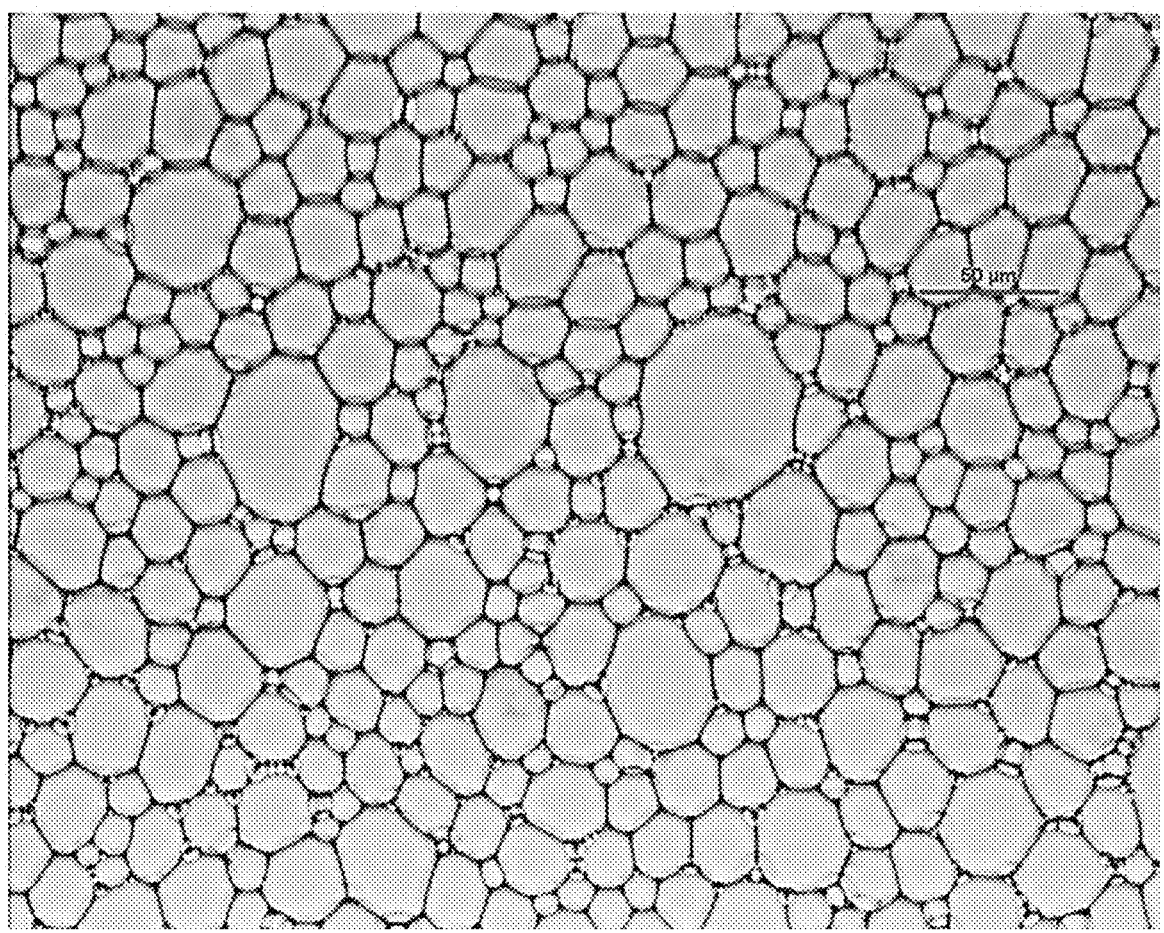
FIG. 10B shows Example I-B as a jammed oil-in-water emulsion with regions of oil dispersed in the aqueous phase.

FIG. 10A shows a microscopic image of Comparative Example VII a water-in-oil emulsion with discrete droplets of aqueous phase dispersed in the hydrophobic phase. In contrast, FIG. 10B shows Example IB as a jammed oil-in-water emulsion with regions of oil dispersed in the aqueous phase. Example IB and Comparative Example VII only differ in that Example IB comprises 1% of Tween 20 emulsifier while Comparative Example VII has no emulsifier.

Figure 11:
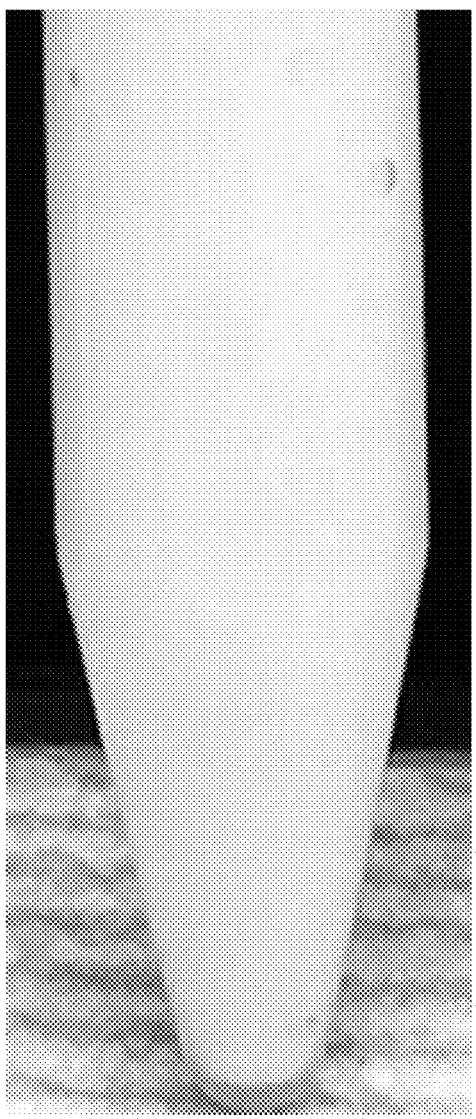
FIG. 11 shows Example I-B as a jammed oil-in-water emulsion after 90 days at 40° C.

FIG. 11 shows Example IB as a stable jammed oil-in-water emulsion after 90 days at 40° C. TABLE 7 shows that there is virtually no loss of $H_2O_2$ over the 90 days at 40° C., which indicates that Example IB is very stable to reactivity and macroscopic separation.

Figure 12A:
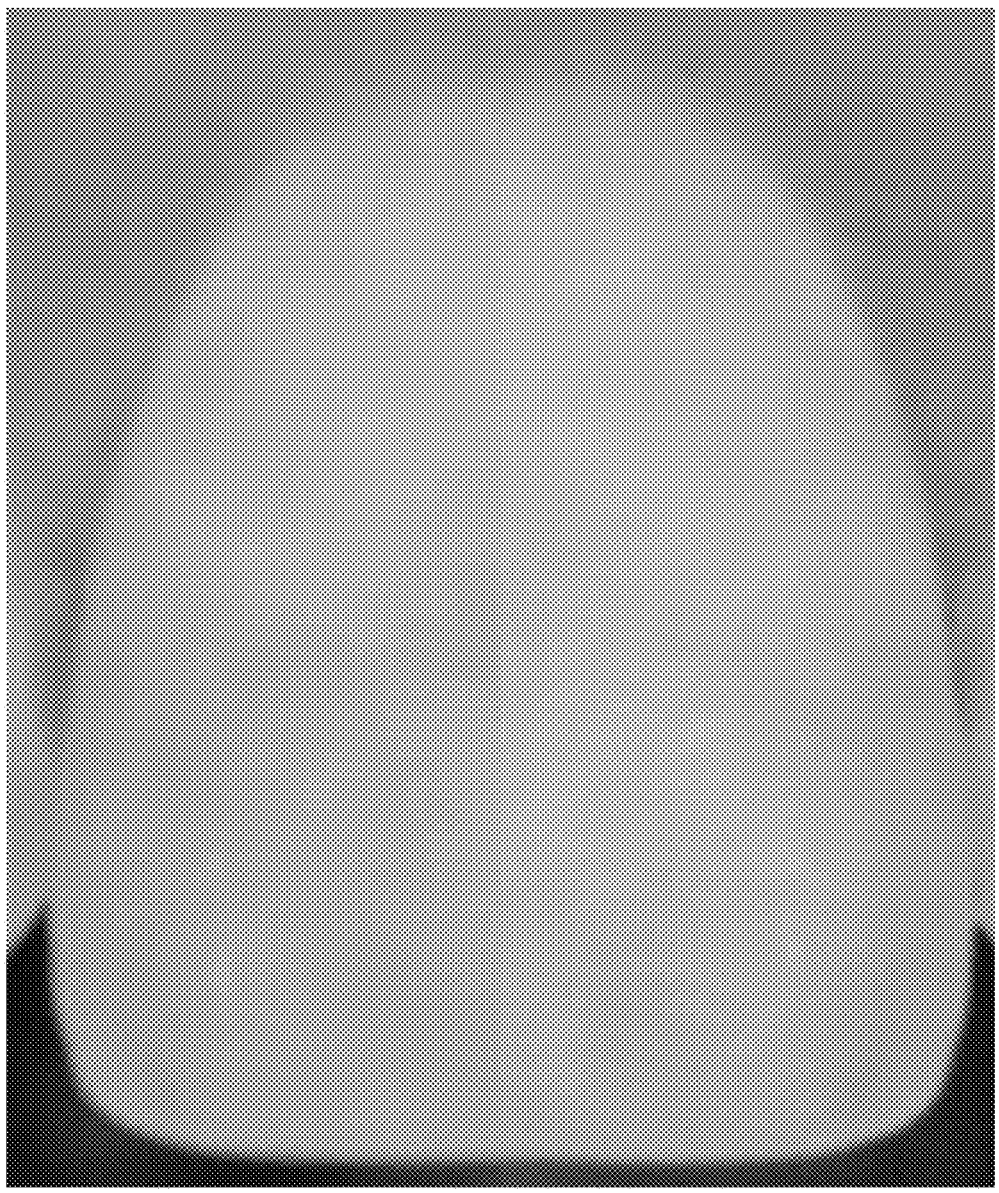
FIG. 12A shows the average decrease in yellowness against a baseline (left) after a single treatment with Example I-B delivered on a tray in combination with electromagnetic radiation.
Figure 12B:
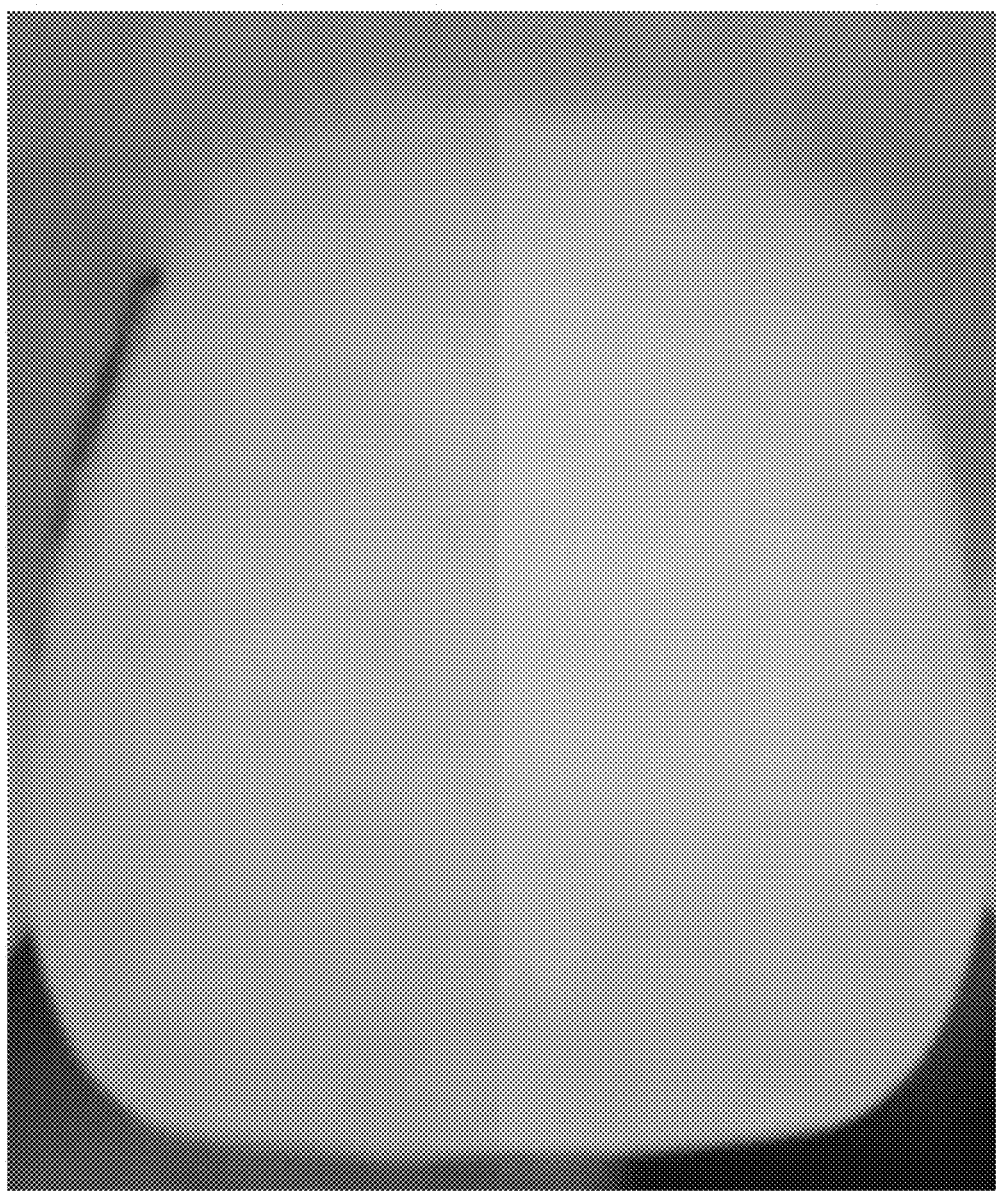
FIG. 12B shows the highest decrease in yellowness against a baseline (left) after a single treatment with Example I-B delivered on a tray in combination with electromagnetic radiation.

FIGS. 12A and 12B show the surprisingly high decrease in yellowness after 1 single treatment with Example I-B (delivered on a tray and combined with electromagnetic radiation as specified herein).

Figure 13:
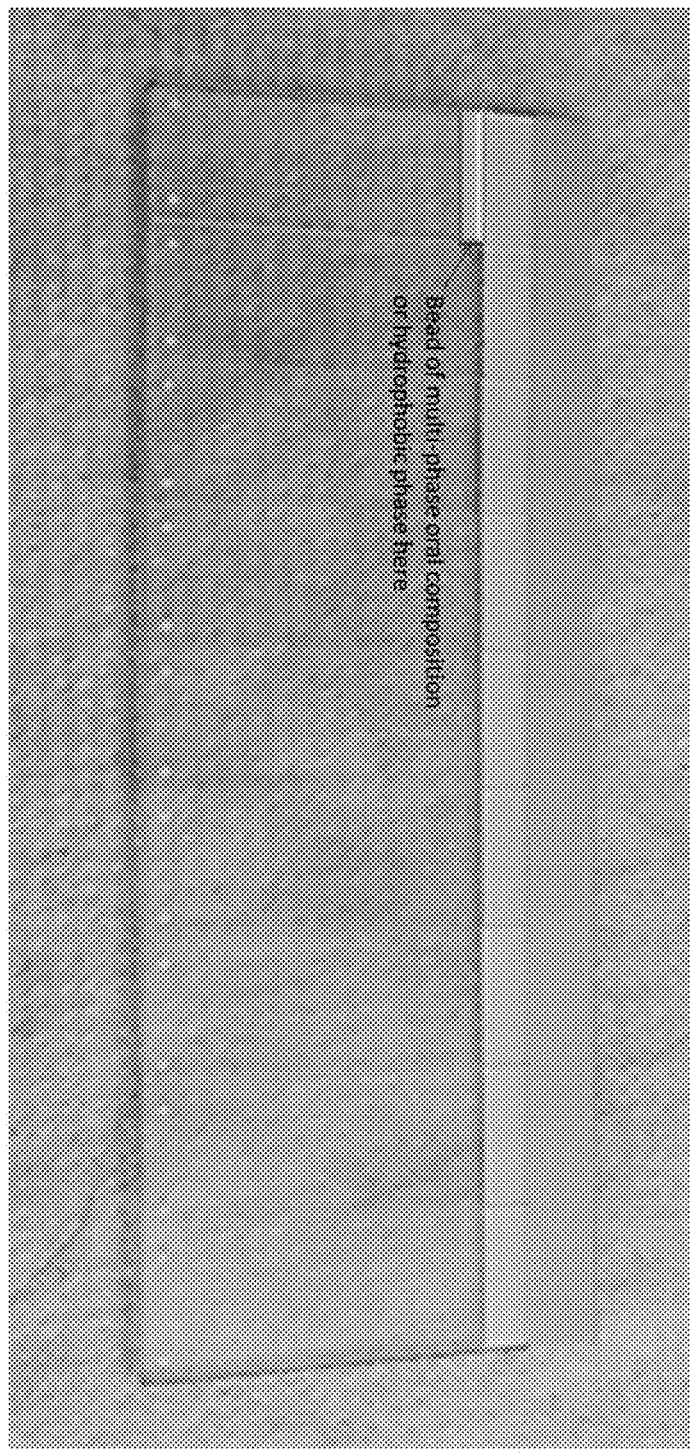
FIG. 13 shows 1) a holder for the microscope slides, 2) 9 microscope slides, 3) tape securing the slides to the holder, and 4) a sample sketch of a bead of a multi-phase oral care composition or hydrophobic phase applied to one of the slides.

FIG. 13 shows 1) a holder for the microscope slides, 2) 9 microscope slides, 3) tape securing the slides to the holder, and 4) a sample sketch of a bead of a multi-phase oral care composition or hydrophobic phase applied to one of the slides.

Figure 14:
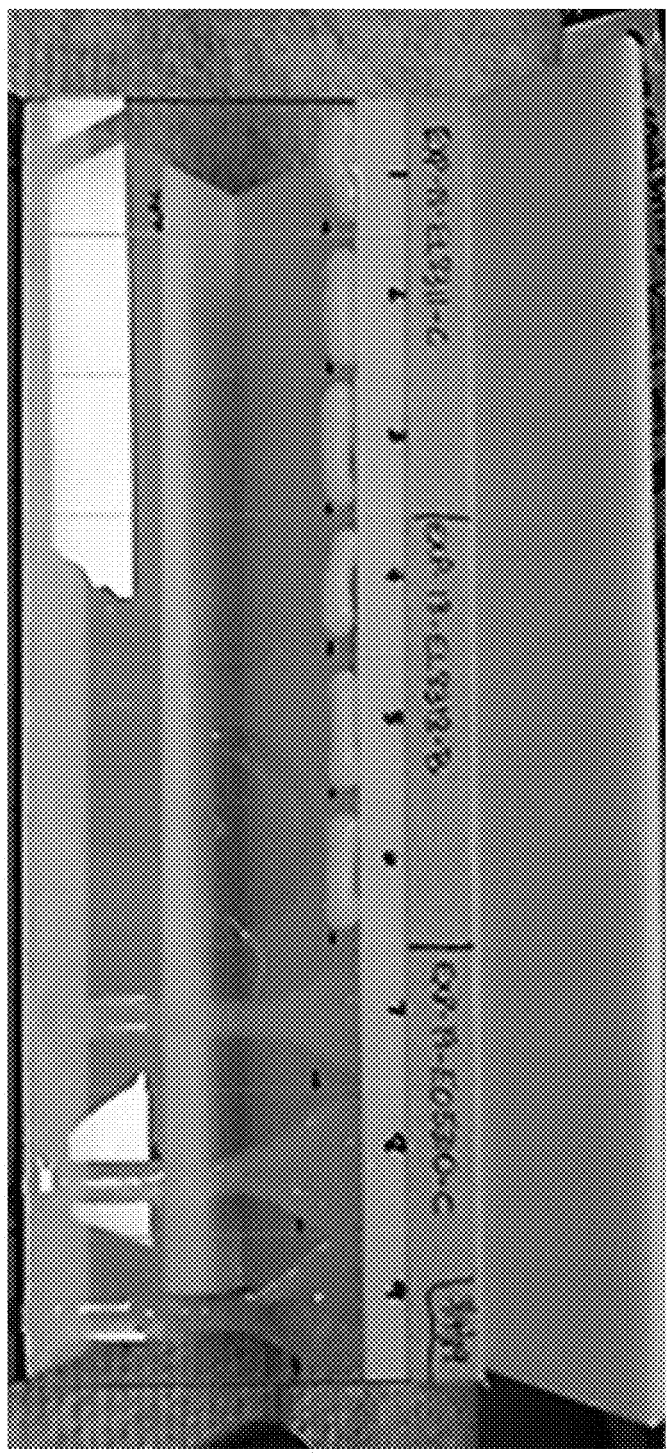
FIG. 14 shows 3 beads for 2 batches of Example I-B, and 3 beads of the validation composition for the slide flow method specified herein after it has been tilted at 45 degrees for 60 seconds. This image shows that the beads have barely flowed down the slides for Example I-B, but flowed all the way to the bottom of the slide for the validation composition for the slide flow method specified herein.

FIG. 14 shows 3 beads for 2 batches of Example I-B, and 3 beads of the validation composition for the slide flow method specified herein after it has been tilted at 45 degrees for 60 seconds. This image shows that the beads have barely flowed down the slides for Example IB, but flowed all the way to the bottom of the slide for the validation composition for the slide flow method specified herein. This indicates that the stable jammed oil-in-water emulsions will stay in place while in a delivery carrier.

Figure 15:
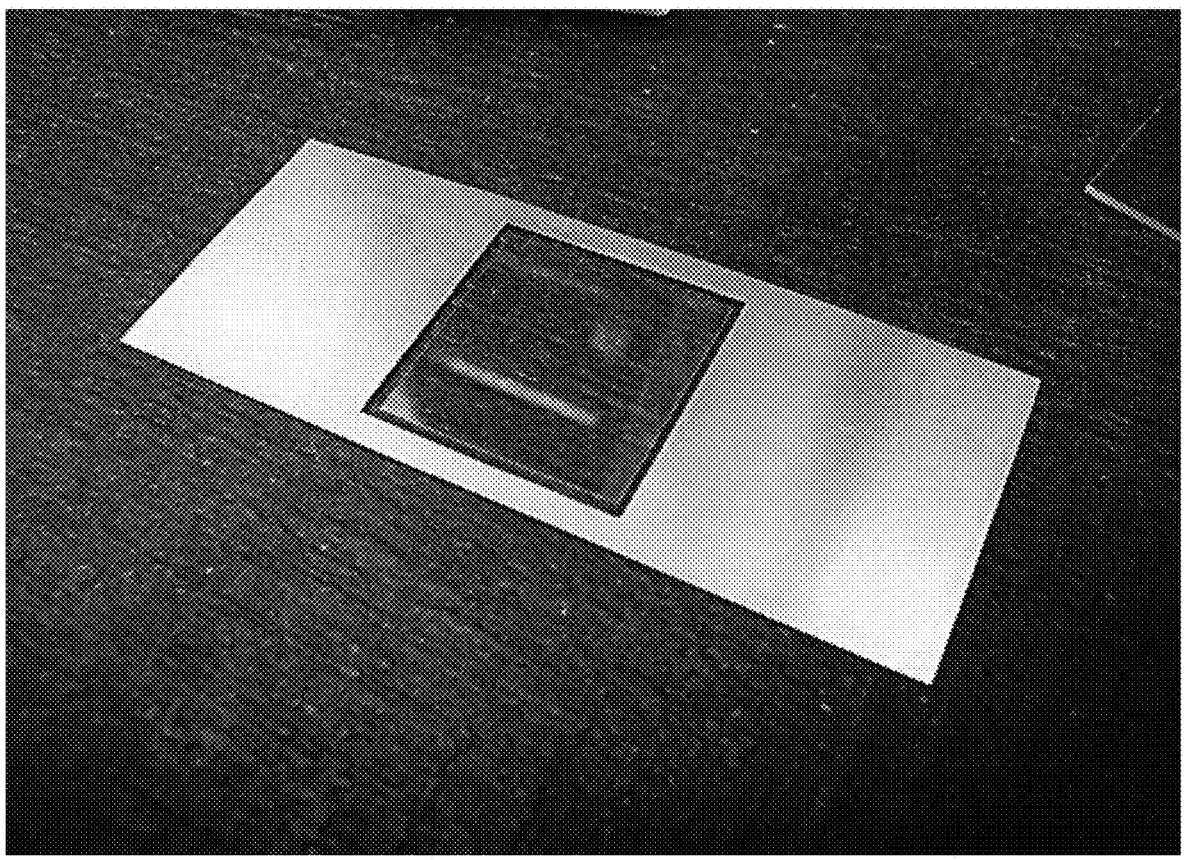
FIG. 15 shows the template and a coverslip that can be used to load a multi-phase composition of the present invention for observation under a microscope.
Figure 16A:
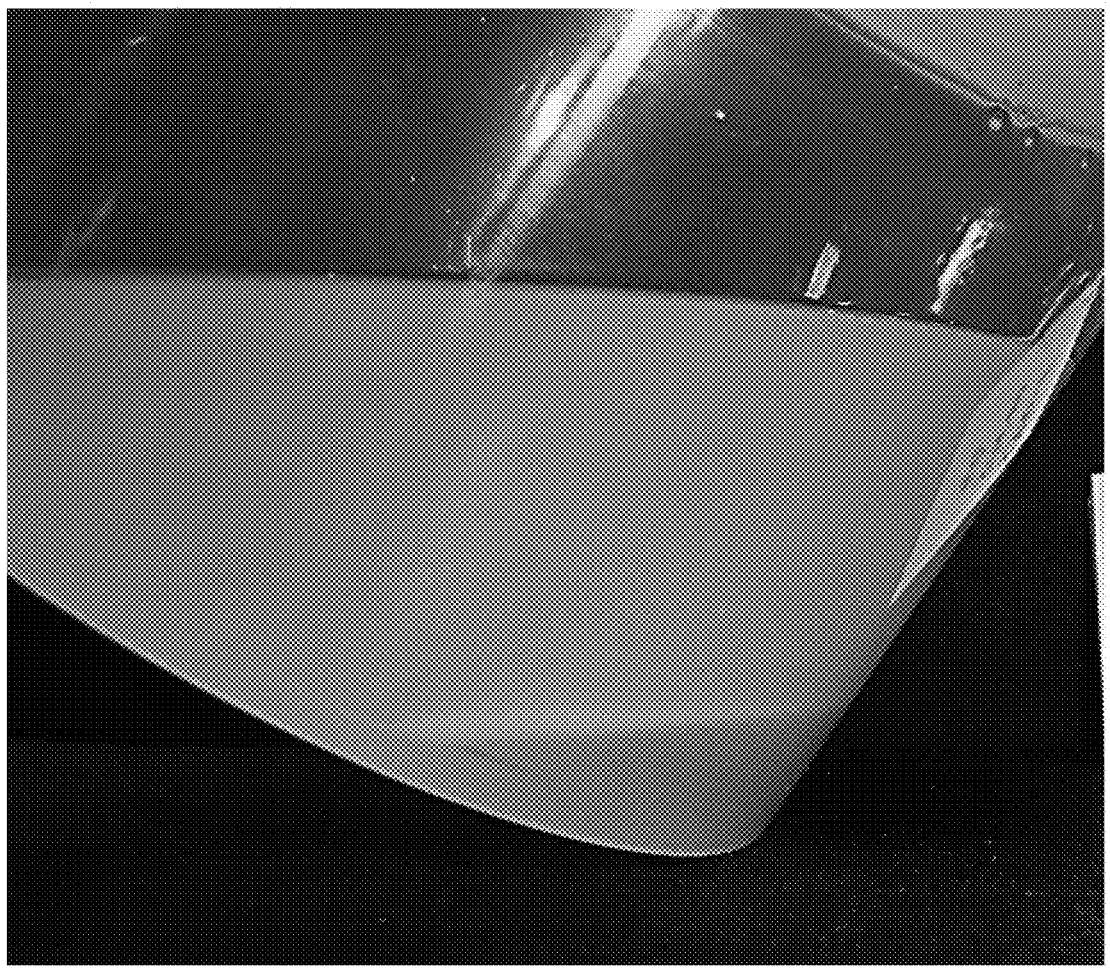
FIG. 16A shows the macroscopic separation within one hour of Comparative Example VIII being made where the minor aqueous phase was added to the major hydrophobic phase.
Figure 16B:
FIG. 16B shows the stable jammed oil-in-water emulsion of Example I-B where the major hydrophobic phase was added to the minor aqueous phase.

FIG. 15 shows the template and a coverslip that can be used to load a multi-phase composition of the present invention for observation under a microscope FIG. 16 A shows Comparative Example VIII and FIG. 16B shows Example I-B. Importantly, as shown in TABLEs 1 and 4, are identical in composition except for the method of making. In Comparative Example VIII, the aqueous phase was added to the hydrophobic phase, which led to macroscopic separation less than one hour after addition. In contrast, in Example I-B, the hydrophobic phase was portion-wise added to the aqueous phase while mixing between each addition of a portion of the hydrophobic phase. Example I-B is shown in FIG. 16B as a jammed oil-in-water emulsion that has shown no macroscopic separation after storage at room temperature (~23° C.) for seven months.

TABLES 1 and 2 show inventive examples, while TABLES 3 and 4 show comparative examples, as described herein.

TABLE 5 shows the mean peroxide of two samples comprising hydrogen peroxide. Even though both compositions had the same level of $H_2O_2$, Example IB which was a stable jammed oil-in-water emulsion delivered a higher mean peroxide concentration smeared onto test strips than Comparative Example VI which was a water-in-oil emulsion.

TABLE 6 shows the whitening efficacy of several composition. Specifically, this table shows that even though 1) both compositions had the same level of $H_2O_2$ (3%), and, 2) the treatment time for Example I-B was shorter (60 minutes Vs. 90 minutes), Example I-B, which comprises an oil-in-water emulsion, delivered a higher mean decrease in yellowness than Comparative Example VII which comprises a water-in-oil emulsion TABLE 8 shows that even though all the examples had the same level of H2O2, Example I-B with the lowest Brookfield Viscosity delivered the highest mean peroxide concentration smeared onto test strips. TABLE 9 shows the yield stress for Example IB.

TABLE 10 shows that even though Example I-B, which comprises a stable jammed oil-in-water emulsion has a higher water-dispersibility, it also delivered a higher mean decrease in yellowness than Comparative Example VII which comprises a water-in-oil emulsion TABLE 11 shows that Example I-B which comprises a stable jammed oil-in-water emulsion has a Brookfield Viscosity much higher than the hydrophobic phase and the aqueous phase from which it was made.

TABLE 12 shows that Example I-B which comprises a stable jammed oil-in-water emulsion has a Yield Stress higher than the hydrophobic phase and the aqueous phase from which it was made.

TABLE 13 shows that the D[4,3] equivalent-diameter of regions of hydrophobic phase decreases as the percentage of hydrophobic phase increases and the percentage of aqueous phase of increases.

TABLE 14 shows that the D[4,3] equivalent-diameter of regions of hydrophobic phase decreases as the percentage of emulsifier increases.

The microscope images, as described herein, were captured using the following procedure to load the multi-phase oral care composition on the microscope slide. In general, the sample was sandwiched between the microscope slide and the coverslip, such that the sample was no more than 100 microns thick. This was done by the following procedure:

1. Place a microscope slide (VWR Micro Slides, Super Frost Plus, 25×75×1 mm, manufactured by VWR International, Radnor, Pa.; purchased from VWR, Batavia, Ill., catalog number 48311-703) with the frosted side facing up on a clean working surface.
2. Carefully dab a disposable transfer pipet with a fine tip (5.8 ml polyethylene, purchased from VWR, Batavia, Ill., catalog number 414004-020) into the multi-phase oral care composition taking care not to suction the composition into the pipet.
3. Transfer about 5 mg of the composition from the tip of the transfer pipet to the surface of the microscope slide. This may be done by gently tapping the tip of the transfer pipet on the microscope slide.

4. Hold a microscope coverslip (VWR Micro Cover Glass, 22 mm×22 mm×generally about 130 microns thick, purchased from VWR, Batavia, Ill., catalog number 48366 067) over the sample and center it. Gently drop the coverslip onto the sample.
5. Place a template (about 230 microns thick, FIG. 15) with a square hole cut in the middle around the coverslip, taking care not to touch the coverslip. Place a second microscope slide on top of the coverslip and press down against the template. This will ensure that the sample is no more than 100 microns thick. Note, the thickness of the sample may be less than 100 microns in certain cases, depending on the viscosity and surface tension of the sample.
6. The sample is now ready to be viewed under a microscope within about 10 minutes.

The bleaching efficacy of Example I-B was measured per the clinical protocol disclosed herein. Specifically, the bleaching efficacy of Example-I-B was measured in a single-center, single-treatment clinical study with 10 adults who had never had a professional, over-the-counter or investigational tooth bleaching treatment. All participants were at least 18 years old, had all four measurable maxillary incisors, and had no self-reported tooth sensitivity. Participants were assigned to the following treatment group:

Example I-B (10 participants, mean L* of 73.848 and mean b* of 15.172)

The participants were treated once daily for 3 days, as described herein.

The participants demonstrated a statistically significant (p<0.0001) reduction in yellowness (−Δb*) at all tested time-points relative to Baseline.

The bleaching efficacy of Comparative Example VII was measured in a controlled, single-center, clinical study with 11 adults who had never had a professional, over-the-counter or investigational tooth bleaching treatment. All participants were at least 18 years old, had all four measurable maxillary incisors, and had no self-reported tooth sensitivity. Participants were assigned to the following treatment group:

Comparative Example VII (11 participants, mean L* of 73.667 and mean b* of 15.138)

The bleaching efficacy of Comparative Example VII was measured per the clinical protocol disclosed herein with the following modifications:

The maxillary anterior teeth of the participants were treated with the multi-phase oral care composition for 90 minutes (instead of 60 minutes) once daily using a disposable polyethylene strip as the delivery carrier. A disposable strip was used instead of a tray because Comparative Example VII is not as easy to rinse from a tray as Example I-B. The polyethylene strips were 66 mm×15 mm in size and 0.0178 mm thick. From 0.6 g to 0.8 g of the multi-phase oral care composition was applied across each strip of polyethylene prior to applying to the maxillary anterior teeth. Within these 90 minutes, the composition was re-applied to the teeth using a new strip every 30 minutes for a total of 3×30-minute applications.

Within each 30-minute application, a trained hygienist applied electromagnetic radiation toward the facial surfaces of the maxillary anterior teeth during the last 10 minutes. The three 30-minute applications were applied back-to-back for a total of 90 minutes per treatment, once daily. The electromagnetic radiation was directed toward the teeth through the strip and through the oral composition.

Digital images were collected according to the clinical protocol at baseline and the day after 1 and 2 treatments.

The electromagnetic radiation was delivered using the source of electromagnetic radiation described herein in the section titled "Clinical protocol". The intensity of the electromagnetic radiation from 400 nm to 500 nm measured at the central axis of each cone of electromagnetic radiation exiting at the exit surface of the transparent window through which the electromagnetic radiation passes toward the maxillary anterior teeth was measured to be from about 175 $mW/cm^2$ to about 225 $mW/cm^2$, as measured by the method disclosed herein. Once 90 minutes of treatment was completed the strip was removed. The participants were treated once daily for 3 days.

The participants demonstrated a statistically significant (p<0.0001) reduction in yellowness (−Δb*) at all tested time-points relative to Baseline. TABLE 6 shows the results.

The results in TABLE 6 show that, 1) even though both compositions had the same level of $H_2O_2$, and 2) the treatment time for the Example oil-in-water emulsion was shorter (60 minutes Vs. 90 minutes), it delivered a higher mean decrease in yellowness than the Comparative Example water-in-oil emulsion. Specifically, 1) after 1×60-minute treatment, Comparative Example VII delivered a mean decrease in yellowness of 2.185 while Example I-B (oil-in-water emulsion) delivered a mean decrease in yellowness of 2.908—this is about 33% more efficacy in 33% less time, and 2) after 2×60-minute treatments, Comparative Example VII delivered a mean decrease in yellowness of 3.333 while Example I-B (oil-in-water emulsion) delivered a mean decrease in yellowness of 4.214—this is about 26% more efficacy in 33% less time. These results are surprising because, 1) both compositions had the same level of $H_2O_2$ (3%), 2) the teeth were treated with 3×10 minutes electromagnetic radiation with both compositions, and 3) the treatment time for the Example oil-in-water emulsion was 33% shorter (60 minutes Vs. 90 minutes) than the Comparative Example water-in-oil emulsion.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition comprising jammed oil-in-water emulsion, the jammed oil-in-water emulsion comprising:
   (a) at least partially continuous aqueous phase;
   (b) discontinuous hydrophobic phase;
   (c) oral care active agent; and
   (d) emulsifier with a hydrophilic-lipophilic balance of from about 11 to about 60.

2. The oral care composition of claim 1, wherein the oral care composition comprises from about 80% to about 99%, by weight of the composition, of the hydrophobic phase.

3. The oral care composition of claim 1, wherein the oral care composition comprises from about 1% to about 20%, by weight of the aqueous phase, of the aqueous phase.

4. The oral care composition of claim 1, wherein the oral care composition comprises from about 5% to about 15%, by weight of the aqueous phase, of the aqueous phase.

5. The oral care composition of claim 1, wherein the aqueous phase comprises the oral care active agent.

6. The oral care composition of claim 1, wherein the hydrophobic phase comprises the oral care active agent.

7. The oral care composition of claim 5, wherein the oral care active agent comprises bleaching agent, anti-caries agent, anti-tartar agent, remineralization agent, wound healing agent, anti-inflammatory agent, antibacterial agent, metal ion source, anti-glycolytic agent, amino acid, probiotic, prebiotic, postbiotic, polyphosphate, buffer, anti-sensitivity agent, or combinations thereof.

8. The oral care composition of claim 7, wherein the oral care active agent comprises hydrogen peroxide.

9. The oral care composition of claim 8, wherein the aqueous phase comprises from about 5% to about 67%, by weight of the composition, of the oral care active agent.

10. The oral care composition of claim 1, wherein the oral care composition comprises from about 0.01% to about 10%, by weight of the composition, of the emulsifier.

11. The oral care composition of claim 1, wherein the emulsifier comprises a polysorbate, an alkyl sulfate, or combinations thereof.

12. The oral care composition of claim 1, wherein the emulsifier comprises polysorbate 20, polysorbate 40, sodium lauryl sulfate, or combinations thereof.

13. The oral care composition of claim 1, wherein the emulsifier comprises one or more hydrophobic tails, the one or more hydrophobic tails having from about 6 to about 20 carbon atoms.

14. The oral care composition of claim 13, wherein the one or more hydrophobic tails has up to 4 branches.

15. The oral care composition of claim 1, wherein the emulsifier comprises a blend of multiple emulsifiers.

16. The oral care composition of claim 1, wherein the emulsifier is hydrophilic, miscible with water, immiscible with mineral oil, or combinations thereof.

17. A method of applying the oral care composition of claim 1 to at least one tooth of a consumer.

18. A method of applying the oral care composition of claim 1 to at least one tooth of a consumer in a delivery carrier.

19. The method of claim 18, wherein the delivery carrier is a tray or strip.

20. A jammed oil-in-water emulsion composition comprising a discontinuous hydrophobic phase prepared by a process comprising the steps of:
   (a) combining a portion of hydrophobic composition with aqueous composition, the aqueous phase comprising oral care active agent and emulsifier with a hydrophilic-lipophilic balance of from about 11 to about 60;
   (b) mixing the portion of hydrophobic composition and aqueous composition; and
   (c) repeating steps (a) and (b) until the entire hydrophobic composition has been combined with the aqueous composition.

21. The composition of claim 20, wherein the oral care active agent comprises hydrogen peroxide.

22. The composition of claim 20, wherein the hydrophobic composition is combined with the aqueous composition by portion-wise addition, gradual addition, or combinations thereof.

23. The composition of claim 20, wherein the oral care active agent comprises bleaching agent, anti-caries agent, anti-tartar agent, remineralization agent, wound healing agent, anti-inflammatory agent, antibacterial agent, metal ion source, anti-glycolytic agent, amino acid, probiotic, prebiotic, postbiotic, polyphosphate, buffer, anti-sensitivity agent, or combinations thereof.

24. The composition of claim 20, wherein the composition comprises from about 0.01% to about 10%, by weight of the composition, of the emulsifier.

25. The composition of claim 20, wherein the emulsifier comprises a polysorbate, an alkyl sulfate, or combinations thereof.

26. The composition of claim 20, wherein the emulsifier comprises polysorbate 20, polysorbate 40, sodium lauryl sulfate, or combinations thereof.

27. The composition of claim 20, wherein the emulsifier comprises one or more hydrophobic tails, the one or more hydrophobic tails having from about 6 to about 20 carbon atoms.

28. The composition of claim 27, wherein the one or more hydrophobic tails has up to 4 branches.

29. A jammed oil-in-water emulsion composition comprising a discontinuous hydrophobic phase prepared by a process comprising the steps of combining hydrophobic composition with aqueous composition in a continuous or pulsed fashion while continuously stirring the hydrophobic composition and the aqueous composition until all of the hydrophobic composition has been combined with the aqueous composition, wherein the aqueous phase comprises oral care active agent and emulsifier with a hydrophilic-lipophilic balance of from about 11 to about 60.

30. The composition of claim 29, wherein the oral care active agent comprises bleaching agent, anti-caries agent, anti-tartar agent, remineralization agent, wound healing agent, anti-inflammatory agent, antibacterial agent, metal ion source, anti-glycolytic agent, amino acid, probiotic, prebiotic, postbiotic, polyphosphate, buffer, anti-sensitivity agent, or combinations thereof.

31. The composition of claim 29, wherein the composition comprises from about 0.01% to about 10%, by weight of the composition, of the emulsifier.

32. The composition of claim 29, wherein the emulsifier comprises a polysorbate, an alkyl sulfate, or combinations thereof.

33. The composition of claim 29, wherein the emulsifier comprises polysorbate 20, polysorbate 40, sodium lauryl sulfate, or combinations thereof.

34. The composition of claim 29, wherein the emulsifier comprises one or more hydrophobic tails, the one or more hydrophobic tails having from about 6 to about 20 carbon atoms.

35. The composition of claim 34, wherein the one or more hydrophobic tails has up to 4 branches.

* * * * *